US006300376B1

(12) United States Patent
Walsh et al.

(10) Patent No.: US 6,300,376 B1
(45) Date of Patent: *Oct. 9, 2001

(54) INDANE DIMER COMPOUNDS AND THEIR PHARMACEUTICAL USE

(75) Inventors: John Walsh, Ballinrobe; Neil Frankish, Dublin; Helen Sheridan, Dublin; Ronan Farrell, Dublin; William Byrne, Dublin, all of (IE)

(73) Assignee: Venantius Limited, Dublin (IR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/093,060

(22) Filed: Jun. 8, 1998

Related U.S. Application Data

(63) Continuation of application No. PCT/IE96/00080, filed on Jun. 12, 1996.

(30) Foreign Application Priority Data

Dec. 6, 1995 (IE) .................................................. 950922
Oct. 31, 1996 (IE) .................................................. 960762

(51) Int. Cl.$^7$ .................................................. A01N 35/00
(52) U.S. Cl. .................... 514/680; 514/691; 514/765; 568/309; 568/326; 568/330; 568/327; 568/715; 568/813; 585/27; 585/420
(58) Field of Search ...................... 585/27, 420; 568/326, 568/330, 309, 715, 813, 327; 514/680, 691, 765

(56) References Cited

PUBLICATIONS

Journal Chemical Society, 1951, pp. 863–867.
Chemical Abstracts, vol. 55, 1961, pp. 27227–27228.
Journal Organic Chemistry, 1958, vol. 23, pp. 1507–1510.
Journal of American Chemical Society, 1959, vol. 82, pp. 1452–1457.
Condensed Aromatic Compounds, 1967, vol. 67, pp. 53901–53902.
Chemical Communications, 1967, vol. 14, pp. 719–720.
Acta Chemica Scandinavica B, 1974, vol. 28, pp. 39–44.
Current Sciences, 1982, vol. 51, No. 5, pp. 233–234.
Tetrahedron Letters, 1985, vol. 26, No. 5, pp. 571–574.
Current Science, 1989, vol. 58, No. 19, pp. 1090–1091.
Tetrahedron, 1991, vol. 47, No. 25, pp. 4383–4408.
Chemical Abstracts, 1994, vol. 120, p. 211915.
Chemical Abstracts, 1966, vol. 64, p. 19785.
Chemical Abstracts, 1984, vol. 101, p. 130367.
Chemical Abstracts, 1973, vol. 78, p. 72624.
Chemical Abstracts, 1995, vol. 123, p. 340333.
Chemical Abstracts, 1965, vol. 62, pp. 2831–2832.
Chemical Abstracts, 1970, vol. 72, p. 43240.
Chemical Abstracts, 1966, vol. 64, pp. 5035–5036.
Chemical Abstracts, 1994, vol. 121, p. 57113.
Chemical Abstracts, 1975, vol. 84, p. 104665.
Chemical Abstracts, 1966, vol. 64, pp. 19369–19370.
Chemical Abstracts, 1935, vol. 29, pp. 7971–7972.
Chemical Abstracts, 1975, vol. 84, p. 16883.
Chemical Abstracts, 1967, vol. 67, p. 53500.
Chemical Abstracts, 1972, vol. 76, p. 72293.
Chemical Abstracts, 1995, vol. 123, p. 82705.
Journal of Organic Chemistry, 1982, vol. 47, pp. 2593–2598.
Chemical Abstracts, 1993, vol. 120, pp. 243801
Chemical Abstracts, 1991, vol. 115, p. 160070.
Chemical Abstracts, 1984, vol. 101, p. 130267.
Chemical Abstracts, 1982, vol. 96, p. 198807.
Chemical Abstracts, 1986, vol. 105, p. 208308.
Chemical Abstracts, 1985, vol. 105, p. 114467.
Chemical Abstracts, 1990, vol. 112, p. 138709.
Chemical Abstracts, 1989, vol. 111, p. 77302.
Chemical Abstracts, 1986, vol. 104, pp. 158307.
Chemical Abstracts, 1983, vol. 99, p. 174929.
Chemical Abstracts, 1985, vol. 105, p. 6283.
Chemical Abstracts, 1988, vol. 110, p. 23477.
Justus Liebigs Annalen der Chemie, vol. 639, 1961, pp. 204–213.
Recueil des Travaux Chimiques des Pays–Bas, vol. 107, 1988, pp. 549–562.
Tetrahedron Letters, vol. 33 No. 6, 1992, pp. 821–824.
Berichte des Deutschen Chemischen Gesellschaft, vol. 57, 1924, pp. 1838–1851.
Phosphorus and Sulfur, vol. 33, 1987, pp. 83–86.
Journal of General Chemistry USSR, vol. 35, 1965, pp. 830–833.
Berichte der Deutschen Chemischen Gesellschaft, vol. 65, 1932, pp. 463–467.
Journal of the American Chemical Society, vol. 62, 1940, pp. 3401–3404.
Journal of the American Chemical Society, vol. 103, 1981, pp. 4499–4508.
Anales de Quimica, vol. 64, No. 7–8, 1968, pp. 647–658.
Journal of the Chemical Society, Perkin Transactions I, 1983, pp. 2399–2407.
Chemische Berichts, vol. 121, 1988, pp. 2195–2200.

*Primary Examiner*—Sreeni Padmanabhan
(74) *Attorney, Agent, or Firm*—Jacobson Holman, PLLC

(57) ABSTRACT

Indane dimer compounds and their pharmaceutical use particularly to achieve smooth muscle relaxing activity and/or mast cell stabilizing activity and/or anti-inflammatory activity are described.

24 Claims, 4 Drawing Sheets

Tidal Volume

Rate of Respiration

INDANE DIMER COMPOUNDS AND THEIR PHARMACEUTICAL USE

Figure 1:
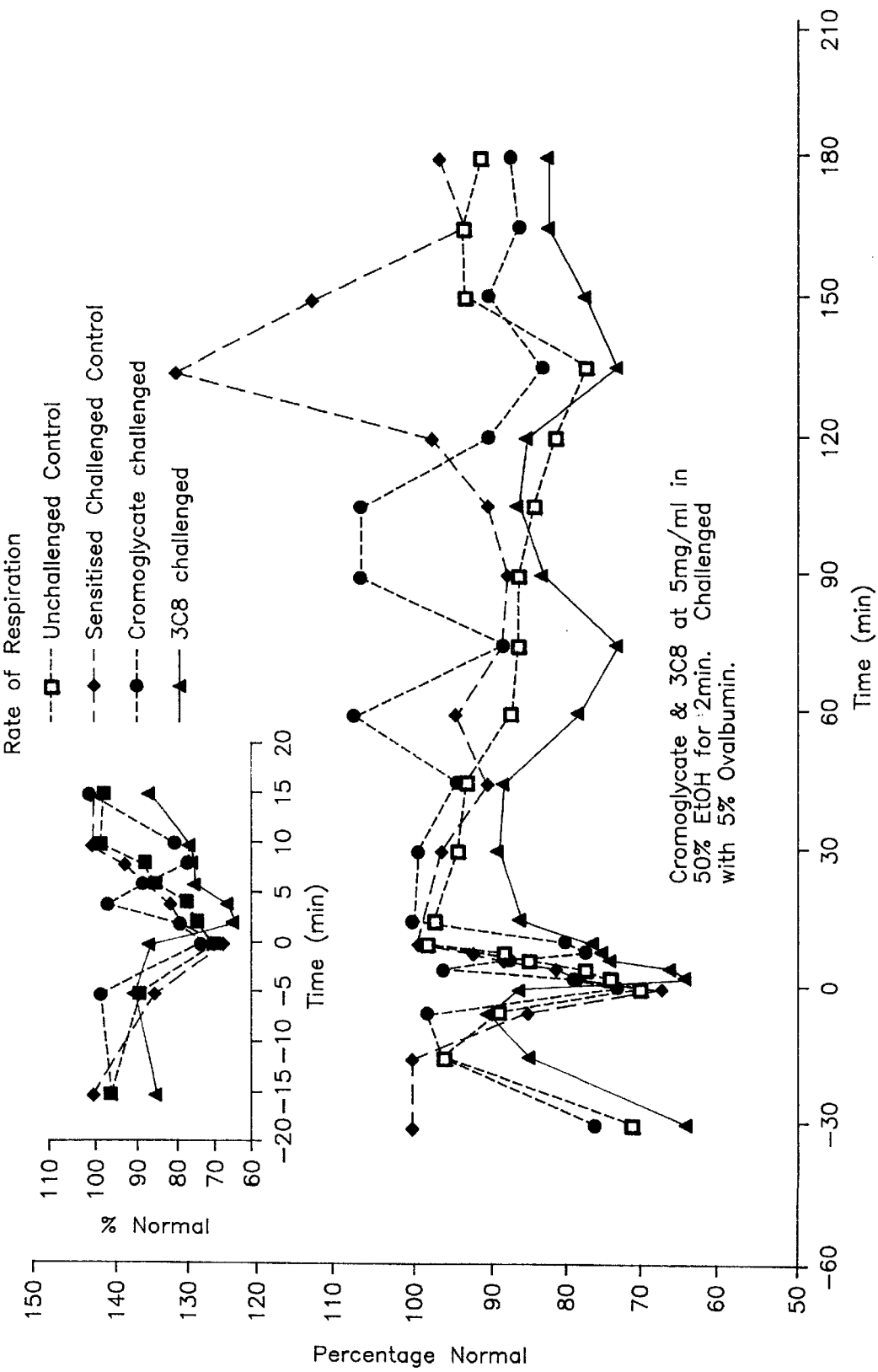

This Application is a continuation of PCT/IE96/00080 filed Dec. 6, 1996.

The invention relates to indane compounds, processes for their production, compositions containing them and their pharmacological use.

According to the invention there is provided a pharmaceutical composition comprising a compound of any of the formulae:

1

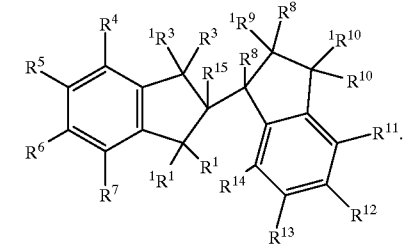

2

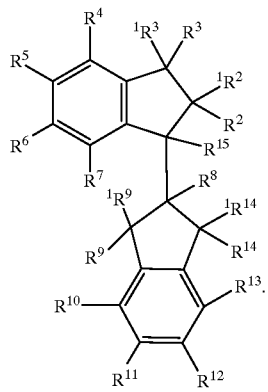

3

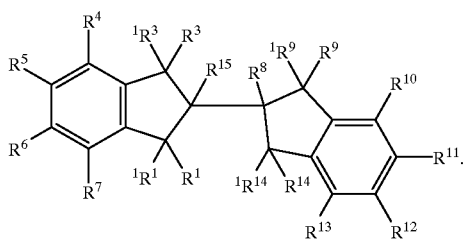

4

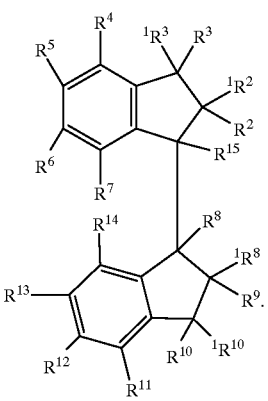

wherein
in Formulae 1 and 3
$R^1$ and $R^3$ to $R^{15}$
in Formulae 2 and 4
$R^2$ to $R^{15}$
are selected from one or more of the same or different of:
H, halo, hydroxy, alkoxy, aryloxy, acetoxy, carboxy, alkyl carbonyl, hydro carbonyl, amino, amido, alkylamino, hydroxylamino, amine oxide groups, azo groups, cyano, hydrazino groups, hydrazide groups, hydrazone groups, imide groups, iminoether groups, ureyl groups, oxime, nitro, nitrate, nitrite, nitroso groups, nitrile, heterocyclic groups containing hetero atoms selected from one or more of N, O and/or S, aralkyl groups, mono and polybenzoid aryl groups, substituted aryl groups, thiol, thioureyl, phenylthiol groups, sulphonic acid groups, sulphoxide groups, sulphone groups, alkyl containing 1 to 10 carbon atoms or cycloalkyl groups containing 3 to 8 carbon atoms which may be saturated or unsaturated, substituted akyl or cycloalkyl groups which may be saturated or unsaturated
in Formulae 1 and 4
any of: $R^8$ and $R^{15}$; or $R^8$ and $R^9$ may together represent a double bond
in Formulae 2 and 3
any of: $R^8$ and $R^{15}$; or $R^8$ and $R^9$; or $R^8$ and $R^{14}$ may together represent a double bond
in Formula 1
any one or more of $R^1$, $^1R^1$; $R^3$, $^1R^3$; $R^9$, $^1R^9$, $R^{10}$, $^1R^{10}$ may together represent oxo;
in Formula 2
any one or more of $R^2$, $^1R^2$; $R^3$, $^1R^3$; $R^9$, $^1R^9$; $R^{14}$, $^1R^{14}$; may together represent oxo;
in Formula 3
any one or more of $R^1$, $^1R^1$; $R^3$, $^1R^3$; $R^9$, $^1R^9$; $R^{14}$, $^1R^{14}$; may together represent oxo;
in Formula 4
any one or more of $R^2$, $^1R^2$; $R^3$, $^1R^3$; $R^9$, $^1R^9$; $R^{10}$, $^1R^{10}$; may together represent oxo;
pharmacogically acceptable salts, esters, amides, solvates and isomers thereof.

The invention also provides compounds of Formulae 1 to 4 per se as defined above.
In Formula 1
$R^1$, $^1R^1$, $R^3$, $^1R^3$; and $R^{10}$, $^1R^{10}$ do not all together represent oxo.
In Formula 2
$R^3$, $^1R^3$; $R^9$, $^1R^9$; and $R^{14}$, $^1R^{14}$ do not all together represent oxo.
In Formula 3
any three or all four of $R^1$, $^1R^1$; $R^3$, $^1R^3$, $^1R^9$ $^1R^9$; and $R^{14}$, $^1R^{14}$ do not together represent oxo.
In Formula 4
any three or all four of $R^1$, $^1R^1$; $R^3$, $^1R^3$; $R^9$, $^1R^9$; and $R^{14}$, $^1R^{14}$ do not together represent oxo.

In one embodiment of the invention the alkyl or cycloalkyl are substituted with one or more of the same or different of halo, oxo, hydroxy, alkoxy, aryloxy, acetoxy, carboxy, carbonyl, amino, amido, alkylamino, hydroxyamino, amine oxide groups, azo groups, cyano, hydrazino groups, hydrazide groups, hydrazone groups, imide groups, imino ether groups, ureyl groups, oxime, nitro, nitrate, nitrite, nitroso groups, nitrile, heterocyclic groups, aralkyl groups, mono and polybenzoid aryl groups, substituted aryl groups, thiol, thioureyl, phenyl thiol groups, sulphonic acid groups, sulphoxide groups and sulphone groups.

In one embodiment of the invention the heterocyclic groups are selected from heteroatoms containing one or more of N, O or S.

Preferably in Formula 1 $R^3$ to $R^7$ and preferably also $R^{10}$ to $R^{14}$ are hydrogen.

In Formula 1 preferred particularly because of pharmacological activity as mast cell stabilisers are those compounds in which:

$R^8$ and $R^9$ together represent a double bond;
$R^1$, $^1R^1$ represent H, OH; and
$R^{15}$ is benzyl.

Preferably in Formula 2 $R^3$ to $R^7$ and also preferably $R^{10}$ to $R^{13}$ are hydrogen.

In Formula 2 preferred particularly because of pharmacological activity as mast cell stablilisers are those compounds in which:

$R^8$ and $R^9$ or $R^8$ and $R^{14}$ together represent a double bond;
$R^2$, $^1R^2$ represent H, OH; and
$R^{15}$ is benzyl.

Preferably in Formula 3 $R^4$ to $R^7$ and preferably also $R^{10}$ to $R^{13}$ represent hydrogen.

In Formula 3 preferred particularly because of pharmacological activity as mast cell stabilisers and for anti-inflammatory activity are those compounds in which:

$R^8$ and $R^9$ or $R^8$ and $R^{14}$ together represent a double bond;
$R^1$, $^1R^1$ represents H, OH; and
$R^{15}$ is benzyl.

Preferably in Formula 4 $R^4$ to $R^7$ and also preferably $R^{10}$ to $R^{14}$ represent hydrogen.

The invention relates to the compounds above for use as smooth muscle relaxants and/or as mast cell stabilising agents and/or as anti-inflammatory agents.

The invention also relates to the use of the compounds in methods of prophylaxis or treatment particularly to achieve smooth muscle relaxant activity and/or mast cell stabilising activity and/or anti-inflammatory activity.

The invention also relates to the compounds per se given in Appendix 2.

The invention also provides various processes for preparing the indane dimers as outlined in the claims. These processes are described in more detail below.

General Reaction Procedures

1. Aluminium Tri-tert-butoxide Method for Synthesis of Indan-1-one

Indan-1-one and toluene was placed in a 250 ml round bottomed flask and the solution was dried by azeotropic distillation. To this solution was added Aluminium tri-tert-butoxide and the reaction mixture was allowed to reflux for 1 hour. An additional amount of Aluminium tri-tert-butoxide was added and the reaction was left to reflux for a further 30 mins.

The reaction mixture was cooled before being poured onto water. The product was extracted using ether and dried over sodium sulphate. On evaporation of the solvent the crude product was purified by flash column chromatography (eluent: petroleum ether:ether, 9:1). After evaporation of the eluent the product was obtained as a crystalline solid.

This procedure is particularly applicable for the synthesis of 2-(1'-Indanylidene)-1-indanone using 1-indanone as starting material.

2. Lithium diisopropylamide (LDA) Alkylation reaction

LDA based alkylations of α-β enone dimer has proven to have been an excellent route to α alkyl-β, α enone dimers.

Generally, the experimental procedure was as follows. A three necked 100 ml round bottomed flask was oven dried and fitted with a septum and a nitrogen inlet line. The flask was then evacuated and heated with a heat gun to dry. To this flask which was filled with nitrogen was added the required dimer in dry THF. The solution was cooled to −78° C. with a liquid nitrogen/ethyl acetate bath and lithium diisopropylamide (LDA) in THF/heptane/ethylbenzene was added. After stirring for 10 minutes at −78° C., the desired organic halide was added and the solution was allowed to warm to room temperature for 3 hours under a nitrogen atmosphere. To this solution was added ether and aqueous ammonium chloride solution. The organic layer was isolated and the aqueous layer was extracted with ether. The combined organic extracts were dried over sodium sulphate and on evaporation of the solvent afforded an oil. The crude product was purified by flash column chromatography.

3. Formation of Dimers in Families 1 to 4 by Coupling of a Silyl Enol Ether of an Indonone with a Dimethyl Acetal or Cyclic Acetal of the Same or Different Indanone This coupling procedure was primarily developed to couple two different indanones together. However, this methodology was also successful for the coupling of the same indanone together. Generally, the experimental procedure was as follows.

To a stirred solution of the silyl emol ether of a particular indanone together and the corresponding dimethyl acetal of the same or different indanone in dichloromethane at −78° C., was added a catalytic amount of TMS triflate. The solution was left stirring at −78° C. for 3 hours and then allowed to reach −50° C. for 1 hour. To this solution was then added a 5% solution of sodium bicarbonate. The organic layer was isolated and the aqueous layer extracted with dichloromethane. The combine organic layers were dried with sodium sulphate. After evaporation of the solvent, the crude product was passed through a plug of silica, eluting with petroleum ether 100% grading to petroleum ether:ethyl acetate, 100:4. After evaporation of the eluent the product was obtained. Same procedure for the coupling of a silyl enol ether of an Indonone derivative with a cyclic-ketal of 1-indanone derivative.

4. Elimination of Methanol to Form α,β-unsaturated Ketone

This procedure was primarily designed to synthesise α,β-unsaturated ketones from the resulting methyl ethers dimers generated from the coupling of the silyl enol ethers and dimethyl acetals of different indanones. The reaction procedure was as follows.

The required dimer was dissolved in methanol and DCM, 3:1 and to this stirring solution was added triflic acid. The reaction mixture was allowed to reflux for 1 hour, after which time a precipitate formed. The solution was then cooled in an ice bath, filtered and the solid which was the respective α,β-unsaturated ketone was dried.

5. Coupling of 3-Bromoindan-1-one to the Silyl Enol Ether of Indanones

This procedure was particularly designed to couple a multitude of indanones to the 3 position of indane-1-one. None of the other synthesis that were described above to couple indanones together appeared to allow for this transformation. The success of this coupling was primarily governed by the choice of Lewis acid (TMS triflate was used) because of the presence of the potentially reactive carbonyl functional group on the 3-bromo indanone in the presence of the Lewis acids. The reaction scheme for preparing one compound of the invention is as follows:

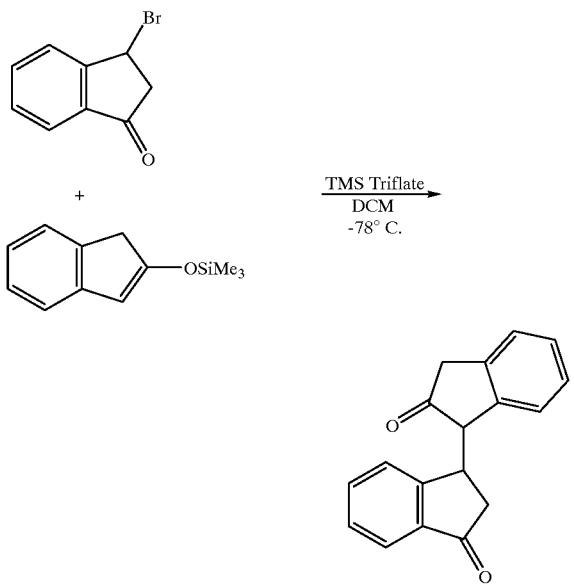

To a stirred solution of the silyl enol ether of an indanone and a 3-bromo indane-1-one derivative in dichloromethane at −78° C., was added a catalytic amount of TMS triflate. The solution was left stirring at −78° C. for 10 mins and at room temperature for 3 hours. To this solution was then added solid sodium bicarbonate (approx. 2 g) and the solution was stirred rapidly for 10 minutes. The solution was then filtered and the filtrate was evaporated to leave a mobile oil, which was passed through a plug of silica, eluting with petroleum ether:ethyl acetate 9:2. After evaporation of the eluent, the product was obtained.

6. Reduction of Dimers with 10% Palladium on Carbon

This procedure is particularly applicable to the reduction of the carbon-carbon double bonds of β, α enone dimers in families 1,2,3 and 4. In the case of α,β-unsaturated ketone indane dimers, this method of reduction always results in both the reduction of the carbon-carbon double bond and the carbonyl of the α-β-unsaturated system. The reduction procedure was as follows.

The required dimer was dissolved in ethanol and ethyl acetate. To this, 10% palladium over activated charcoal (catalytic quantities) was added and the reaction was stirred under hydrogen for 2 hours. The catalyst was removed by filtration. Evaporation of the solvent at reduced pressure afforded the crude product. The crude product was purified by flash column chromatography.

7. Reduction of Dimers with 10% Palladium on Carbon and Concentrated aq HCl

This procedure is particularly applicable to both the reduction of the β, α carbon-carbon double bond and the ketone functional group. The reduction procedure was as follows.

The required dimer was dissolved in distilled ethanol and ethyl acetate. To this, concentrated aqueous HCl 37% solution was added together with water and 10% palladium over activated charcoal (catalytic quantities) and the mixture was stirred under hydrogen for 24 hours.

The catalyst was removed by filtration and the product was extracted into ethyl acetate (3×20 ml). The crude product was purified by flash column chromatography.

8. Sodium Borohydride Reduction of Dimers

This reduction is particularly applicable to the reduction of the ketone functional group of compounds in families 1–4. The reduction procedure was as follows.

The required dimer was dissolved in ethanol and sodium borohydride was added to the reaction in small portions over 10 mins. The reaction was then stirred at room temperature for 3 hours. The reaction mixture was poured onto water (20 ml) and extracted into diethyl ether (3×20 ml). Flash column chromatography over silica gel afforded the product.

9. Reduction of Dimers by Huang-Minlon Modification Reaction Hydrazine Hydrate Reaction This reduction procedure is particularly applicable to the reduction of the ketone functional group in the case of β, α enones. The reduction procedure was as follows.

The required dimer was dispersed in ethylene glycol. Hydrazine hydrate was added along with sodium hydroxide. The reaction was stirred at reflux for 24 hours. The reaction mixture was then cooled to room temperature and water was added and the product was extracted with ethyl acetate. The organic layer was isolated and dried over anhydrous sodium sulphate. Flash column chromatography was used to afford the pure product.

10. Cyanoborohydride Reduction of Dimers

This reduction procedure is particularly applicable to the reduction of the ketone functional group of compounds in families 1–4. The reduction is as follows.

The required dimer was dispersed in 1,2-dichloroethane at room temperature. To this solution was added solid zinc iodide and sodium cyanborohydride. The reaction was stirred at reflux for 20 hours. The product was added to water and extracted into ethyl acetate. Flash column chromatography (eluent: petroleum ether:ethyl acetate, 9:1) was used to isolate the pure product.

11. Reduction or Isomerisation of the α,β-unsaturated Double Bond in Dimers with 5% Palladium on Carbon This procedure is particularly applicable to the reduction of the double bond in the case of α,β-unsaturated ketones.

The required dimer was dispersed in ethanol and ethyl acetate and to this was added 5% palladium on carbon. The mixture was stirred under hydrogen for 14 hours. The palladium was removed by filtration and the solvent was removed to afford the crude reaction product. Flash column chromatography afforded the required product.

12. Wilkinsons Reduction of Dimers

This method of reduction was particularly effective for the selective reduction of a double bond on $R^{15}$ without reducing the $R^8$–$R^9$ double bond in families 1 to 4. The reduction procedure was as follows.

The required dimer was dissolved in ethanol and ethyl acetate. To this stirring solution Wilkinsons catalyst was added. The reaction was then stirred under hydrogen for 20 hours. The product was partitioned between ethyl acetate and water and the organic layer was isolated and dried with $Na_2SO_4$. The crude product was purified by flash column chromatography to yield the required product.

13. Hydrolysis of an Ester Dimers in Families 1 to 4

The required ester was dissolved in a solution of 1.45 M NaOH in THF:MeOH:$H_2O$ (6:3:2), which was then refluxed. After 20 minutes, TLC showed that the hydrolysis of the ester was complete. After cooling the reaction mixture, a saturated solution of aqueous ammonium chloride, aqueous HCl (2M) and ether was added. The organic layer was isolated and the aqueous layer was extracted with ether. The combined organic extracts were dried with $Na_2SO_4$ and filtered. Evaporation of the solvent, left the acid.

14. Oxime Synthesis

This procedure is particularly applicable for the synthesis of oxime derivatives of ketonic indane dimers which have hydrogens to the ketone. Generally the procedure was as follows.

The ketonic indanone dimer was dissolved in a solution of methanol:pyridine (4:1) and to this solution was then added hydroxylamine hydrochloride. Depending on the specific ketonic indan dimer, the reaction was carried out either at room temperature or at reflux conditions.

15. O-alkylation of the Oxime

This procedure is particularly applicable to O-alkylation of the oxime derivatives synthesised. Generally the procedure was as follows.

A solution of the oxime indane dimer was dissolved in ether:tert-butanol 3:1. Benzyl bromide was generally used as the alkylating reagent and it was added to the reaction mixture. Potassium tert-butoxide 1 eq. was added dropwise to this solution at room temperature. After workup using aqueous ammonium chloride and ether the desired oxime ether was isolated after chromatography.

16. α-alkylation of O-benzyl Oximes

This procedure is particularly applicable to the α-alkylation of oxime ether derivatives.

The procedure was as follows.

A solution of the oxime ether was dissolved in dry ether and cooled to −78° C. To this solution was added n-butyl lithium, followed by benzyl bromide in excess. the reaction was generally quenched with water, the product extracted with ether and purified by flash column chromatography.

17. Sulfonylation of 2-indanol Dimers

This procedure is particularly applicable to sulfonylation of hydroxyl groups of 2-indanol dimers. The required hydroxylated dimer was dissolved in dichloromethane and to this solution was added methanesulfonyl chloride and N,N-diisopropylethyl amine dropwise. After stirring for 15 mins at 0° C., the reaction mixture was normally partitioned between DM and aqueous NaHCO₃, the organic layer was isolated washed with water, 2M aqueous HCl and finally water. Final purification of the products was by flash column chromatography.

18. Acetylation of the Hydroxyl Indan-dimers

Generally the procedure was to dissolve the compound for acetylation in DCM and to use acetic anhydride as the acetylating reagent with triethylamine as tertiary base and DMAP as the acylation catalyst.

19. β-methoxy Carbonyl Compounds Transformation to α-alkyl and β, -enones

The β-methoxy carbonyl compound was dissolved in ether: ᵗbutanol (5:1) and to this the desired alkylation agent was added. To a stirring solution potassium tert-butoxide was added dropwise over a period of 30 mins. The reaction was allowed to stir at room temperature for 24 hours. An aqueous solution of ammonium chloride was added and the product was extracted into ether. The crude reaction mixture was then passed through a column of flash silica, to yield the desired product.

20. Alkylation of an α, β-enone

The required dimer was dissolved in ether: ᵗbutanol (5:1) and to this the desired alkylation agent was added. To a stirring solution potassium tert-butoxide was added dropwise over a period of 30 mins. The reaction was allowed to stir at room temperature for 24 hours. An aqueous solution of ammonium chloride was added and the product was extracted into ether. The crude reaction mixture was then passed through a column of flash silica, to yield the desired product.

Synthesis of 1C1
Potassium Tert-butoxide Method

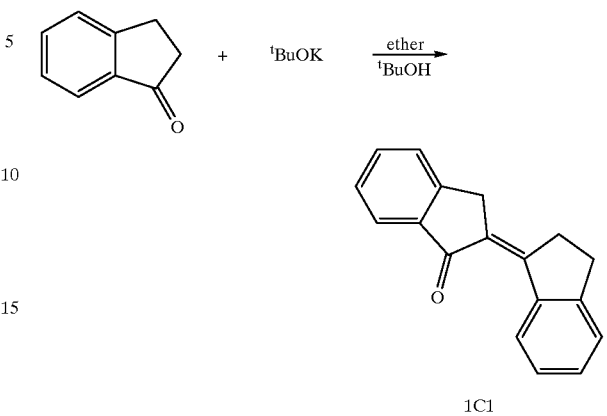

1C1

Potassium tert butoxide (4.25 g, 37 mmol) in ᵗbutanol (125 ml) and ether (10 ml) were added dropwise over 20 minutes, to a stirring solution of indan-1-one (5.0 g, 37 mmol) in ether (20 ml) and ᵗbutanol (5 ml). The reaction mixture was then left stirring overnight.

The crude product was partitioned between ethyl acetate and saturated aqueous ammonium chloride. The organic layer was isolated and the aqueous phase was re-extracted with ethyl acetate. The organic layers were combined and dried over sodium sulphate. On evaporation of the solvent the crude product was obtained. Flash chromatography was used to purify the required product (eluent: petroleum ether (b.p. 40–60° C.):ethyl acetate, 9:1). On recrystallisation with ether 1C1 was obtained as a yellow solid. (Yield 20%).

Low resolution mass spectra: Found M⁺246. Required M⁺246.

$^1$H NMR (CDCl₃, 300 MHz) $\delta_H$ 3.11 (2H, t, J=6 Hz, C$\underline{H}_2$), 3.54 (2H, m, C$\underline{H}_2$), 3.98 (2H, s, C$\underline{H}_2$), 7.53 (6H, m, 6×Ar—$\underline{H}$), 7.79 (2H, m, 2×Ar—$\underline{H}$).

$^{13}$C NMR (CDCl₃, 75.47 MHz) $\delta_C$ 30.9, 31.5, 33.0 (3× $\underline{C}$H₂), 123.5, 125.7, 125.9 (3×Ar—$\underline{C}$H), 125.9 (C=C), 126.2, 126.8, 127.2, 130.4, 133.5 (5×Ar—$\underline{C}$H), 139.5, 140.8, 148.5, 151.7, 154.9 (1×c=c and 4×AR—$\underline{C}$), 195.1 ($\underline{C}$=O).

Alternative Synthesis of 1C1
Aluminium Tri-tert-butoxide Method

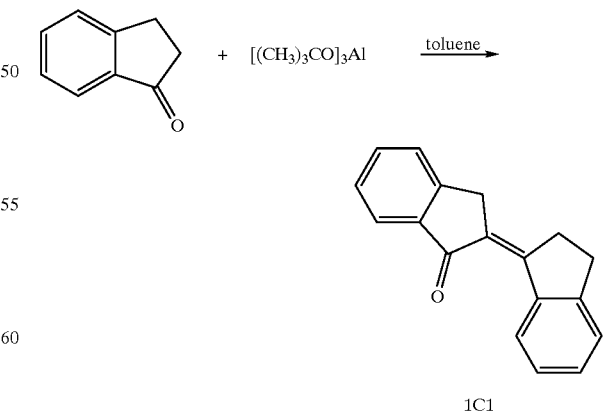

1C1

Indan-1-one (5.0 g, 37 mmol) and toluene (80 ml) were placed in a 250 ml round bottomed flask and the solution was dried by azeotropic distillation. To this solution was added Aluminium tri-tert-butoxide (4.7 g, 19 mmol) and the reaction mixture was allowed to reflux for 1 hour. An additional amount of Aluminium tri-tert-butoxide (2.3 g, 9.0 mmol) was added and the reaction was left to reflux for a further 30 minutes.

The reaction mixture was cooled before being poured onto water. The product was extracted using ether and dried over sodium sulphate. On evaporation of the solvent the crude product was purified by flash column chromatography (eluent: petroleum ether:ether, 9:1). After evaporation of the eluent 1C1 was obtained as a yellow crystalline solid, 48% yield.

Low resolution mass spectra: Found M$^+$246. Required M$^+$246.

$^1$H NMR (CDCl$_3$, 300 MHz) $\delta_H$ 3.11 (2H, t, J=6 Hz, C$\underline{H}_2$), 3.54 (2H, m, C$\underline{H}_2$), 3.98 (2H, s, C$\underline{H}_2$), 7.53 (6H, m, 6×Ar—$\underline{H}$), 7.79 (2H, m, 2×Ar—$\underline{H}$).

$^{13}$C NMR (CDCl$_3$, 75.47 MHz) $\delta_C$ 30.9, 31.5, 33.0 (3× $\underline{C}$H$_2$), 123.5, 125.7, 125.9 (3×Ar—$\underline{C}$H), 125.9 (C=C), 126.2, 126.8, 127.2, 130.4, 133.5 (5×Ar—$\underline{C}$H), 139.5, 140.8, 148.7, 151.7, 154.9 (4×Ar—$\underline{C}$, and 1×$\underline{C}$=C), 195.1 ($\underline{C}$=O).

Synthesis of 1C2

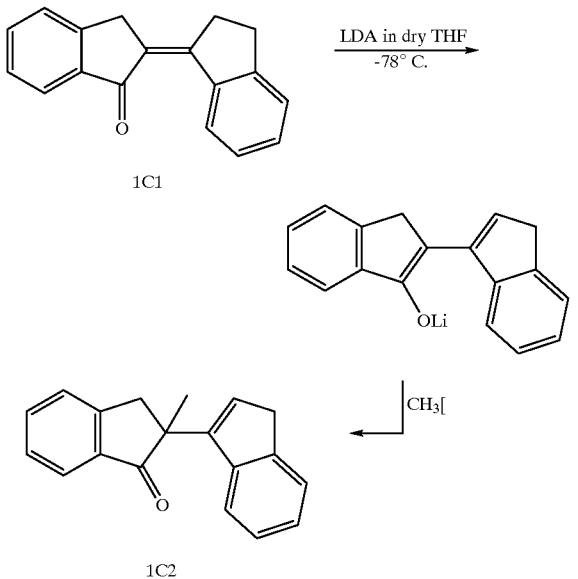

A three necked 100 ml round bottomed flask was oven dried and fitted with a septum and a nitrogen inlet line. The flask was then evacuated and heated with a heat gun to dry. To this flask, which was filled with nitrogen was added indan-1-one dimer 1C1 (500 mg, 2.0 mmol) in dry THF (25 ml). The solution was cooled to −78° C. with a liquid nitrogen/ethyl acetate bath and lithium diisopropylamide (LDA) in THF/heptane/ethylbenzene (1.0 ml of 2M solution of LDA) was added. After stirring for 10 minutes at −78° C., iodomethane (1.14 g, 8.0 mmol, 4 equivalents) was added and the solution was allowed to warm to room temperature for 3 hours under vacuum and in a nitrogen atmosphere.

To this solution was added ether (30 ml) and ammonium chloride solution (30 ml). The organic layer was isolated and the aqueous layer was extracted with ether (2×30 ml). The combined organic extracts were dried over sodium sulphate and on evaporation of the solvent afforded an oil. The crude product was purified by flash column chromatography (eluent: petroleum ether b.p. 40–60° C.:ethyl acetate, 9:1), to yield 1C2 m.p.: 112–114° C.

IR (KBr)$_{max}$: 2361.2, 1715.1, 1606.9, 1459.7 cm$^{-1}$.

Microanalysis: C$_{19}$H$_{16}$O requires C, 87.69% and H, 6.15%. found: C, 87.54% and H, 6.25%.

Low resolution mass spectra: Found M$^+$260, M$^+$−15=245. Required M$^+$260.

$^1$H NMR (CDCl$_3$, 300 MHz) $\delta_H$ 1.67 (3H, s, C$\underline{H}_3$), 3.20 (1H, d, J=17 Hz, C$\underline{H}$), 3.40 (2H, d, J=2 Hz, C$\underline{H}_2$), 3.69 (1H, d, J=17 Hz, C$\underline{H}$), 6.52 (1H, t, J=2 Hz, C$\underline{H}$), 6.87 (1H, d, J=8 Hz, Ar—$\underline{H}$), 7.15 (2H, m, 2×Ar—$\underline{H}$), 7.48 (3H, m, 3×Ar—$\underline{H}$), 7.68 (1H, m, Ar—$\underline{H}$), 7.92 (1H, d, J=8 Hz, Ar—$\underline{H}$).

$^{13}$C NMR (CDCl$_3$, 75.47 MHz) $\delta_C$ 23.9 ($\underline{C}$H$_3$), 37.6, 41.2 (2×$\underline{C}$H$_2$), 50.5 (CO$\underline{C}$(CH$_2$) (CH$_3$)), 119.8, 124.1, 124.6, 124.8, 125.9, 126.8, 127.7, 130.1, 135.2, (8×Ar—$\underline{C}$H & 1×C=$\underline{C}$H), 135.6, 143.0, 144.9, 145.8, 152.3 (4×Ar—$\underline{C}$ & $\underline{C}$=CH), 208.6 ($\underline{C}$=O).

Synthesis of 1C2
Potassium Tert-butoxide Method

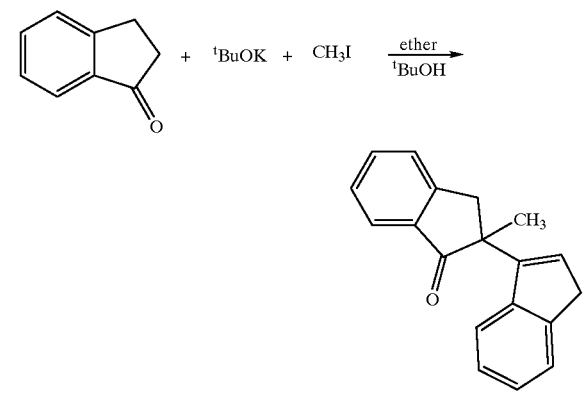

To a three necked round bottomed flask was added indan-1-one (10.0 g, 75 mmol) which was dissolved in ether (100 ml) and $^t$butanol (20 ml). To this, iodomethane (4.72 ml, 75 mmol) in ether (50 ml) and potassium tert-butoxide (8.49 g, 75 mmol) in $^t$butanol (150 ml) were added dropwise at equal rates. The reaction mixture was stirred at reflux for 2 hours.

The solution was allowed to cool and the mixture was partitioned between ethyl acetate and aqueous ammonium chloride (1:1 300 ml). The organic layer was extracted and the aqueous phase re-extracted with ethyl acetate (2×50 ml). The combined organic layers were dried over sodium sulphate. On evaporation of the solvent the crude product was obtained. Flash column chromatography was used to purify the required product (eluent: petroleum ether (b.p. 40–60° C.):ethyl acetate, 9:1). On isolation of 1C2 it was recrystallised from ether to yield a white solid, (20%).

m.p. 112–114° C.

IR (KBr)$_{max}$: 2361.2, 1715.1, 1606.9, 1459.7 cm$^{-1}$.

Microanalysis: C$_{19}$H$_{16}$O requires C, 87.69% and H, 6.15%. found: C, 87.54% and H, 6.25%.

Low resolution mass spectra: Found M$^+$260, M$^+$−15=245. Required M$^+$260.

$^1$H NMR (CDCl$_3$, 300 MHz) $\delta_H$ 1.67 (3H, s, C$\underline{H}_3$), 3.20 (1H, d, J=17 Hz, C$\underline{H}$), 3.40 (2H, d, J=2 Hz, C$\underline{H}_2$), 3.69 (1H, d, J=17 Hz, C$\underline{H}$), 6.52 (1H, t, J=2 Hz, C$\underline{H}$), 6.87 (1H, d, J=8 Hz, Ar—$\underline{H}$), 7.15 (2H, m, 2×Ar—$\underline{H}$), 7.48 (3H, m, 3×Ar—$\underline{H}$), 7.68 (1H, m, Ar—$\underline{H}$), 7.92 (1H, d, J=8 Hz, Ar—$\underline{H}$).

$^{13}$C NMR (CDCl$_3$, 75.47 MHz) $\delta_C$ 23.9 ($\underline{C}$H$_3$), 37.6, 41.2 (2×$\underline{C}$H$_2$), 50.5 (CO$\underline{C}$(CH$_2$) (CH$_3$)), 119.8, 124.1, 124.6, 124.8, 125.9, 126.8, 127.7, 130.1, 135.2, (8×Ar—$\underline{C}$H &

1×C=$\underline{C}$H), 135.6, 143.0, 144.9, 145.8, 152.3 (4×Ar—$\underline{C}$ & $\underline{C}$=CH), 208.6 ($\underline{C}$=O).

Synthesis of 1C3
10% Palladium on Carbon Reduction

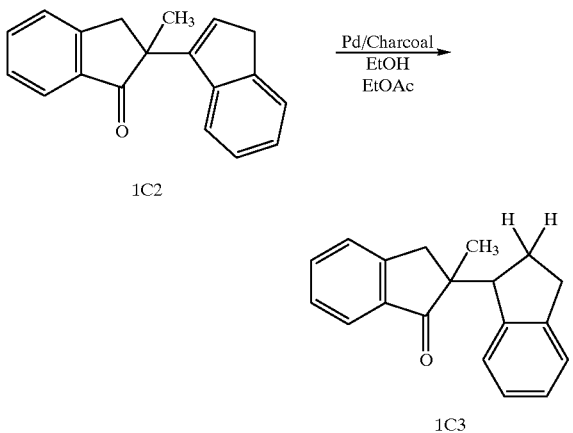

1C2 (1.0 g, 3.8 mmol) was dissolved in ethanol (20 ml) and ethyl acetate (10 ml). To this 10% palladium over activated charcoal (catalytic quantities) was added and the reaction was stirred under hydrogen for 2 hours. The catalyst was removed by filtration. Evaporation of the solvent at reduced pressure afforded a clear oil, which was recrystallised from petroleum ether (b.p. 40–60° C.) as a white solid, (0.76 g, 76.34%). This white solid was found to be a mixture of diastereomers (1C3).

M.p. 88–90° C.

IR (film)$_{max}$: 1709.8 cm$^{-1}$ (C=O), 1606.8 cm$^{-1}$ (C=C).

Where distinguishable the values for the minor diastereomeric mixture are itallised.

$^1$H NMR (CDCl$_3$, 300 MHz) $\delta_H$ 1.46 (3H, s, C$\underline{H}_3$), 1.45, 1.90, 2.10 & 2.30 (2H, 4×m, CHC$\underline{H}_2$), 2.63 & 2.97 (2H, dd, J=18, 102.1 Hz, CC$\underline{H}_2$), 2.79 (2H, m, CHCH$_2$C$\underline{H}_2$), 3.65, 3.84 (1H, 2×m, C$\underline{H}$CH$_2$CH$_2$), 6.73 & 6.99 (1H, 2×br.m, 1×Ar—$\underline{H}$), 7.30 (5H, br m, 5×Ar—$\underline{H}$), 7.56 (1H, m, 1×Ar—$\underline{H}$), 7.78, 7.83 (1H, dd, 1×Ar—$\underline{H}$).

$^{13}$C NMR (CDCl$_3$, 75.47 MHz) $\delta_C$ 24.4, 24.6 ($\underline{C}$H$_3$), 29.0, 28.3, 31.8, 31.2, 37.6, 36.8 (3×$\underline{C}$H$_2$), 50.7, 50.6 ($\underline{C}$H), 52.9, 52.6 (q$\underline{C}$), 124.2, 124.8, 125.5, 125.9, 126.4, 126.8, 127.4, 134.8 (Ar—$\underline{C}$H), 136.2, 144.2, 145.0, 153.4 (Ar—$\underline{C}$), 210.9, 211.0 (C=O).

10% Palladium on Carbon Reduction
Synthesis of 1C4

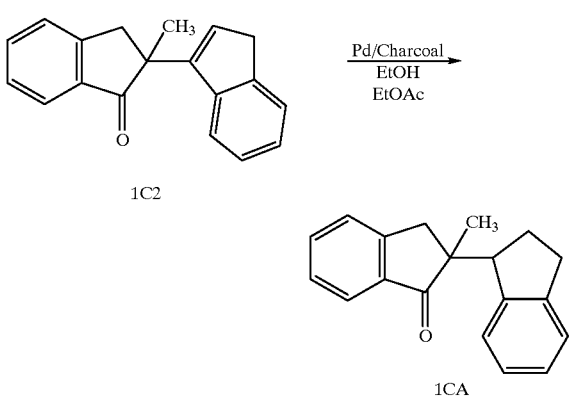

activated charcoal (catalytic quantities) was added and the reaction was stirred under hydrogen for 2 hours. The catalyst was removed by filtration. Evaporation of the solvent at reduced pressure afforded a clear oil, which was recrystallised from diethyl ether and petroleum ether (b.p. 40–60° C.) as a white solid, 0.76 g, 76.34%. This white solid was found to be a mixture of diasteriomers.

M.p. 88–90° C.

IR (film)$_{max}$: 1709.8 cm$^{-1}$ (C=O), 1606.8 cm$^{-1}$ (C=C).

Where distinguishable the values for the minor diasteriomer are italized.

$^1$H NMR (CDCl$_3$, 300 MHz) $\delta_H$ 1.46 (3H, s, C$\underline{H}_3$), 1.45, 1.90, 2.10 & 2.30 (2H, 4×m, CHC$\underline{H}_2$CH$_2$), 2.68 & 2.98 (2H, dd, J=17.8 Hz, CC$\underline{H}_2$), 2.79 (2H, m, CHCH$_2$C$\underline{H}_2$), 3.65, 3.85 (1H, m, C$\underline{H}$CH$_2$CH$_2$), 6.75 & 6.96 (1H, br.m & t respectively, 1×Ar—$\underline{H}$), 7.30 (5H, br m, 5×Ar—$\underline{H}$), 7.56 (1H, m, 1×Ar—$\underline{H}$), 7.78, 7.83 (1H, dd, 1×Ar—$\underline{H}$).

13C NMR (CDCl$_3$, 75.47 MHz) $\delta_C$ 24.4, 24.6 ($\underline{C}$H$_3$), 29.0, 28.3, 31.8, 31.2, 37.6, 36.8 (3×$\underline{C}$H$_2$), 50.7, 50.6 ($\underline{C}$H), 52.9, 52.6 (q$\underline{C}$), 124.2, 124.8, 125.5, 125.9, 126.4, 126.8, 127.4, 134.8 (Ar—$\underline{C}$H), 136.2, 144.2, 145.0, 153.4 (Ar—$\underline{C}$), 210.9, 211.0 (C=O).

10% Palladium on Carbon Reduction
Synthesis of 1C4

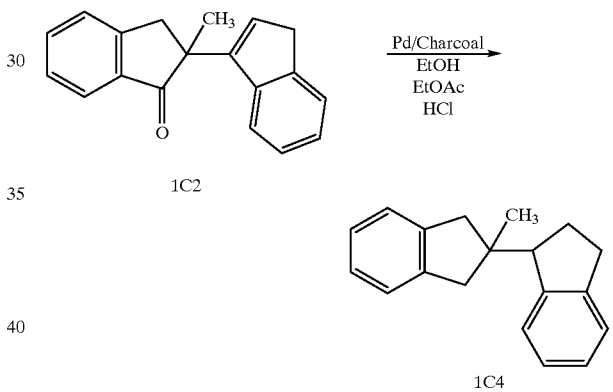

1C2 (100 mg, 0.385 mmol) was dissolved in distilled ethanol (5 ml) and ethyl acetate (1 ml). To this solution concentrated HCl 37% solution (0.2 ml) was added together with water (0.4 ml) and Pd/Charcoal (catalytic quantities) and the mixture was stirred under hydrogen for 24 hours.

The catalyst was removed by filtration and the product was extracted into ethyl acetate (3×20 ml). The crude product was purified by flash column chromatography (eluent: petroleum ether:ethyl acetate, 99:1) to yield 1C4 (84 mg, 89.14%).

$^1$H NMR (CDCl$_3$, 300 MHz) $\delta_H$ 1.52 (3H, s, C$\underline{H}_3$), 2.14 and 2.21 (2H, each m, CHC$\underline{H}_2$CH$_2$), 2.80 and 3.26 (2H, 2×d, J=15.5 Hz, CC$\underline{H}_2$), 3.04 and 3.13 (2H, 2×d, J=15.5 Hz, CC$\underline{H}_2$), 3.11 (2H, m, CHCH$_2$C$\underline{H}_2$), 3.49 (1H, m, C$\underline{H}$CH$_2$CH$_2$), 7.26 (8H, br m, 8×Ar—$\underline{H}$).

$^{13}$C NMR (CDCl$_3$, 75.47 MHz) $\delta_C$ 22.6 ($\underline{C}$H$_3$), 28.6, 31.9, 46.3, 46.5 ($\underline{C}$H$_2$), 55.5 ($\underline{C}$H), 124.5, 124.7, 125.2, 125.8, 125.9, 125.9, 126.4, (Ar—$\underline{C}$H), 142.5, 143.0, 145.1, 145.2 (Ar—$\underline{C}$).

References:

C. M. Wong, D. Popies, R. Schwerk and J. Te Raa.
Can. J. Chem. Vol 49, (1971), 2714

Sodium Borohydride Reduction
Synthesis of 1C5

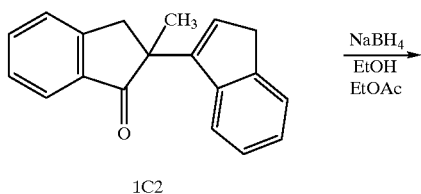

1C2 (530 mg, 2.04 mmol) was dissolved in ethanol (10 ml) and sodium borohydride (0.1 g, 2.63 mmol) was added to the reaction in small portions over 10 minutes. The reaction was stirred at room temperature for 3 hour. The reaction mixture was poured onto water (20 ml) and extracted into diethyl ether (3×20 ml). Flash column chromatography over silica gel (eluent: petroleum ether (b.p. 40–60° C.):ethyl acetate, 98:2) afforded the product 1C5 as a clear oil 396 mg, 74.15%. It was found that the product was obtained as a mixture of diastereomers.

IR (KBr)$_{max}$: 3429.8 cm$^{-1}$.

Where distinguishable the values for the minor diastereomer are italized.

$^1$H NMR (CDCl$_3$, 300 MHz) $\delta_H$ 1.44, 1.47 (3H, d, C$\underline{H}_3$), 3.00 & 3.84, (1H, 2×d, J=15.5 Hz, C$\underline{H}$ of CH$_2$), 3.13 & 3.35 (1H, dd, J=15.9 Hz, C$\underline{H}$ of CH$_2$), 3.43 & 3.59 (2H, 2×d, J=2 Hz, 2 Hz, C$\underline{H}_2$), 5.41, 5.67 (1H, 2×s, C$\underline{H}$OH), 6.49, 6.53 (1H, 2×t, J=2 Hz, 2 Hz, C=C$\underline{H}$), 7.40 & 7.78 (6H, m & d respectively, 6×Ar—$\underline{H}$), 7.61 (2H, m, 2×Ar—$\underline{H}$).

$^{13}$C NMR (CDCl$_3$, 75.47 MHz) $\delta_C$ 25.5 (C$\underline{H}_3$), 37.6, 37.9, 43.1, 43.2 (C$\underline{H}_2$), 49.9, 50.2 (q$\underline{C}$), 80.7, 81.6, (C$\underline{H}$OH), 121.1 (C$\underline{H}$), 121.2, 121.6, 124.2, 124.3, 124.4, 124.5, 124.8, 125.1, 125.3, 125.8, 126.1, 126.4, 128.0, 128.6, 128.9, 128.9, 130.8, 138.5, 140.3, 142.8, 143.3, 143.9, 144.0, 145.4, 145.5, 148.2, 150.0, 171.3 (Ar—C$\underline{H}$ & Ar—C & 1×C=CH).

Sodium Borohydride Reduction
Synthesis of 1C6

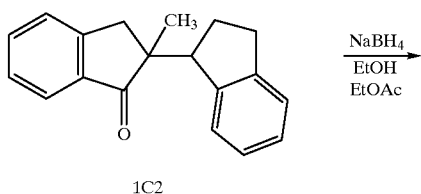

The same method was used as for the synthesis of 1C5. 1C6 was isolated as a mixture of diastereomers 176 mg, 76.24%.

Where distinguishable values for minor diastereomers are italized.

$^1$H NMR (CDCl$_3$, 300 MHz) $\delta_H$ 0.86, 0.94 (3H, 2×s, C$\underline{H}_3$), 2.29–3.54 (6H, br m, C$\underline{H}_2$'s), 5.19, 5.23 (1H, 2×br.s, C$\underline{H}$OH), 7.19–7.39 (8H, m, 8×Ar—$\underline{H}$).

$^{13}$C NMR (CDCl$_3$, 75.47 MHz) $\delta_C$ 15.1, 16.0 (C$\underline{H}_3$), 27.9, 28.9, 31.9, 32.1, 43.6, 43.8 (C$\underline{H}_2$), 52.1 (q$\underline{C}$), 54.5, 54.1 (C$\underline{H}$), 82.5, 82.0 (C$\underline{H}$OH), 123.7, 124.7, 124.9, 125.3, 125.5, 125.8, 125.9, 127.8 (Ar—C$\underline{H}$), 140.2, 144.0, 144.7, 145.2 (Ar—$\underline{C}$)

Hydrazine Hydrate Reaction
Huang-Minlon Modification Reduction Reaction
Synthesis of 1C7

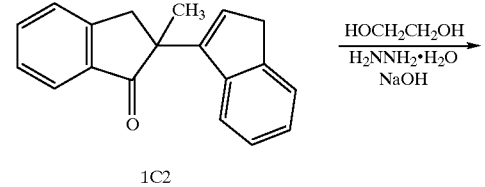

1C2 (100 mg, 0.38 mmol) was dispersed in ethylene glycol (5 ml). Hydrazine hydrate (2.5 ml) was added along with sodium hydroxide (0.2 g). The reaction was stirred at reflux for 24 hours. The reaction mixture was then cooled to room temperature and water (50 ml) was added and the product was extracted with ethyl acetate (3×20 ml). The organic layer was isolated and dried over anhydrous sodium sulphate. Flash column chromatography (eluent: petroleum ether:ethyl acetate 99:1) was used to afford the pure product 1C7 34 mg, 35.58%.

Low resolution mass spectra: Found M$^+$246 Required M$^+$246.

$^1$NMR (CDCl$_3$, 300 MHz) $\delta_H$ 1.53 (3H, s, C$\underline{H}_3$), 3.04 (2H, d, J=15.5 Hz, C$\underline{H}_2$), 3.39 (2H, s, C$\underline{H}_2$), 3.59 (2H, d, J=15.5 Hz, C$\underline{H}_2$), 6.36 (1H, t, CH), 7.28 (6H, br m, 6×Ar—$\underline{H}$), 7.48 (1H, m, 1×Ar—$\underline{H}$), 7.53 (1H, br d, 1×Ar—H).

$^{13}$C nmr (CDCl$_3$, 75.47 MHz) $\delta_C$ 27.5 (C$\underline{H}_3$), 37.4, 45.6, 45.6 (3×C$\underline{H}_2$) 44.2 (q$\underline{C}$), 121.3, 124.1, 124.2, 124.9, 124.9, 125.7, 126.3, 126.3, 126.9 (8×Ar—C$\underline{H}$ and 1×C=C$\underline{H}$) 142.4, 142.4, 144.0, 145.4, 151.7 (4×Ar—$\underline{C}$ and 1×$\underline{C}$=CH).

Cyanoborohydride Reduction Reaction
Synthesis of 1C7
Cyanoborohydride Reduction Reaction

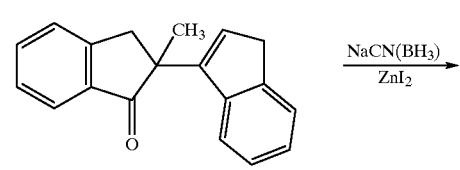

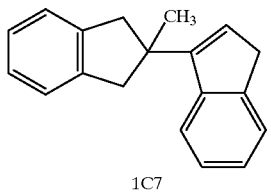

1C7

1C2 (100 mg, 0.38 mmol) was dispersed in 1,2-dichloroethane (5 ml) at room temperature. To this solution was added solid zinc iodide (0.02 g, 0.0625 mmol) and sodium cyanoborohydride (0.2 g, 3.18 mmol). The reaction was stirred at reflux for 20 hours. The product was added to water (15 ml) and extracted into ethyl acetate. Flash column chromatography (eluent: petroleum ether:ethyl acetate 9:1) was used to isolate 1C7, 27 mg, 29.13%.

$^1$H NMR (CDCl$_3$, 300 MHz) $\delta_H$ 1.53 (3H, s, C$\underline{H}_3$), 3.04 (2H, d, J=15.5 Hz, C$\underline{H}_2$), 3.39 (2H, s, C$\underline{H}_2$), 3.59 (2H, s, J=15.5 Hz, C$\underline{H}_2$), 6.36 (1H, t, J=2.1 Hz, C$\underline{H}$), 7.28 (6H, br m, 6×Ar—$\underline{H}$), 7.48 (1H, m, 1×Ar—$\underline{H}$), 7.53 (1H, br d, 1×Ar—$\underline{H}$).

References:
C. K. Lau, Claude Durfresne, P. C. Belanger, S. Pietre and J. Scheigetz.
J. Org. Chem., (1986), 51, 3038–3043.

Synthesis of 1C8

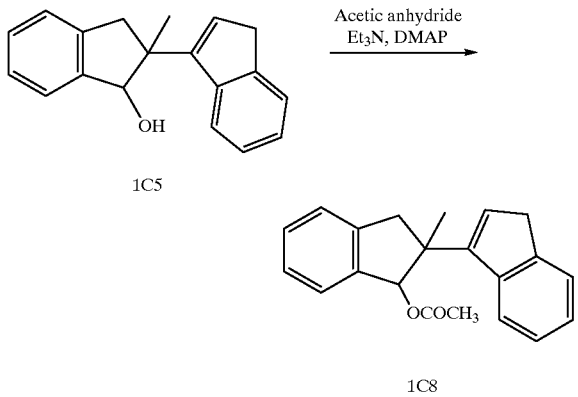

1C5 (100 mg, 0.38 mmol) was dissolved in clean, dry DCM (5 ml). To this solution was added triethylamine (0.2 ml), DMAP (0.1 g) and acetic anhydride (0.35 ml, 10 equivalents). The reaction mixture was stirred at room temperature for 15 minutes and passed through a plug of silica eluting with petroleum spirit (b.p. 40–60° C.):ethyl acetate (8:2) to afford 1C8 (67 mg, 57.7%).

$^1$H NMR (CDCl$_3$, 300 MHz) $\delta$H 1.44 (3H, s, C$\underline{H}_3$), 1.53 (3H, s, OCOC$\underline{H}_3$), 2.91–3.91 (4H, br. m, C$\underline{H}_2$), 6.38 (1H, br s, C=C$\underline{H}$), 6.445 (1H, s, C$\underline{H}$OCOCH$_3$), 7.18–7.58 (8H, m, Ar—H)

$^{13}$CNMR (CDCl$_3$, 75.47 MHz) $\delta_C$ 20.7, 21.1($\underline{C}$H$_3$), 26.1 (OCO$\underline{C}$H$_3$), 37.5, 37.6, 43.7, 43.9 (2×$\underline{C}$H$_2$), 47.9, 48.7 (qC), 81.5, 82.4 ($\underline{C}$HOCOCH$_3$), 121.0, 121.3, 123.8, 124.1, 124.2, 124.4, 124.8, 125.1, 125.2, 125.8, 125.9, 126.7, 126.8, 127.2, 128.4, 128.6, 129.1, 129.3, 140.5, 141.8, 143.5 143.8, 144.8, 145.3, 148.3 (8×Ar—$\underline{C}$H, 4×Ar—$\underline{C}$, 1 each $\underline{C}$=$\underline{C}$H), 170.6 (O$\underline{C}$OCH$_3$)

Synthesis of 1C9

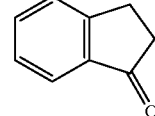 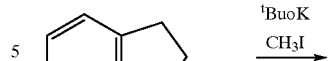

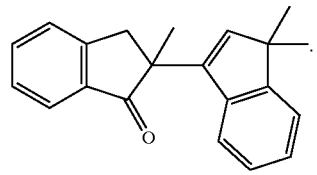

1C9

To stirring solution of indan-1-one (2 g, 0.015 mol) in diethyl ether (40 ml) and t-butanol (20 ml), was added potassium tert-butoxide (1.7 g, 15.2 mmol) in portions. Following the addition of the potassium tert-butoxide, iodomethane (2.13 g, 0.934 ml, 14.6 mmol) was added dropwise and the reaction was stirred at reflux for 2 hours. The reaction was cooled to room temperature and extracted into ethyl acetate. The solvent was evaporated at reduced pressure. Column chromatography over silica gel eluting with petroleum spirit (b.p. 40–60° C.):ethyl acetate (9:1) afforded 1C9 (0.87 g, 39.9%)

$^1$H NMR (CDCl$_3$, 300 MHz) $\delta$H 1.31, 1.34, 1.61 (9H, 3×s, 3×C$\underline{H}_3$), 3.20 (1H, d, J=17.3 Hz, CH of CC$\underline{H}_2$), 3.67 (1H, d, J=17.3 Hz, CH OF CC$\underline{H}_2$), 6.31 (1H, s, C=C$\underline{H}$), 6.79 (1H, d, J=6.6 Hz, 1×Ar—H), 6.80–7.17 (2H, m, 2×Ar—H), 7.23–7.31 (1H, t, J=7.2 Hz, 1×Ar—H), 7.41–7.49 (2H, m, 2×Ar—H), 7.62–7.70 (1H, t, J=7.3 Hz, 1×Ar—H), 7.87 (1H, d, J=6.5 Hz, 1×Ar—H)

$^{13}$C NMR (CDCl$_3$, 75.47 MHz) $\delta_C$ 23.9, 24.7, 24.8 (3× $\underline{C}$H$_3$), 41.2 (1×$\underline{C}$H$_2$), 47.8, 50.0 (2×q$\underline{C}$), 120.2, 121.4, 124.7, 125.1, 126.1, 126.7, 127.7, 135.1, 142.9 (8×Ar—$\underline{C}$H and 1×C=$\underline{C}$H), 135.7, 141.0, 141.6, 152.2, 154.5 (4×Ar—C & 1×$\underline{C}$=CH), 208.2 ($\underline{C}$=O)

Elemental microanalysis

C$_{21}$H$_{20}$O requires C, 87.5; H, 6.94; found C, 87.21; H, 7.07.

Synthesis of 1C10

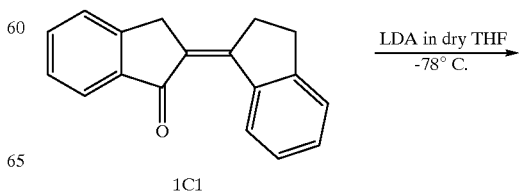

1C1

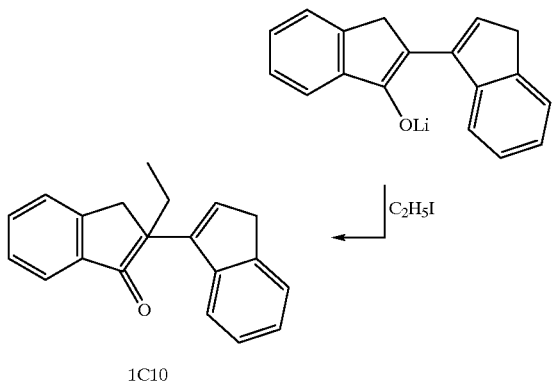

1C10

The reaction yield of 1C10 was 0.87 g, 77.89%.

Low resolution mass spectra: Found M$^+$274, M$^+$−29=245. Required M$^+$274.

$^1$H NMR (CDCl$_3$, 300 MHz) $\delta_H$ 0.83 (3H, t, J 8 Hz, C$\underline{H}_3$), 2.21 (2H, m, J=8 Hz, C$\underline{H}_2$), 3.34 (1H, d, C$\underline{H}$), 3.35 (2H, s, C$\underline{H}_2$), 3.59 (1H, d, J=17 Hz, C$\underline{H}$), 6.49 (1H, t, J=2 Hz, C$\underline{H}$), 7.15–8.0 (8H, m, 8×Ar—$\underline{H}$).

$^{13}$C NMR (CDCl$_3$, 75.47 MHz) $\delta_C$ 8.6 (CH$_2$$\underline{C}$H$_3$), 29.5, 37.4, 38.3 (3×$\underline{C}$H$_2$), 54.4 (q$\underline{C}$), 120.1, 123.9, 123.9, 124.4, 125.7, 126.2, 127.3, 129.7, 134.8, (8×Ar—$\underline{C}$H & C=$\underline{C}$H), 136.9, 143.2, 144.8, 145.1, 152.6 (5×Ar—$\underline{C}$), 207.7 ($\underline{C}$=O).

Synthesis of 1C11

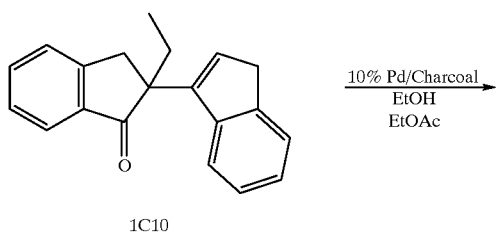

1C10 → 1C11

10% Pd/Charcoal
EtOH
EtOAc

The reaction yield for 1C11 was 163 mg, 73.56%.

$^1$H NMR (CDCl$_3$, 300 MHz) $\delta_H$ 0.75 (3H, m, CH$_3$), 1.25–2.30 (4H, br m, 2×CH$_2$), 2.75 –3.10 (4H, br m, 2×CH$_2$), 3.8 & 3.9 (1H, 2×m, CHCH$_2$CH$_2$), 7.0–7.9 (8H, br m, 8×Ar—H).

$^{13}$C NMR (CDCl$_3$, 75.47 MHz) $\delta_C$ 8.4 & 8.7 (CH$_3$), 28.2, 28.3, 30.7, 31.3, 31.8, 35.0, 35.2 (4×CH$_2$), 50.1, 50.2 (CH), 56.4, 57.0 (qC), 123.6, 124.8, 125.5, 126.2, 126.9, 134.6, 134.7, 137.9, 143.2, 144.2, 144.4, 145.2, 154.2, (Ar—CH & Ar—C), 210.9 (C=O).

Synthesis of 1C12

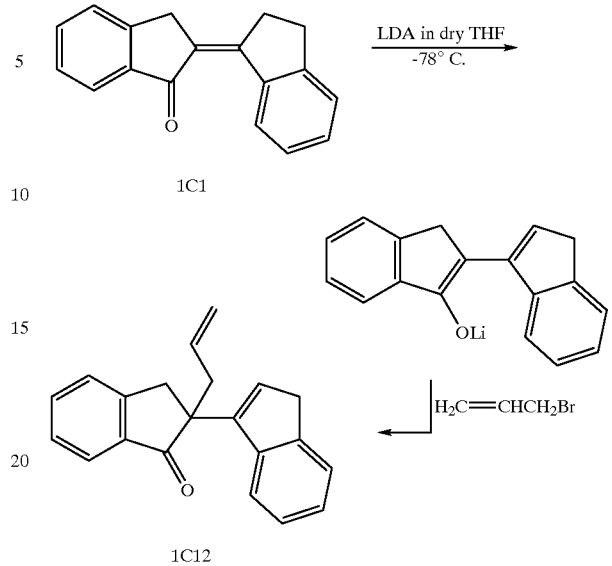

1C1 → 1C12

LDA in dry THF
−78° C.

H$_2$C=CHCH$_2$Br

The reaction yield for 1C12 was 0.78 g, 67.09%.
Low resolution mass spectra: Found: M$^+$286 Required: M$^+$286

$^1$H NMR (CDCl$_3$, 300 MHz) $\delta_H$ 2.94 (2H, d, C$\underline{H}_2$CH=CH$_2$), 3.38 (2H, br s, C=CHC$\underline{H}_2$), 3.53 (2H, ab q, J=17.5 Hz, C$\underline{H}_2$), 4.99 (1H, dd, J=1 Hz, 10 Hz, CH$_2$CH=C$\underline{H}_2$), 5.16 (1H, dd, J=3.3 Hz, 17 Hz, CH$_2$CH=C$\underline{H}$hd 2), 5.62 (1H, m, CH$_2$C$\underline{H}$=CH$_2$), 6.52 (1H, t, J=2 Hz, C=C$\underline{H}$CH$_2$), 7.06 (1H, m, 1×Ar—$\underline{H}$), 7.18 (2H, m, 2×Ar—H), 7.46 (3H, m, 3×Ar—H), 7.65 (1H, dt, J=1.3 Hz & J=7.6 Hz 1×Ar—H), 7.87 (1H, d, J=7.5 Hz, 1×Ar—H).

$^{13}$C NMR (CDCl$_3$, 75.47 MHz) $\delta_C$ 37.6, 37.6, 41.1 (3×$\underline{C}$H$_2$), 53.9 (q$\underline{C}$), 118.7 (CH$_2$C=$\underline{C}$H$_2$), 120.2, 124.0, 124.2, 124.6, 125.8, 126.4, 127.6, 130.3, 132.9, 135.2, (8×Ar—$\underline{C}$H & 2×$\underline{C}$H), 136.2, 143.0, 144.8, 144.9, 152.7 (Ar—$\underline{C}$) 207.4 ($\underline{C}$=O).

Wilkinsons Reduction
Synthesis of 1C13

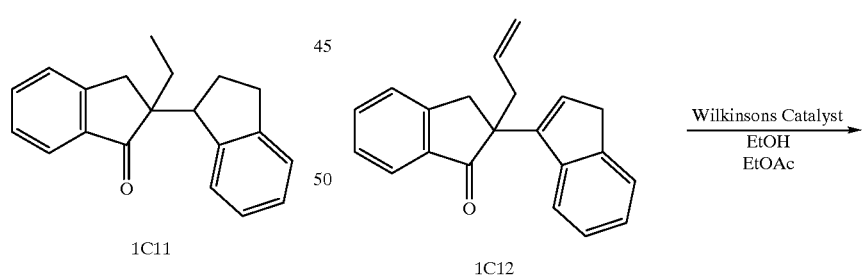

1C12 → 1C13

Wilkinsons Catalyst
EtOH
EtOAc

1C12 (100 mg, 0.349 mmol) was dissolved in ethanol (20 ml) and ethyl acetate (10 ml). To this stirring solution Wilkinsons catalyst (0.1 g) was added. The reaction was then stirred under hydrogen for 20 hours. The product was partitioned between ethyl acetate and water and the organic layer was isolated and dried with $Na_2SO_4$. The crude product was purified by flash column chromatography to yield 1C13 57 mg, 56.60%.

$^1$H NMR ($CDCl_3$, 300 MHz) $\delta_H$ 0.88 (3H, t, J=7 Hz, C$\underline{H}_3$), 1.27 (2H, m, C$\underline{H}_2$), 2.16 (2H, m, C$\underline{H}_2$), 3.36 (2H, br.s, C=CHC$\underline{H}_2$), 3.49 (2H, ab q, J=17.6 Hz, COC$\underline{H}_2$) 6.50 (1H, t, J=2 Hz, C$\underline{H}$), 7.12 (3H, m, 3×Ar—$\underline{H}$), 7.50 (3H, m, 3×Ar—$\underline{H}$), 7.64 (1H, dt, J=1.2 Hz & J=7.6 Hz, 1×Ar—$\underline{H}$), 7.86 (1H, d, J=7.2 Hz, 1×Ar—$\underline{H}$).

$^{13}$C NMR ($CDCl_3$, 75.47 MHz) $\delta_C$ 14.5 ($\underline{C}H_3$), 17.6, 37.6, 38.9, 39.2 (4×$\underline{C}H_2$), 54.3 (q$\underline{C}$), 120.3 ($\underline{C}H$), 124.1, 124.2, 124.6, 125.8, 126.3, 127.6, 129.8, 135.0 (8×Ar—$\underline{C}H$), 136.9, 143.3, 144.9, 145.3, 152.8 (4×Ar—$\underline{C}$ & 1×$\underline{C}$=C), 208.2 ($\underline{C}$=O)

10% Palladium on Carbon Reduction

Synthesis of 1C14

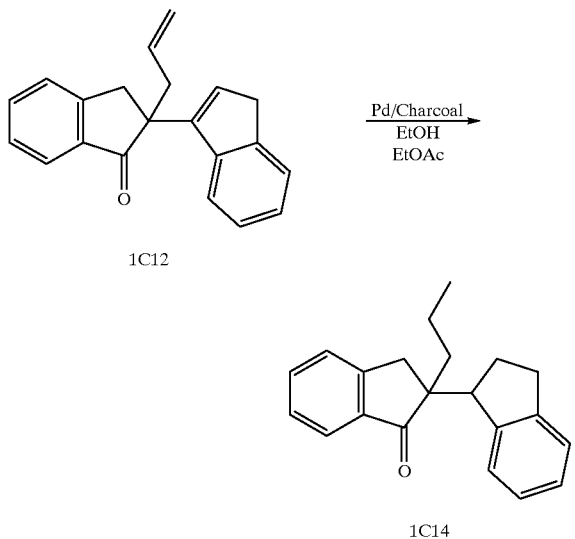

1C12

1C14

The reaction yield for 1C14 was 76 mg, 75.4%.

Where distinguishable values for minor diastereomers are italized $^1$H NMR ($CDCl_3$, 300 MHz) $\delta_H$ 0.92 (3H, t, $CH_3$), 1.10–4.00 (14H, br m, CH & C$\underline{H}_2$'s), 3.74 (1H, m, C$\underline{H}CH_2CH_2$), 6.90–7.90 (8H, m, 8×Ar—$\underline{H}$).

$^{13}$C NMR ($CDCl_3$, 75.47 MHz) $\delta_C$ 14.6 ($\underline{C}H_3$), 17.1, 17.5 ($\underline{C}H_2$), 28.2 ($\underline{C}H_2$), 31.2, 31.8 ($\underline{C}H_2$), 35.3, 35.6 ($\underline{C}H_2$), 40.5, 41.0 ($\underline{C}H_2$), 50.4, 50.6 ($\underline{C}H$), 56.2, 56.7 (q$\underline{C}$), 123.4, 123.6, 123.9, 124.4, 124.8, 125.5, 125.9, 126.1, 126.2, 126.5, 126.8, 127.3, 134.6, 134.7, 137.7, 143.4, 144.2, 144.4, 145.2, 153.7, 154.1 (Ar—$\underline{C}H$ & Ar—$\underline{C}$), 211.0 ($\underline{C}$=O).

Synthesis of 1C15

Sodium Borohydride Reduction

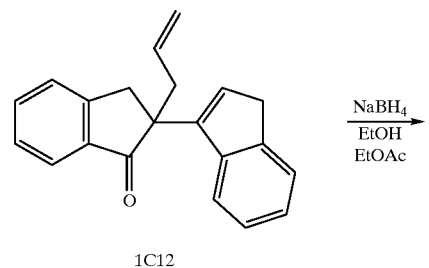

1C12

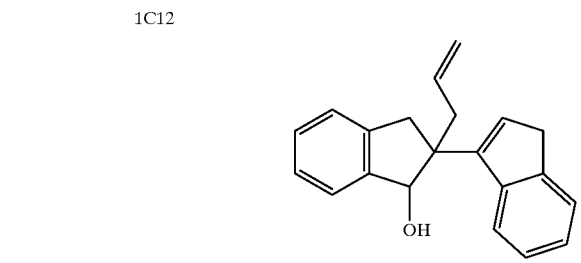

1C15

The method is the same as that described for 1C5.

The reaction yield for 1C15 (73 mg, 72.42%) from which two diastereoisomers were separated by flash column chromatography.

Diastereomeric Mixture 1

$^1$H NMR ($CDCl_3$, 300 MHz) $\delta_H$ 2.55 & 2.61 (1H, 2×d, CC$\underline{H}_2$CH=CH$_2$), 2.89 & 2.94 (1H, 2×d J=6.15 Hz CC$\underline{H}_2$CH=CH$_2$), 3.33 (2H, q, J=16 Hz, C$\underline{H}_2$), 3.35 (2H, d, J=2 Hz, C=CHC$\underline{H}_2$), 4.90 (1H, dd, J=1 Hz, 10 Hz, CH$_2$CH=C$\underline{H}_2$), 4.98 (1H, dd, J=3.3 Hz, 17 Hz, CH$_2$CH=C$\underline{H}_2$), 5.51 (1H, d, J=7.9 Hz, C$\underline{H}$OH), 5.64 (1H, m, C=C$\underline{H}$CH$_2$), 6.40 (1H, s, C=C$\underline{H}$) 7.19 (5H, m, 5×Ar—$\underline{H}$), 7.35 (1H, m, 1×Ar—H), 7.50 (1H, d, J=5 Hz, 1×Ar—H), 7.72 (1H, d, J=5 Hz, 1×Ar—H).

$^{13}$C NMR ($CDCl_3$, 75.47 MHz) $\delta_C$ 37.4, 37.6, 40.4 (3× $\underline{C}H_2$), 53.0 (Q$\underline{C}$), 81.8 ($\underline{C}HOH$), 116.9 (CH=$\underline{C}H_2$), 121.7, 124.1, 124.1, 124.4, 124.7, 125.8, 126.9, 128.4, 129.9, 136.1 (8×Ar—$\underline{C}H$ & 1×C=$\underline{C}H$ & 1×$\underline{C}H$=CH$_2$), 140.7, 143.9, 144.1, 145.3, 148.2 (4×Ar—$\underline{C}$ & 1×$\underline{C}$=CH).

Diastereomeric Mixture 2

$^1$H NMR ($CDCl_3$, 300 MHz) $\delta_H$ 2.24 (1H, d, J=5.39 Hz, CHO$\underline{H}$), 2.87–3.41 (6H, m, 3×C$\underline{H}_2$), 4.91 (2H, m, CH=C$\underline{H}_2$), 5.49 (H, d, J=5.37 Hz, C$\underline{H}$OH), 5.62 (1H, m, C$\underline{H}$=CH$_2$), 6.37 (1H, s, C=C$\underline{H}$CH$_2$), 7.23–7.72 (8H, m, 8×Ar—C$\underline{H}$).

$^{13}$C NMR ($CDCl_3$, 75.47 MHz) $\delta_C$ 29.7, 37.4, 37.6 (3× $\underline{C}H_2$), 81.7 ($\underline{C}$OH), 116.9 (CH=$\underline{C}H_2$), 121.7, 124.0, 124.1, 124.4, 124.7, 125.8, 126.9, 128.3, 129.9, 136.1, (8×Ar$\underline{C}$H & 2×$\underline{C}$=$\underline{C}$H), 140.7, 143.8, 144.0, 145.3, 148.2 (5×Ar—$\underline{C}$).

Synthesis of Acetates

Synthesis of 1C16

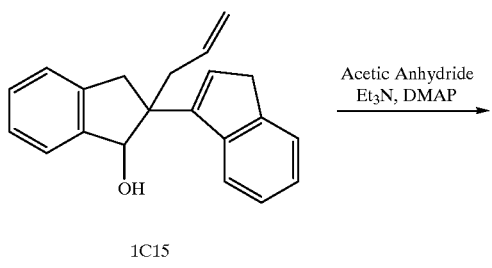

1C15

1C15 (140 mg, 0.5 mmol) was dissolved in clean, dry DCM (10 ml). To this solution was added triethylarmine (0.15 g, 0.20 ml), DMAP (0.1 g) and acetic anhydride (0.45 ml, 10 equivalents). The reaction mixture was stirred at room temperature for 15 minutes and passed through a plug of silica eluting with petroleum spirit (b.p. 40–60° C.):ethyl acetate (8:2) to afford 1C16 (149 mg, 92.9%).

$^1$H NMR (CDCl$_3$, 300 MHz) δH 1.53 (3H, S, OCOC$\underline{H}_3$), 2.23 (1H, dd, J=5.5 and 13.8 Hz, CH of CH$_2$), 2.80 (1H, dd, J=5.5 and 13.8 Hz, CH of C$\underline{H}_2$), 3.22 (1H, d, J=15.8 Hz, CH of C$\underline{H}_2$), 3.44 (2H, s, C$\underline{H}_2$), 3.63 (1H, d, J=15.8 Hz, CH of C$\underline{H}_2$), 4.87 (1H, d, J=17 Hz, CH of C$\underline{H}_2$), 4.95 (1H, d, J=10 Hz, CH of C$\underline{H}_2$), 5.61–5.49 (1H, m C$\underline{H}$), 6.36 (1H, t, J=2.0 Hz, C=C$\underline{H}$), 6.54 (1H, s, C$\underline{H}$OCOCH$_3$), 7.21–7.37 (5H, m, 5×Ar—H), 7.51 (2H, t, J=6.6 Hz, 2×Ar—H), 7.63 (1H, d, J=7.2 Hz, 1×Ar—H)

$^{13}$C NMR (CDCl$_3$, 75.47 MHz) δ$_C$ 20.6 (OCO$\underline{C}$H$_3$), 37.6, 40.0, 40.3 (3×$\underline{C}$H$_2$), 51.6 (qC), 81.7 ($\underline{C}$HOCOCH$_3$), 117.8 (CH=$\underline{C}$H$_2$), 120.8, 123.8, 124.2, 124.9, 125.9, 126.8, 127.1, 129.3, 130.9, 134.1, 140.7, 143.1, 143.6, 144.7, 145.9, (8×Ar—CH, 4×Ar—C, 1 each $\underline{C}$=CH and 1×$\underline{C}$H=CH$_2$), 170.6 (O$\underline{C}$OCH$_3$)

Synthesis of 1C17 & 1C18

Sodium Borohydride Reduction of 1C13

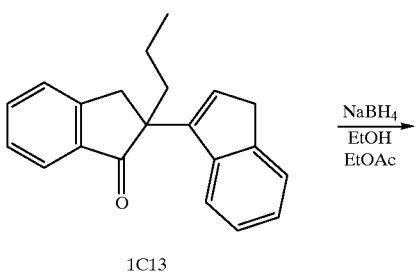

1C13

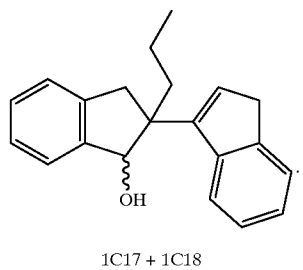

1C17 + 1C18

Yield (90 mg, 90%)

1C17

1H NMR (CDCl$_3$, 300 MHz) δ$^H$ 0.84–2.20 (8H, br m, C$\underline{H}_3$, CH$_2$'s), 3.29 (2H, s, C=CHC$\underline{H}_2$), 3.33 (2H, abq, J=16 Hz, COHCC$\underline{H}_2$), 5.42 (1H, br s, C$\underline{H}$OH), 6.28 (1H, t, J=2.1 Hz, C=C$\underline{H}$), 7.18–7.81 (8H, m, 8×Ar—$\underline{H}$).

$^{13}$C NMR (CDCl$_3$, 75.47 MHz) δ$_C$ 14.8 ($\underline{C}$H$_3$), 18.7, 34.7, 37.5, 40.8 (4×$\underline{C}$H$_2$), 53.6 (q$\underline{C}$), 81.2 ($\underline{C}$HOH), 121.7, 124.0, 124.3, 124.4, 124.7, 125.8, 126.7, 128.3, 129.7, 141.7, 144.1, 144.2, 145.3, 148.2 (8×Ar—$\underline{C}$H & 4×Ar—$\underline{C}$ & 1× $\underline{C}$=CH & 1×C=$\underline{C}$H).

1C18

$^1$H NMR (CDCl$_3$, 300 MHz) δ$_H$ 0.74 (3H, t, J=7.4 Hz, CH$_2$CH$_2$C$\underline{H}_3$), 0.92 (2H, m, CCH$_2$C$\underline{H}_2$CH$_3$), 1.75 (2H, m, CC$\underline{H}_2$CH$_2$CH$_3$), 3.45 (2H, s, CC$\underline{H}_2$), 3.12 & 3.59 (1H each, d. J=15.6 Hz, CHC$\underline{H}_2$), 5.37 (1H, s, C$\underline{H}$OH), 6.45 (1H, s, C=C$\underline{H}$), 7.27–7.79 (8H, m, 8×Ar—$\underline{H}$).

$^{13}$C NMR (CDCl$_3$, 75.47 MHz) δ$_C$ 14.4 ($\underline{C}$H$_3$), 18.5, 29.7, 37.8, 39.4 (4×$\underline{C}$H$_2$), 54.8 (q$\underline{C}$), 81.8 ($\underline{C}$HOH), 120.9, 124.2, 124.7, 125.1, 125.7, 126.3, 126.7, 128.7, 130.9, 142.6, 143.4, 143.7, 145.2, 146.1, (8×Ar—$\underline{C}$H & 4×Ar—$\underline{C}$ & 1× $\underline{C}$=CH & 1×C=$\underline{C}$H).

Synthesis of 1C19

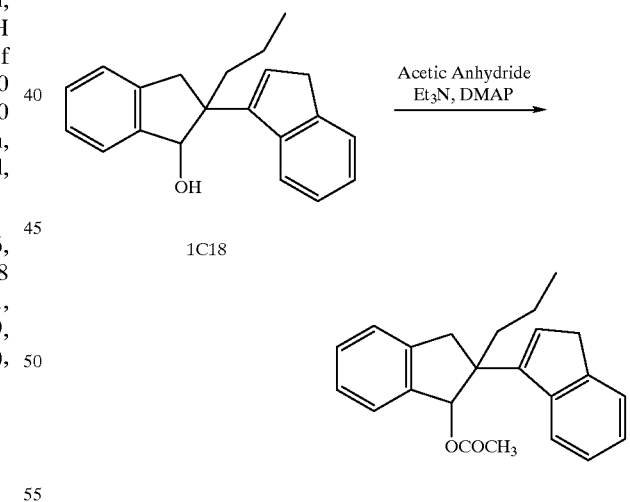

1C18 (70 mg, 0.25 mmol) was dissolved in clean, dry DCM (5 ml). To this solution was added triethylamine (0.15 ml) DMAP (0.05 g) and acetic anhydride (0.25 ml, 10 equivalents). The reaction mixture was stirred at room temperature for 15 minutes and passed through a plug of silica eluting with petroleum spirit (b.p. 40–60° C.):ethyl acetate (8:2) to afford 1C19 (65 mg, 81.1%).

$^1$H NMR (CDCl$_3$, 300 MHz) δH 0.71 (3H, t, J=7.1 Hz, CH$_2$C$\underline{H}_3$), 0.89–1.97 (4H. br. m, C$\underline{H}_2$'s), 1.51 (3H, s, C$\underline{H}_3$), 3.17 (1H, d, J=15.5 Hz, CH of CHC$\underline{H}_2$), 3.40 (2H, s, C$\underline{H}_2$), 3.62 (1H, d, J=15.6 Hz, CH of CHC$\underline{H}_2$), 6.34 (1H, t, J=2.2 Hz, C=C$\underline{H}$), 6.49 (1H, s, C$\underline{H}$OCOCH$_3$), 7.18–7.59 (8H, m, Ar—H)

$^{13}$C NMR (CDCl$_3$, 75.47 MHz) $\delta_C$ 14.3 (CH$_2$$\underline{C}$H$_3$), 18.3 ($\underline{C}$H$_2$), 20.7 (OCO$\underline{C}$H$_3$), 37.6, 38.6, 40.4 (3×$\underline{C}$H$_2$), 52.4 (q $\underline{C}$), 82.4 ($\underline{C}$HOCOCH$_3$), 120.8, 123.8, 124.2, 124.98, 125.9, 126.8, 127.0, 129.3, 130.4 (8×Ar—$\underline{C}$H, vinylic $\underline{C}$H), 141.0, 143.4, 143.9, 144.6, 146.6 (4×Ar—$\underline{C}$ and 1×$\underline{C}$=CHCH$_2$), 170.7 (O$\underline{C}$OCH$_3$)

Synthesis of 1C20

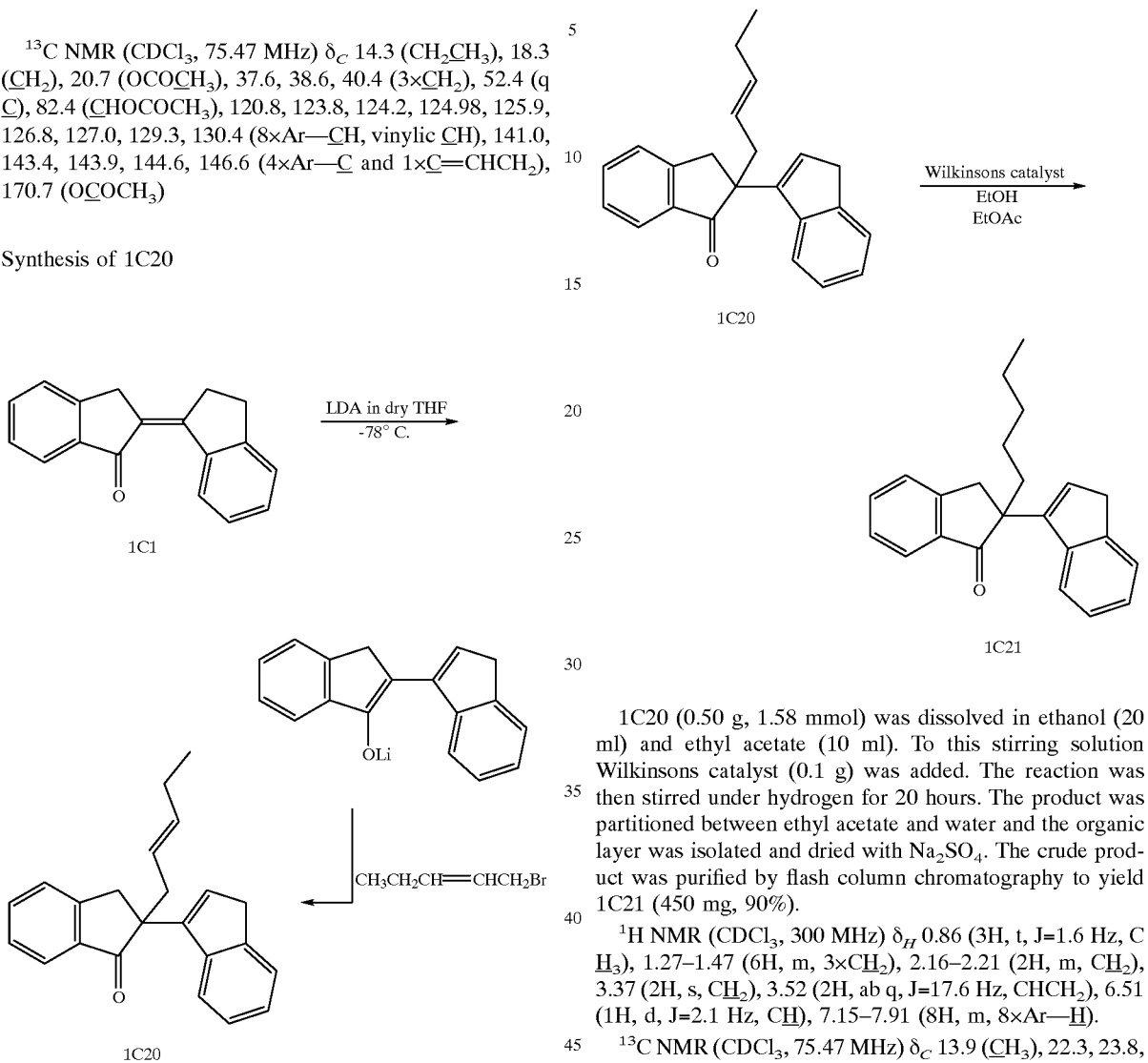

The reaction for 1C20 was 40%.

$^1$H NMR (CDCl$_3$, 300 MHz) $\delta_H$ 0.73 (3H, t, CH$_2$C$\underline{H}_3$), 1.83 (2H, m, C$\underline{H}_2$CH$_3$), 2.85 (2H, d, C$\underline{H}_2$CH=CH), 3.38 (2H, br s, C=CHC$\underline{H}_2$), 3.50 (2H, ab q, J=13.0 Hz, COCC$\underline{H}_2$), 5.18 & 5.58 (2H, 2×m, CH$_2$C$\underline{H}$=C$\underline{H}$CH$_2$), 6.52 (1H, t, J=2 Hz, 1×C=C$\underline{H}$CH$_2$), 7.01 (1H, m, 1×Ar—$\underline{H}$), 7.15 (2H, m, 2×Ar—$\underline{H}$), 7.40 (3H, m, 3×Ar—$\underline{H}$), 7.65 (1H, t, 1×Ar—$\underline{H}$), 7.85 (1H, d, 1×Ar—$\underline{H}$).

$^{13}$C NMR (CDCl$_3$, 300 MHz) $\delta_H$ 13.4 (CH$_3$), 25.4, 37.6, 37.6, 39.9 (4×$\underline{C}$H$_2$), 54.3 (q$\underline{C}$), 120.1, 123.1, 124.0, 124.0, 124.6, 125.8, 126.3, 127.4, 130.2, 135.0, 136.6, 136.9, 143.2, 144.9, 145.1, 152.9 (8×Ar—$\underline{C}$H & 4×Ar—$\underline{C}$ & 1×$\underline{C}$=CH & 1×$\underline{C}$H=$\underline{C}$H), 207.9 (C=O).

Synthesis of 1C21
Wilkinsons Reduction of 1C20

1C20 (0.50 g, 1.58 mmol) was dissolved in ethanol (20 ml) and ethyl acetate (10 ml). To this stirring solution Wilkinsons catalyst (0.1 g) was added. The reaction was then stirred under hydrogen for 20 hours. The product was partitioned between ethyl acetate and water and the organic layer was isolated and dried with Na$_2$SO$_4$. The crude product was purified by flash column chromatography to yield 1C21 (450 mg, 90%).

$^1$H NMR (CDCl$_3$, 300 MHz) $\delta_H$ 0.86 (3H, t, J=1.6 Hz, C$\underline{H}_3$), 1.27–1.47 (6H, m, 3×C$\underline{H}_2$), 2.16–2.21 (2H, m, C$\underline{H}_2$), 3.37 (2H, s, C$\underline{H}_2$), 3.52 (2H, ab q, J=17.6 Hz, CHC$\underline{H}_2$), 6.51 (1H, d, J=2.1 Hz, C$\underline{H}$), 7.15–7.91 (8H, m, 8×Ar—$\underline{H}$).

$^{13}$C NMR (CDCl$_3$, 75.47 MHz) $\delta_C$ 13.9 ($\underline{C}$H$_3$), 22.3, 23.8, 32.2, 36.8, 37.6, 38.8 (6×$\underline{C}$H$_2$), 54.3 (q$\underline{C}$), 120.3, 124.0, 124.1, 124.5, 125.8, 126.3, 127.5, 129.8, 134.9 (8×Ar—$\underline{C}$H & 1×C=$\underline{C}$H), 136.8, 143.3, 144.9, 145.3, 152.7 (4×Ar—$\underline{C}$ & 1×$\underline{C}$=CH), 208.1 ($\underline{C}$=O).

Synthesis of 1C22 & 1C23
Sodium Borohydride Reduction of 1C20

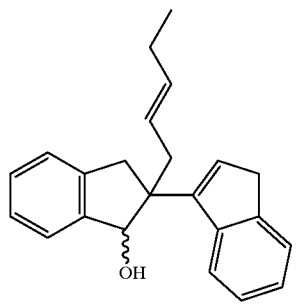

1C22 & 1C23

1C20 (0.50 g, 1.58 mmol) was dissolved in ethanol and ethyl acetate (2:1, 9 ml) and sodium borohydride (0.1 g, 0.263 mmol) was added to the reaction in small portions over 10 minutes. The reaction was stirred at room temperature for 3 hours. The reaction mixture was poured onto water (20 ml) and extracted into diethyl ether (3×20 ml). Flash column chromatography over silica gel eluent: petroleum ether (b.p. 40–60° C.):ethyl acetate, 98:2) afforded 1C22 & 1C23 (470 mg, 95%).

1C22
$^1$H NMR (CDCl$_3$, 300 MHz) $\delta_H$ 0.79 (3H, t, J=7.4Hz, CH$_2$CH$_3$), 1.83–3.36 (8H, br m, CH$_2$'s), 5.21–5.53 (2H, m, CH$_2$CH=CHCH$_2$), 5.54 (1H, br s, CHOH), 6.21, 6.43 (1H, 2×s, CH=C), 7.21–7.71 (8H, m, 8×Ar—H).

1C23
$^1$H NMR (CDCl$_3$, 300 MHz) $\delta_H$ 0.34–3.52 (12H, m, CH$_2$'s), 5.09–5.29 (2H, m, CH=CH), 5.36 (1H, br.m, CHOH), 6.42 (1H, d, J=6.5 Hz, CH=C), 7.23–7.76 (8H, m, 8×Ar—H).

Synthesis of 1C24

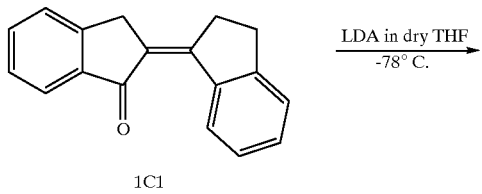

1C1

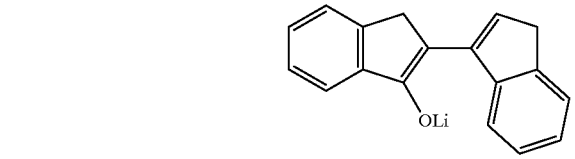

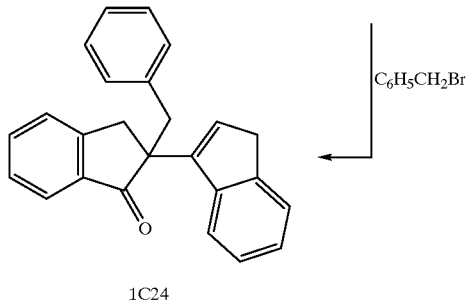

1C24

The reaction yield for 1C24 was 230 mg, 33.67%.
Low resolution mass spectra: Found M$^+$336 M$^+$-91=245 Required M$^+$336.

$^1$H NMR (CDCl$_3$, 300 MHz) $\delta_H$ 3.37 (2H, dd, C=CHCH$_2$), 3.55 (2H, ab q, J=13 Hz, CCH$_2$), 3.54 (2H, d, J=14 Hz, PhCH$_2$), 6.53 (1H, t, J=2 Hz, C=CH), 7.12 (5H, m, 5×Ar—H), 7.25 (5H, br m, 5×Ar—H), 7.47 (2H, m, 2×Ar—H), 7.78 (1H, d, J=7 Hz, 1×Ar—H).

$^{13}$C NMR (CDCl$_3$, 75.47 MHz) $\delta_C$ 36.8, 37.6, 41.7 (3× CH$_2$), 55.5 (qC), 120.5, 123.9, 124.2, 124.7, 125.9, 126.1, 126.4, 127.7, 127.2, 130.2, 130.2, 130.4, 134.8 (13×Ar—CH & 1×C=CH), 136.6, 136.7, 143.1, 145.1, 145.1, 152.6 (5×Ar—C & C=CH).

Sodium Borohydride Reduction
Synthesis of 1C25 & 1C26

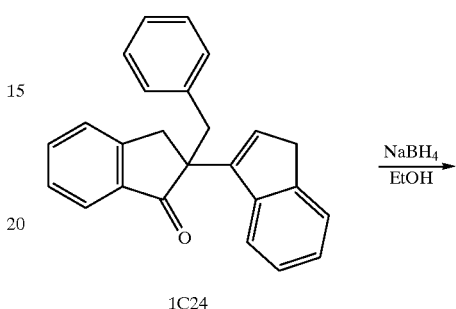

1C24

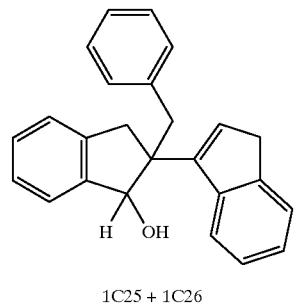

1C25 + 1C26

1C25 and 1C26 was isolated, yield 90 mg, 89.45% as a mixture of diastereomers.

$^1$H NMR (CDCl$_3$, 300 MHz) $\delta_H$ 2.58–3.62 (6H, br m, 3×CH$_2$), 5.45 & 5.56 (1H, 2×br s, CHOH), 6.04 & 6.09 (1H, 2×s, C=CHCH$_2$), 6.64 (1H, d, J=2 Hz, Ar—CH), 7.15 (9H, m, 9×Ar—CH), 7.67 (1H, d, Ar—CH), 7.98 (1H, dd, Ar—CH), 7.90 & 8.10 (1H, 2×d, J=Hz, 1×Ar—CH).

$^{13}$C NMR (CDCl$_3$, 75.47 MHz) $\delta_C$ 37.1, 37.4, 37.8, 38.4, 39.6, 40.9 (5×CH$_2$), 55.2, 55.8 (qC), 81.2, 81.3 (CHOH), 120.9, 122.3, 123.9, 124.3, 124.4, 124.5, 124.7, 124.7, 124.9, 125.1, 125.8, 125.9, 126.1, 126.1, 126.5, 126.5, 126.7, 126.9, 127.3, 127.4, 127.4, 128.4, 129.0, 130.2, 130.2, 130.2, 131.2, 134.2 (Ar—CH and C=CH), 137.8, 138.7, 141.2, 142.4, 143.2, 143.6, 144.2, 145.2, 145.2, 147.4 (Ar—C).

Synthesis of 1C27

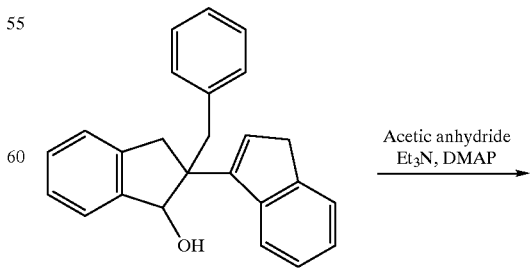

1C25 & 1C26

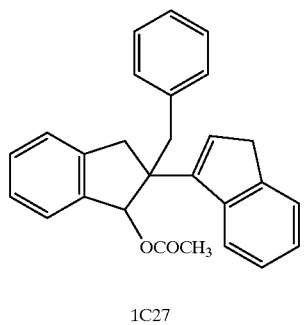

1C27

1C25/1C26 (50 mg, 1.5 mmol) was dissolved in clean, dry DCM (5 ml). To this solution was added triethylarmine (0.1 ml), DMAP (0.05 g) and acetic anhydride (0.25 ml, 10 equivalents). The reaction mixture was stirred at room temperature for 15 minutes and passed through a plug of silica eluting with petroleum spirit (b.p. 40–60° C.):ethyl acetate (8:2) to afford 1C27 (48 mg, 85.4%) as a mixture of diastereomers.

$^1$H NMR (CDCl$_3$, 300 MHz) δH 1.56 and 2.23 (6H, 2×s, 2×OCOC$\underline{H}_3$), 2.57–3.73 (12H, m, 6×C$\underline{H}_2$), 5.59 and 6.6 (4H, 2×m, 2×C$\underline{H}$, 2×C$\underline{H}$COCH$_3$), 6.90–7.73 (25H, m, 25×Ar—H), 8.1 (1H, d, J=6 Hz, 1×Ar—$\underline{H}$)

$^{13}$C NMR (CDCl$_3$, 75.47 MHz) δ$_C$ 20.8, 21.4 (OCO$\underline{C}$H$_3$), 37.4, 37.5, 38.1, 39.2, 40.6, 41.0 (3×$\underline{C}$H$_2$), 53.4, 54.1 (q$\underline{C}$), 81.2, 81.7 ($\underline{C}$HOCOCH$_3$), 120.6, 121.9, 124.0, 124.1, 124.3, 124.4, 124.9, 126.0, 126.1, 126.2, 126.6, 126.9, 127.3, 127.5, 129.0, 129.5, 129.9, 130.5, 132.2, 132.24, 137.2, 138.3, 140.8, 143.2, 143.4, 143.5, 143.8, 144.6, 144.9, 145.2 (Ar—$\underline{C}$H, vinylic $\underline{C}$ and Ar—$\underline{C}$), 170.5 (O$\underline{C}$OCH$_3$)

10% of Palladium on Carbon Reduction

Synthesis of 1C28

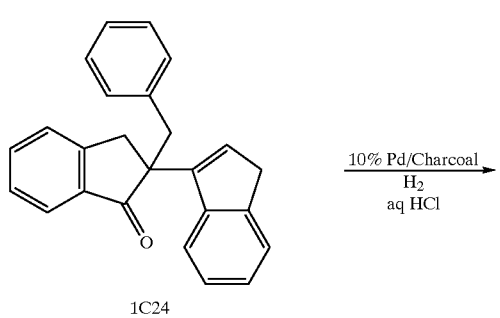

1C28

1C24 (106 mg, 0.315 mmol) was dissolved in distilled ethanol (5 ml) and ethyl acetate (1 ml). To this solution was added concentrated HCl 37% solution (0.2 ml) was added together with water (0.4 ml), and Pd/Charcoal (catalytic quantities) and the mixture was stirred under hydrogen for 24 hours.

The catalyst was removed by filtration and the product was extracted into ethyl acetate (3×20 ml). The crude product was purified by flash column chromatography (eluent: petroleum ether:ethyl acetate, 99:1) to yield 1C28 83 mg, 81.7%.

$^1$H NMR (CDCl$_3$, 300 MHz) δ$_H$ 2.04–2.33 (2H, each m, C$\underline{H}_2$), 2.76–3.05 (8H, m, 4×C$\underline{H}_2$), 3.52 (1H, m, C $\underline{H}$CH$_2$CH$_2$), 7.05–7.40 (13H, br.m, 13×Ar—$\underline{H}$).

$^{13}$C NMR (CDCl$_3$, 75.47 MHz) δ$_C$ 28.9, 31.7, 41.6, 41.9, 42.5, (5×$\underline{C}$H$_2$), 51.4 (q$\underline{C}$), 52.2 (CH), 124.3, 124.4, 124.7, 125.8, 125.8, 125.9, 126.0, 126.0, 126.5, 127.6, 127.6, 130.6 130.6 (13×Ar—$\underline{C}$H), 138.8, 142.6, 142.9, 144.7, 145.6 (5×Ar—$\underline{C}$).

Synthesis of 1C29

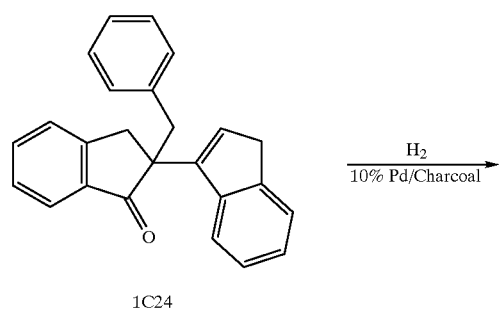

1C24

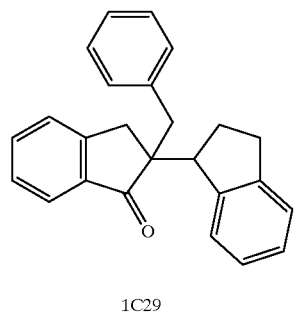

1C29

1C29 was isolated as a mixture of diastereomers (170 mg, 50.45%).

Where distinguishable the minor diastereomers values are italized.

$^1$H NMR (CDCl$_3$, 300 MHz) δ$_H$ 2.10–4.10 (8H, br m, CH & C$\underline{H}_2$'s), 6.77–7.80 (13H, br m, 13×Ar—H).

$^{13}$C NMR (CDCl$_3$, 75.47 MHz) δ$_C$ 28.5, 28.8, 31.3, 31.6, 33.5, 33.8, 43.1, 43.7 (4×C$\underline{H}_2$), 51.1 ($\underline{C}$H), 57.6, 57.8 (q$\underline{C}$), 123.0, 123.3, 124.2, 124.4, 124.9, 125.4, 125.7, 125.8, 125.9, 126.2, 126.6, 126.8, 126.9, 126.9, 127.5, 127.7, 129.8, 130.0, 134.2, 134.4, 136.2, 136.6, 137.6, 138.2, 142;7, 144.0, 144.4, 145.3, 153.4, 153.8, (Ar—$\underline{C}$H's & Ar—$\underline{C}$'s), 210.3, 210.6 ($\underline{C}$=O).

Sodium Borohydride Reduction

Synthesis of 1C30

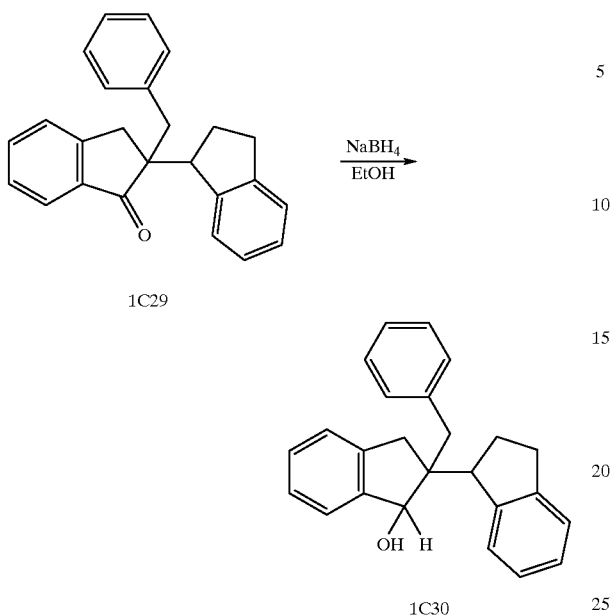

The reaction yield for 1C30 was 63 mg, 62.81%.
$^1$H NMR (CDCl$_3$, 300 MHz) $\delta_H$ 1.83–3.50 (9H, br m, CH, CH$_2$'s), 4.94–5.32 (1H, m, CHOH), 6.98–7.29 (13H, m, Ar—H).

Synthesis of 1C31

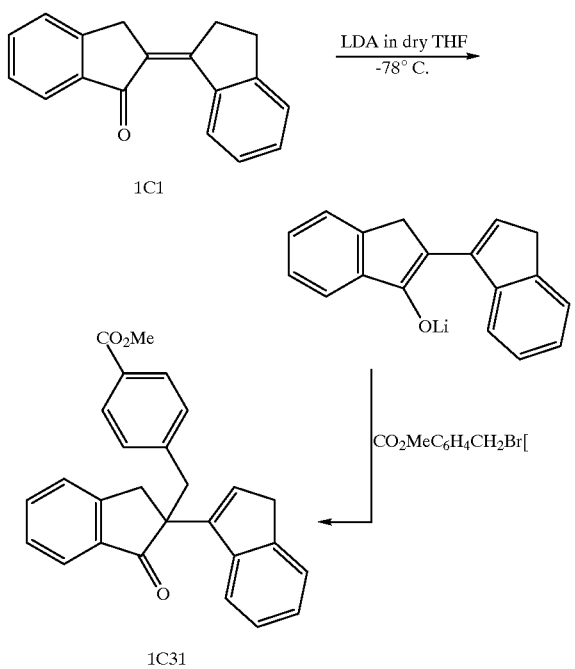

The reaction yield for 1C31 was 60%.
$^1$H NMR (CDCl$_3$, 300 MHz) $\delta_H$ 3.37 (2H, dd, J=1.8 Hz, C=CHCH$_2$), 3.45, 3.56 (2H, d, PhCH$_2$), 3.57 (2H, q, J=13.0 Hz, C—CH$_2$), 3.84 (3H, s, CH$_3$), 6.48 (1H, t, J=1.8 Hz, C H), 7.25 (7H, m, 7×Ar—H), 7.46 (2H, dt, 2×Ar—H), 7.77 (3H, m, 3×Ar—H).
$^{13}$C NMR (CDCl$_3$ 75.47 MHz) $\delta_C$ 36.9, 37.6, 41.6 (3× CH$_2$), 51.9 (CH$_3$), 55.4 (qC), 128.4 (Ar—C), 120.5, 124.0, 124.3, 124.8, 125.9, 126.1, 127.5, 129.2, 129.2, 130.2, 130.2, 130.6, 135.1, (12×Ar—CH & 1×CH=C), 136.5, 142.1, 142.9, 144.6, 145.1, 152.3 (5×Ar—C & 1×C=CH), 166.8 (CO$_2$CH$_3$), 207.2 (C=O).

Hydrolysis of 1C31
Synthesis of 1C32

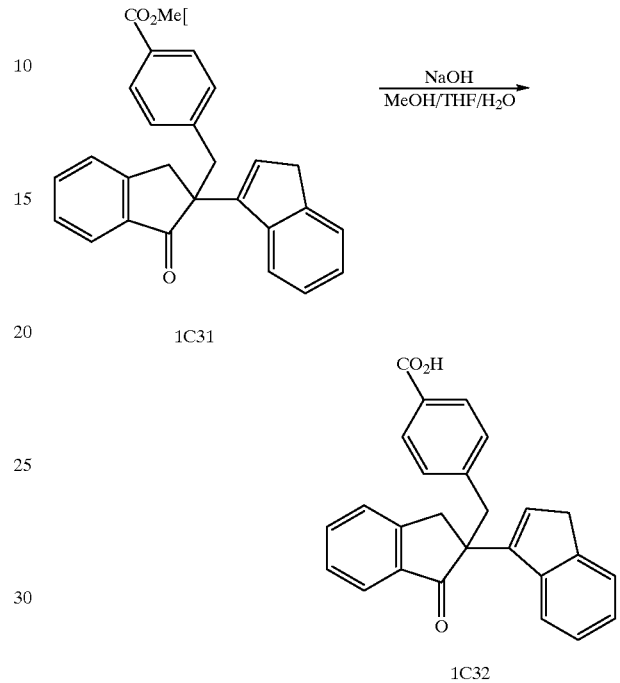

The benzoate ester 1C31 (0.1 g, 0.253 mmol) was dissolved in a solution of 1.45 M NaOH in THF-MeOH—H$_2$O (6:3:2) (4 ml), which was then refluxed. After 20 minutes, TLC showed that the hydrolysis of the benzoate ester 1C31 was complete. After cooling the reaction mixture, a saturated solution of aqueous ammonium chloride (4 ml), aqueous HCl (2 M) (10 ml) and ether (30 ml) was added. The organic layer was isolated and the aqueous layer was extracted with ether (1×10 ml). The combined organic extracts were dried with Na$_2$SO$_4$ and filtered. Evaporation, left the acid 1C32 as a slightly coloured solid.
$^1$H NMR (CDCl$_3$, 300 MHz) $\delta_H$ 3.39 & 3.45 (2H, dd, J=Hz C=CHCH$_2$), 3.49 & 3.57 (2H, d, PhCH$_2$), 3.59 (2H, q, C—CH$_2$), 6.49 (1H, br s, CH), 7.22 (8H, m, 8×Ar—H), 7.47 (2H, t, 2×Ar—H), 7.79 (1H, d, 1×Ar—H), 7.89 (2H, d, 2×Ar—H).
$^{13}$C NMR (CDCl$_3$ 75.47 MHz) $\delta_C$ 36.9, 37.9, 41.7 (3×CH$_2$), 55.4 (qC), 120.5, 124.1, 124.3, 124.8, 126.0, 126.2, 127.4, 129.8, 129.8, 130.3, 130.3, 130.7, 136.4 (12× Ar—CH & 1×C=CH), 135.2, 135.2, 142.9, 143.1, 144.6, 145.1, 152.3 (6×Ar—C & 1×C=CH), 171.6 (CO$_2$H), 207.3 (C=O).

Synthesis of 1C33

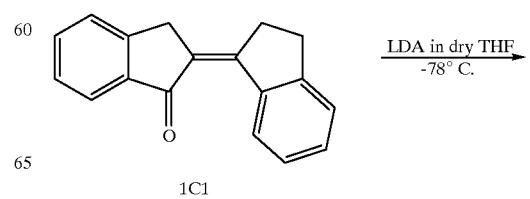

-continued

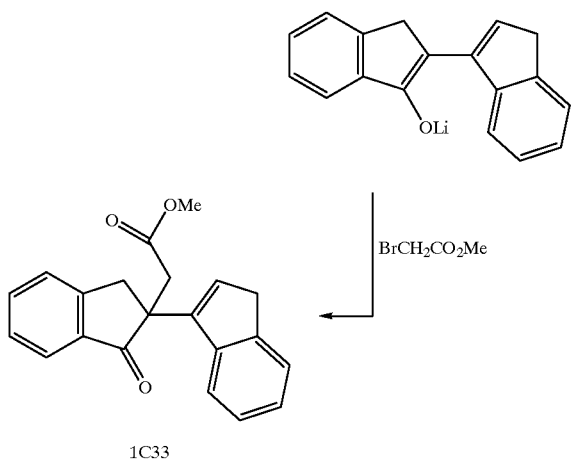

1C33

The reaction yield for 1C33 was 0.53 g, 41.12%.

$^1$H NMR (CDCl$_3$, 300 MHz) $\delta_H$ 3.31 (2H, q, J=16.2 Hz, COCH$_2$), 3.30 (2H, dd, J=2 Hz, C=CHCH$_2$), 3.54 (3H, s, COOCH$_3$), 3.65 (2H, ab q, CH$_2$COOCH$_3$), 6.31 (1H, t, CH), 7.25 (3H, m, 3×Ar—H), 7.42 (3H, m, 3×Ar—H), 7.63 (1H, dt, 1×Ar—H), 7.91 (1H, m, 1×Ar—H).

$^{13}$C NMR (CDCl$_3$ 75.47 MHz) $\delta_C$ 37.6, 38.2, 39.8, (3× CH$_2$), 51.6 (CH$_3$), 52.0 (qC), 120.3, 124.3, 124.3, 124.3, 125.9, 126.3, 127.5, 130.4, (8×Ar—CH), 134.9 (CH), 136.1, 142.5, 143.6, 145.0, 145.0, 152.2 (5×Ar—C & 1×C=CH), 171.4 (CO$_2$CH$_3$), 206.2 (C=O).

Synthesis of 1C34
Hydrolysis of 1C33

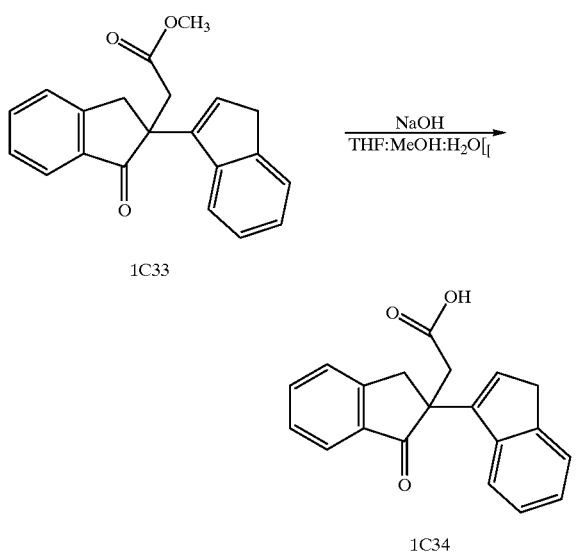

1C33 (0.1 g, 0.316 mmol) was dissolved in a solution of 1.45 M NaOH in THF:MeOH:H$_2$O (6:3:2) (4 ml), which was then refluxed. After 0.5 hr TLC showed that hydrolysis of BRA 64 was complete. This was then partitioned between DCM (50 ml) and dilute HCl (1 M 20 ml). The organic layer was isolated and the aqueous layer extracted with DCM (2×50 ml). The combined organic extracts were washed with water and dried over Na$_2$SO$_4$ and filtered. Evaporation left the acid 1C34 as a gum.

$^1$H NMR (CDCl$_3$, 300 MHz) $\delta_H$ 3.26 (4H, br m, C=CH CH$_2$ & CH$_2$COOH), 3.64 (2H, ab q J=17.0 Hz, COCH$_2$), 6.28 (1H, t, J=2 Hz, C=CHCH$_2$), 7.18 (3H, br m, 3×Ar—H), 7.45 (3H, br m, 3×Ar—H), 7.65 (1H, dt, 1×Ar—H), 7.86 (1H, br d, 1×Ar—H).

Synthesis of 1C35

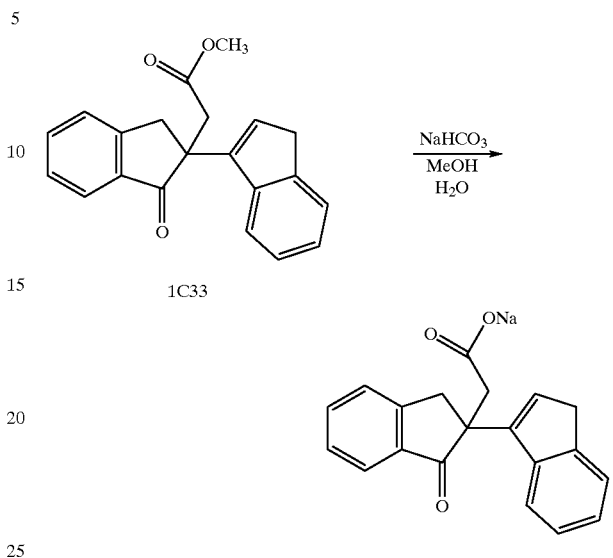

Synthesis of 1C36 and 1C37
5% Palladium on Carbon Method

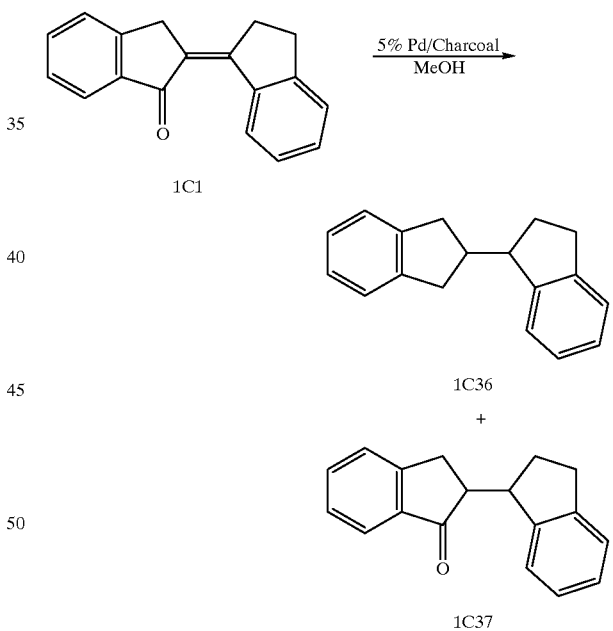

1C1 (200 mg, 0.8 mmol) was dispersed in methanol (20 ml) and to this was added 5% Palladium on carbon (100 mg). The mixture was stirred under hydrogen for 12 hours. The Palladium was removed by filtration and the solvent was removed to afford the crude reaction product. Flash column chromatography (eluent: petroleum spirits b.p. 40–60° C.: ethyl acetate 95:5) afforded 1C37 126 mg, 66.23% and 1C36 37 mg, 18.35%.

NMR data for 1C37: where distinguishable the values for the minor are itallised.

$^1$H NMR (CDCl$_3$, 300 MHz) $\delta_H$ 194–2.17 (1H, m, CO—CH), 2.36–3.49 (6H, m, 3×CH$_2$), 3.98–4.14 (1H, m, CH—CHCH$_2$CH$_2$), 6.73–7.14 (1H, m, 1×Ar—H), 7.15–7.31 (3H, m, 1×Ar—H), 7.33–7.42 (2H, m, 1×Ar—H), 7.49–7.52 (1H, m, 1×Ar—H), 7.77–7.88 (1H, m, Ar—H).

$^{13}$C NMR (CDCl$_3$, 75.47 MHz) δ$_C$ 25.9, 26.2, 29.6, 30.9, 31.5, 31.7 (3×CH$_2$), 45.0, 45.1, 49.6 (2×CH), 123.2, 123.7, 124.5, 126.0, 126.3, 126.5, 126.7, 134.5 (8×Ar—CH), 134.7, 137.3, 137.5, 143.0, 144.2, 144.5, 154.0, 154.4 (4×Ar—C), 207.8, 208.1 (C=O).

NMR Data for IC36

Low resolution mass spectra: Found M$^+$234 Required M$^+$234

$^1$H NMR (CDCl$_3$, 300 MHz) δ$_H$ 1.97 & 2.30 (2H, 2×br m, CHCH$_2$CH$_2$), 3.00 3.22 & 3.45 (8H, 3×br m, 3×CH$_2$ & 2×CHCH), 7.30 (8H, m, 8×Ar—H).

$^{13}$C NMR (CDCl$_3$, 300 MHz) δ$_C$ 29.8, 31.3, 36.9, 38.0 (4×CH$_2$), 43.7, 49.5 (2×CH), 124.2, 124.3, 124.3, 124.5, 124.5, 126.0, 126.1, 126.4 (8×Ar—CH), 143.3, 143.6, 144.4, 146.4 (4×Ar—C).

Synthesis of 1C38

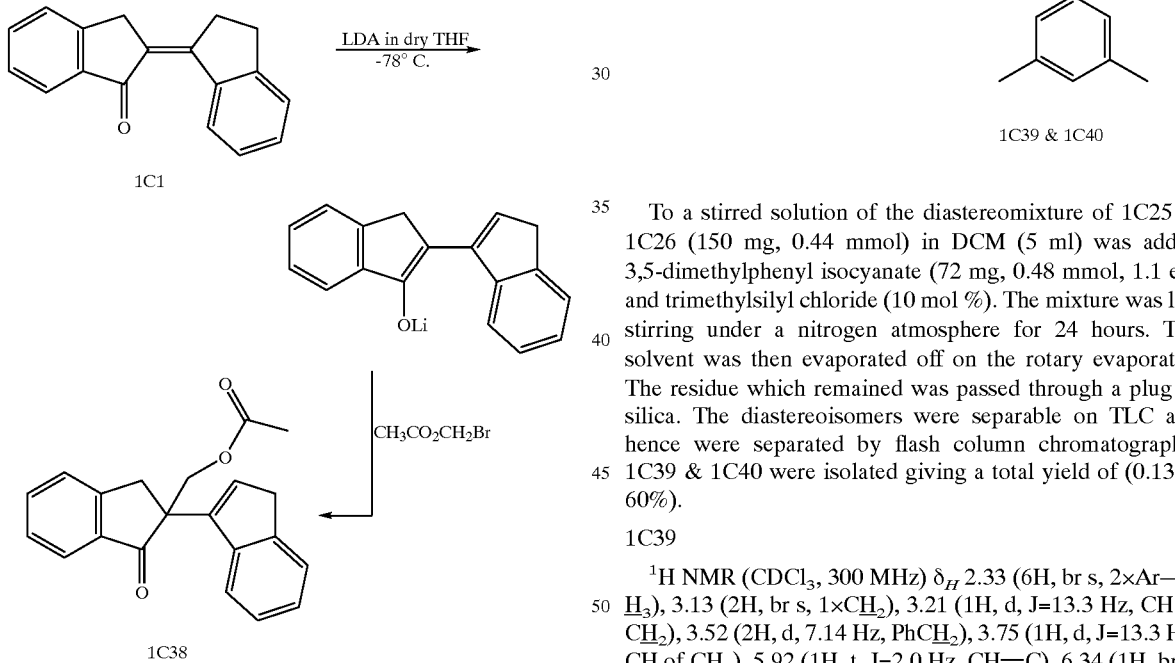

1C1

1C38

$^1$H NMR (CDCl$_3$, 300 MHz) δ$_H$ 1.88 (3H, s, OCOCH$_3$), 3.55 (2H, t, J=2.7 Hz, C=CHCH$_2$), 3.58 (2H, ab q, J=17.0 Hz, CCH$_2$), 4.55, 4.91 (2H, 2×d, J=10.7 Hz, CH$_2$O—COCH$_3$), 7.16 (3H, br m, 3×Ar—H), 7.45 (3H, m, 3×Ar—H), 7.65 (1H, dt, J=6 Hz, 1.32 Hz 1×Ar—H), 7.9 (1H, d, J=6 Hz, 1×Ar—H).

$^{13}$C NMR (CDCl$_3$, 75.47 MHz) δ$_C$ 20.5 (CH$_3$COO), 36.3, 37.8 (2×CH$_2$), 54.2 (CCO), 66.7 (CH$_2$OCOCH$_3$), 120.1, 124.1, 124.4, 124.9, 126.0, 126.4, 127.6, 131.3, 135.3, 136.2, 141.5, 142.6, 144.7, 152.6 (8×Ar—CH & 4×Ar—C & 1×C=CH), 170.6 (CH$_3$COO), 205.1 (C=O).

Synthesis of 1C39 & 1C40

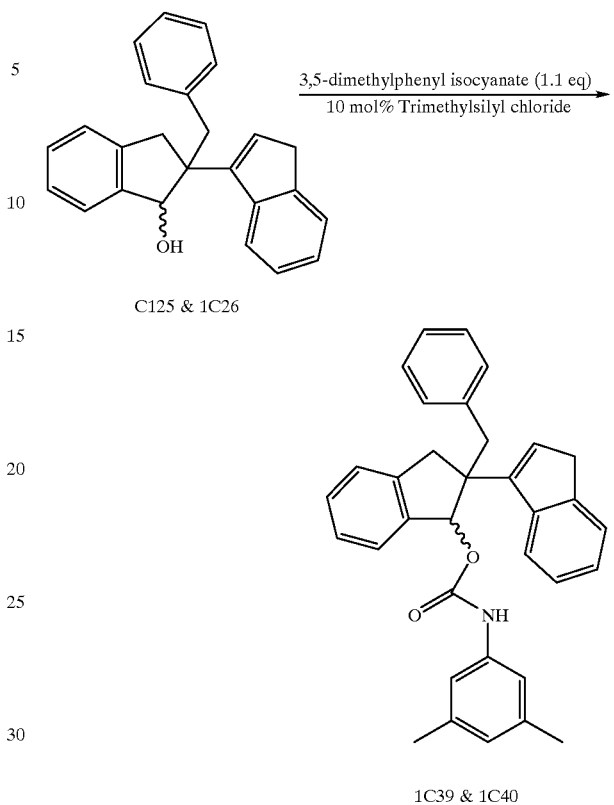

C125 & 1C26

1C39 & 1C40

To a stirred solution of the diastereomixture of 1C25 & 1C26 (150 mg, 0.44 mmol) in DCM (5 ml) was added 3,5-dimethylphenyl isocyanate (72 mg, 0.48 mmol, 1.1 eq) and trimethylsilyl chloride (10 mol %). The mixture was left stirring under a nitrogen atmosphere for 24 hours. The solvent was then evaporated off on the rotary evaporator. The residue which remained was passed through a plug of silica. The diastereoisomers were separable on TLC and hence were separated by flash column chromatography. 1C39 & 1C40 were isolated giving a total yield of (0.13 g, 60%).

1C39

$^1$H NMR (CDCl$_3$, 300 MHz) δ$_H$ 2.33 (6H, br s, 2×Ar—CH$_3$), 3.13 (2H, br s, 1×CH$_2$), 3.21 (1H, d, J=13.3 Hz, CH of CH$_2$), 3.52 (2H, d, 7.14 Hz, PhCH$_2$), 3.75 (1H, d, J=13.3 Hz, CH of CH$_2$), 5.92 (1H, t, J=2.0 Hz, CH=C), 6.34 (1H, br s, ArNHCOO), 6.65 (1H, s, Ar—H), 6.72–7.41 (15H, br m, 15×Ar—H).

1C40

$^1$H NMR (CDCl$_3$, 300 MHz) δ$_H$ 2.20 (6H, br s, 2×Ar—CH$_3$), 2.64 (1H, d, J=13.1 Hz, CH of CH$_2$), 3.07 (1H, d, J=15.8 Hz, CH of CH$_2$), 3.41 (4H, m, 4×CH of CH$_2$'s), 5.91 (1H, br, s, CH=C), 6.03 (1H, s, ArNHCOO), 6.58 (4H, m, 4×Ar—H), 7.10–7.40 (9H, br m, 9×Ar—H), 7.50 (1H, d, J=7.2 Hz, 1×Ar—H), 7.70 (1H, d, J=7.7 Hz, 1×Ar—H), 7.78 (1H, d, J=7.5 Hz, 1×Ar—H).

Synthesis of 3-(3'-Bromo-2',4'-dimethylphenyl)-1-chloro-3-oxopropane (1) and 3-(4'-bromo-3',5'-dimethlyphenyl)-1-chloro-3-oxopropane (2)

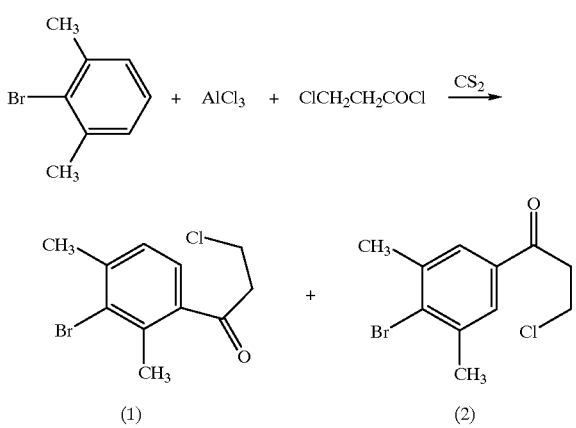

To a mixture of AlCl$_3$ (10.0 g, 75 mmol) in CS$_2$ (50 ml) was added dropwise β-chloropropionylchloride (7.48 g, 59 mmol). To this mixture was added bromo-m-xylene (10 g, 54 mmol) in CS$_2$ (10 ml) dropwise over 30 minutes at 0° C. The reaction mixture was stirred for a further 3 hours at room temperature and then poured onto iced water. To this mixture was added ethyl acetate. The organic layer was isolated and the aqueous layer was extracted with ethyl acetate (2×100 ml). The combined organic layers were washed with water (2×100 ml) and dried with Na$_2$SO$_4$. After evaporation of solvent the crude products (1) and (2) were isolated.

Synthesis of 6-Bromo-5,7-dimethylindan-1-one (3) and 5-Bromo-4,6-dimethylindan-1-one (4)

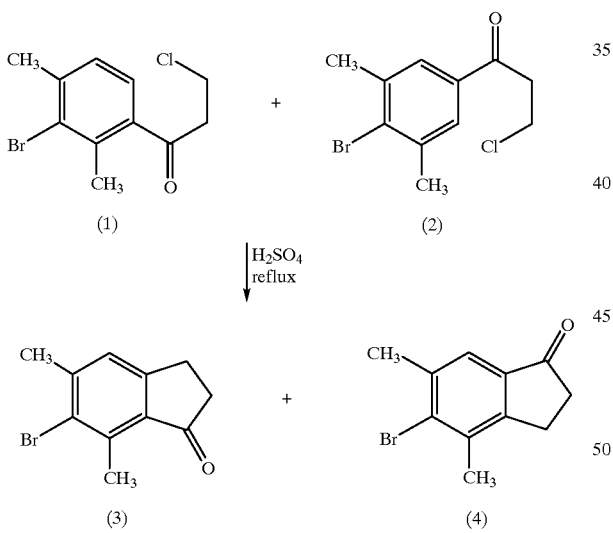

A solution of the crude products (1) and (2) (12.0 g) in concentrated sulphuric acid (75 ml) was heated on an oil bath at 80° C. (optimum temperature). After 3 hours the reaction mixture was poured onto iced water (400 ml) and to this ethyl acetate was added. The organic layer was isolated and the aqueous layer was extracted with ethyl acetate (2×250 ml). All the organic phases were combined and dried with Na$_2$SO$_4$. Flash column chromatography over silica gel (eluent: petroleum spirit (b.p. 40–60° C.): ether, 9:1) afforded compounds (3) (56%) and (4) (42%).

$^1$H NMR (CDCl$_3$, □300 MHz) δ$_H$ (Compound 3) 2.46 (3H, s, C$\underline{H}_3$), 2.71 (3H, s, C$\underline{H}_3$), 2.65 (2H, t, J=6.0 Hz, C$\underline{H}_2$), 2.95 (2H, t, J=6.0 Hz, C$\underline{H}_2$), 7.16 (1H, s, Ar—$\underline{H}$).

$^{13}$C NMR (CDCl$_3$, 75.47 MHz) δ$_c$ (Compound 3) 17.8, 24.4 (2×$\underline{C}$H$_3$), 24.9, 37.3 (2×$\underline{C}$H$_2$), 125.8 (Ar—$\underline{C}$H), 127.9, 133.4, 138.8, 144.6, 154.4 (5×Ar—$\underline{C}$), 206.3 ($\underline{C}$=O).

$^1$H NMR (CDCl$_3$, 300 MHz) δ$_H$ (Compound 4) 2.35 (3H, s, C$\underline{H}_3$), 2.39 (3H, s, C$\underline{H}_3$), 2.61 (2H, t, C$\underline{H}_2$), 2.94 (2H, t, C$\underline{H}_2$), 7.37 (1H, s, Ar—$\underline{H}$).

$^{13}$C NMR (CDCl$_3$, 75.47 MHz) δ$_C$ (Compound 4) 18.8, 24.1 (2×$\underline{C}$H$_3$), 25.2, 36.2 (2×$\underline{C}$H$_2$), 121.9 (Ar—$\underline{C}$H), 134.9, 135.6, 136.0, 137.8, 152.2 (5×Ar—$\underline{C}$), 206.2 ($\underline{C}$=O).

Synthesis of 1C41
Aluminium Tri-tert-butoxide Method.
Synthesis of 1C41

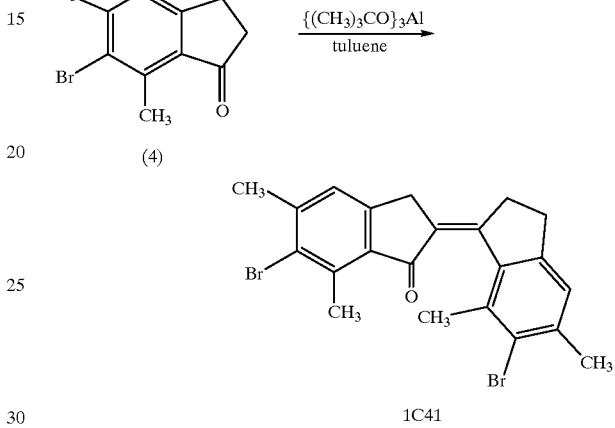

After evaporation of the eluent 1C41 was obtained as an oil 10%.

$^1$H NMR (CDCl$_3$, 300 MHz) δ$_H$ 2.51 (3H, s, C$\underline{H}_3$), 2.48 (3H, s, C$\underline{H}_3$), 2.46 (3H, s, C$\underline{H}_3$), 2.85 (3H, s, C$\underline{H}_3$), 2.82 and 2.88 (2H, m, C=CH$_2$C$\underline{H}_2$), 3.49 (2H, m, C=C$\underline{H}_2$CH$_2$), 3.52 (2H, s, C=C$\underline{H}_2$) , 7.11 and 7.14 (2H, 2×s, 2×Ar—$\underline{H}$).

$^{13}$C NMR (CDCl$_3$ 75.47 MHz) δ$_C$ 17.5, 24.5, 24.6, 25.1 (4×$\underline{C}$H$_3$), 31.3, 33.6, 34.1 (3×$\underline{C}$H$_2$), 124.7, 124.9, (2×Ar—$\underline{C}$H), 127.4, 128.1, 130.5, 134.2, 135.4, 138.8, 140.1, 140.4, 143.9, 147.1, 148.4 and 154.9 (Ar—$\underline{C}$ and q$\underline{C}$), 194.9 ( $\underline{C}$=O).

Formation of Cyclicketal of 1-indanone

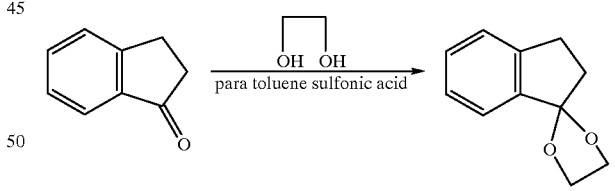

To a solution of toluene/ethylene glycol (2:1, 150 ml) was added indan-1-one (1.0 g, 7.57 mmol) and a catalytic amount of p-toluenesulfonic acid approx 1–2 mol %. The biphasic solution was then left refluxing and continuously dried by azeotropic distillation for 24 hours. The solution was then cooled and to it was added solid sodium bicarbonate approx 1.0 g. Evaporation of the solvent left a mobile oil which was partitioned between ether and water 1:1 (300 ml). The organic layer was isolated and the aqueous layer extracted with 2×100 ml of diethyl ether. The combined organic layers were dried with sodium sulphate. Filtration followed by evaporation left a mobile oil, which was passed through a plug of silica. Evaporation of the eluent left the cyclic acetal as a mobile oil, (0.60 g, 45%).

¹H NMR (CDCl₃, 300 MHz) δ_H 2.34 (2H, t, J=6.8 Hz, CH₂), 2.99 (2H, t, J=6.8 Hz, CH₂), 4.18 (4H, m, 2×OCH₂), 7.27 (4H, br m, 4×Ar—H).
¹³C NMR (CDCl₃, 75.47 MHz) δ_C 28.3, 36.9 (2×CH₂), 65.2 (2×CH₂), 117.0 (O—C—O), 122.9, 125.0, 126.7, 129.3 (4×Ar—CH), 141.8, 144.1 (2×Ar—C).

Synthesis of Hydroxy Ketone 1C42

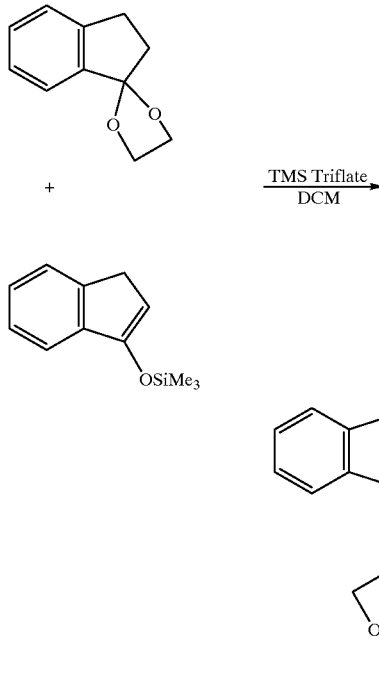

To a stirred solution of the silyl enol ether of indan-1-one (0.40 g, 1.96 mmol) and the 1,3 dioxalone of indan-1-one (0.40 g, 2.27 mmol) at −78° C. in DCM (3 ml) was added TMS triflate 20 ml. The solution was left stirring at −78° C. for 2 hours. To this solution was then added solid sodium bicarbonate approx 1 g and the mixture rapidly stirred and allowed to reach room temperature. The solution was then decanted off and passed through a plug of silica eluting with ethyl acetate: petroleum ether 1:9 grading to ethyl acetate-:petroleum ether 3:2. Evaporation of the eluent left the hydroxy ketone 1C42 as a mobile oil (0.30 g, 50.5%).
¹H NMR (CDCl₃, 300 MHz) δ_H 2.10–3.71 (11H, br m, 5×CH₂ & 2×CH), 7.19–7.30 (12H, br m, 12×Ar—H), 7.50 (2H, t, 2×Ar—H), 7.65, 7.80 (2H, d, 2×Ar—H).
¹³C NMR (CDCl₃, 75.47 MHz) δ_C 29.3, 29.6 (CH₂), 30.9 (CH₂), 32.4, 33.4 (CH₂), 48.7, 53.4 (CH), 60.3, 61.8 (OCH₂CH₂OH), 63.7, 64.7 (OCH₂CH₂OH), 89.5, 90.2 (OHCH₂CH₂OC), 123.7, 123.8, 124.6, 124.7, 125.0, 126.1, 126.2, 127.2, 127.5, 128.6, 128.9, 134.6, 134.9 (8×Ar—CH), 137.7, 141.5, 145.2, 153.5 (4×Ar—C), 206.9 (C=O).

Synthesis of 1C44

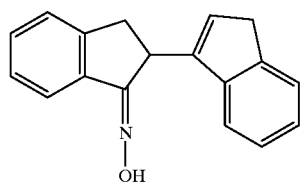

1C44

¹H NMR (CDCl₃, 300 MHz) δ_H 3.02 (1H, dd, J=2.6. 16.9 Hz, CH OF CH₂), 3.23 (2H, q, J=16.0 and 7.3 Hz, CH₂), 3.52 (1H, dd, J=8.6 and 8.6 Hz, CH of CH₂), 4.59 (1H, dd, J=8.6 and 1.4 Hz, CHCH₂), 6.08 (1H, s, C=CHCH₂), 7.16–7.40 (8H, br m, 8×Ar—H), 7.94 (1H, d, J=7.8 Hz, 1×Ar—H).
¹³C NMR (CDCl₃, 75.47 MHz) δ_C 37.2, 37.6 (2×CH₂), 39.8 (1×CH), 118.9, 123.4, 123.9, 124.9, 125.6, 126.0, 127.4, 128.0, 132.3 (9×Ar—CH and 1×C=CH), 142.7, 143.5, 144.3, 148.0 (4×Ar—C).

Coupling Reaction of the Corresponding Silyl Enol Ether of Indan-2-one to the Corresponding Dimethyl Acetal of Indan-2-one Synthesis of a Silyl Enol Ether of Indan-2-one

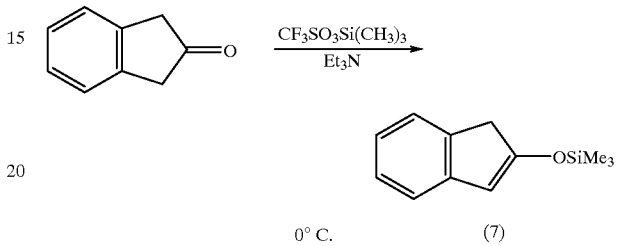

To a stirred solution of indan-2-one (1.0 g, 7.57 mmol) and triethylamine (0.84 g, 1.16 ml, 8.32 mmol) in dichloromethane at 0° C. was added trimethylsilyl trifluoromethanesulfonate (1.68 g, 1.36 ml, 7.58 mmol). The solution was left stirring at 0° C. for 15 minutes and then the solution was rapidly passed through a plug of silica, eluting with petroleum ether (b.p. 40–60° C.): ethyl acetate 100:0.5. After evaporation of the eluent the silyl enol ether was isolated as a clear colourless oil (7), 0.50 g, 77.0%.

Synthesis of Dimethyl Acetal of Indan-2-one

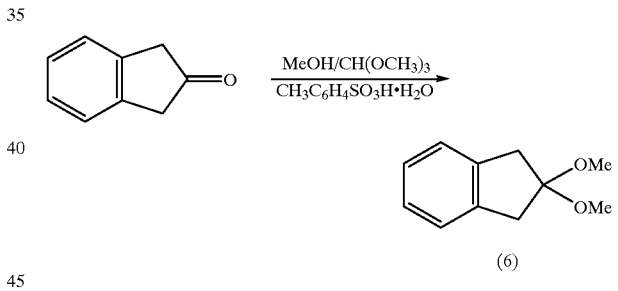

To a stirred solution of indan-2-one (1.0 g, 7.57 mmol) in methanol (12 ml) was added trimethyl orthoformate (2 ml) and p-toluenesulfonic acid (approx 1 mol %). The solution was then allowed to stir at room temperature for 2 hours. To this solution was then added solid sodium bicarbonate (approx. 0.50 g). The methanol was evaporated from the reaction mixture. The crude solid was then partitioned between ether:water (1:1) (50 ml). The organic layer was isolated and the aqueous layer extracted with ether (3×20 ml). The combined organic layers were dried with sodium sulphate. After evaporation of the solvent the crude product was then passed through a plug of silica, eluting with petroleum ether 100% grading to petroleum ether:ethyl acetate, 100:1. After evaporation of the eluent the dimethyl acetal of indan-2-one was isolated as a clear colourless oil 0.80 g, 60%.
¹H NMR (CDCl₃, 300 MHz) δ_H 3.21 (4H, s, 2×CH₂), 3.35 (6H, s, 2×OCH₃), 7.22 (4H, s, 4×Ar—H).
¹³C NMR (CDCl₃, 75.47 MHz) δ_C 41.2, 41.2 (2×CH₂), 49.4, 49.4 (2×OCH₃), 111.4 (C(OMe)₂), 124.5, 124.5, 126.5, 126.5 (4×Ar—CH), 139.8, 139.8 (2×qC).

Synthesis of 2C1

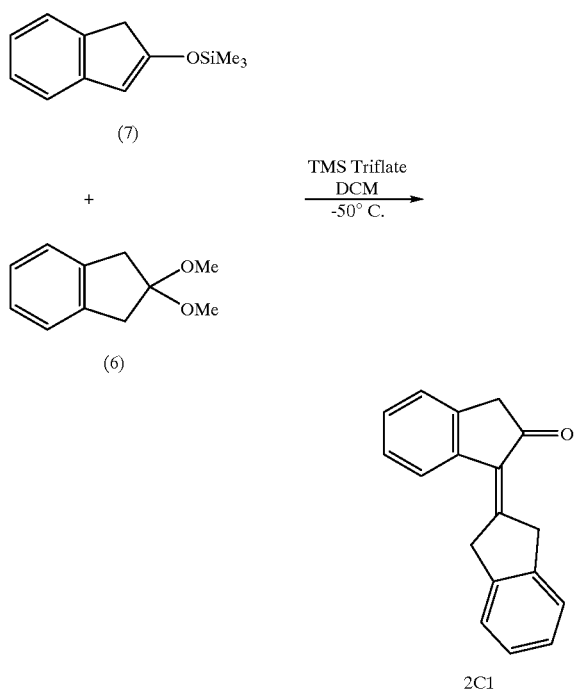

To a stirred solution of the silyl enol ether of indan-2-one (7) (0.80 g, 3.92 mmol) and the corresponding dimethyl acetal of indan-2-one (0.70 g, 3.92 mmol) in dichloromethane at −78° C., was added a catalytic amount of TMS Triflate (30 μl). The solution was left stirring at −78° C. for 3 hours and then allowed to reach −50° C. for 1 hour. To this solution was then added a 5% solution of sodium bicarbonate (approx 20 ml). The organic layer was isolated and the aqueous layer extracted with dichloromethane (2×20 ml). The combined organic layers were dried with sodium sulphate. After evaporation of the solvent, the crude product was passed through a plug of silica, eluting with petroleum ether 100% grading to petroleum ether:ethyl acetate, 100:4. After evaporation of the eluent 2C1 was isolated as a solid 0.72 g, 74.3%.

Low resolution mass spectra: Found $M^+246$.

Required $M^+246$.

$^1$H NMR (CDCl$_3$, 300 MHz) $\delta_H$ 3.45 (2H, s, C$\underline{H}_2$), 4.10 (2H, s, C$\underline{H}_2$), 4.40 (2H, s, C$\underline{H}_2$), 7.45 (8H, m, 8×Ar—H).

$^{13}$C NMR (CDCl$_3$, 75.47 MHz) $\delta_C$ 40.7, 41.2, 42.7 (3× $\underline{C}$H$_2$), 123.5, 124.3, 124.6, 125.1, 126.7, 127.0, 127.2, 127.5 (8×Ar—$\underline{C}$H), 129.6, 137.4, 139.2, 140.2, 141.1, 154.2 (4×Ar—$\underline{C}$ & 2×$\underline{C}$=C), 204.0 ($\underline{C}$=O).

Synthesis of 2C1

Potassium Tert-butoxide Method

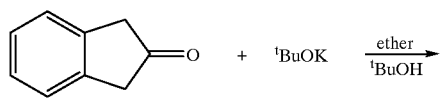

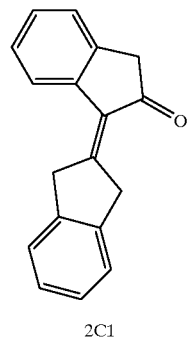

Potassium tert-butoxide (4.25 g, 37 mmol) in $^t$butanol (125 ml) and ether (10 ml) were added dropwise over 20 minutes, to a stirring solution of indan-2-one (5.0 g, 37 mmol) in ether (25 ml) and $^t$butanol (5 ml). The reaction mixture was then left stirring overnight.

The crude product was partitioned between ethyl acetate and saturated aqueous ammonium chloride. The organic layer was isolated and the aqueous phase was re-extracted with ethyl acetate. The organic layers were combined and dried over sodium sulphate. On evaporation of the solvent the crude product was obtained. Flash column chromatography was used to purify the required product (eluent:petroleum ether (b.p. 40–60° C.):ethyl acetate, 9:1). On recrystallisation with ether 2C1 was obtained as a white crystalline solid,.0 41.12%.

Low resolution mass spectra: Found $M^+246$.

Required $M^+246$.

$^1$H NMR (CDCl$_3$, 300 MHz) $\delta_H$ 3.45 (2H, s, C$\underline{H}$), 4.10 (2H, s C$\underline{H}_2$), 4.40 (2H, s, C$\underline{H}_2$), 7.45 (8H, m, 8×Ar—$\underline{H}$).

$^{13}$C NMR (CDCl$_3$, 75.47 MHz) $\delta_C$ 40.7, 41.2, 42.7, (3× $\underline{C}$H$_2$), 123.5, 124.3, 124.6, 125.1, 126.7, 127.0, 127.2, 127.5 (8 ×Ar—$\underline{C}$H), 129.6, 137.4, 139.2, 140.2, 141.1, 154.2, (4×Ar—$\underline{C}$& 2×$\underline{C}$=$\underline{C}$), 204.0 ($\underline{C}$=O).

Synthesis of 2C2

Potassium Tert-butoxide Method

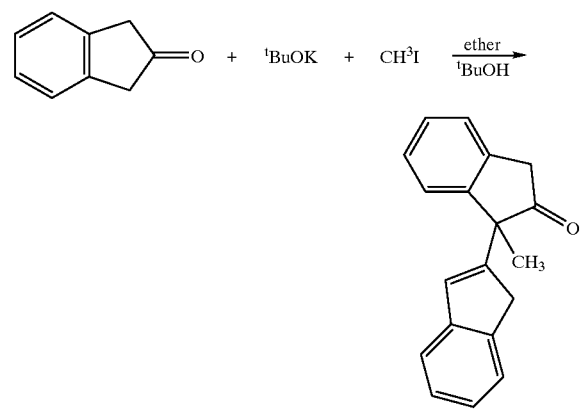

After evaporation of the eluent 2C2 was isolated as a pale yellow oil.

Low resolution mass spectra: Found $M^+260$, $M^+-15=245$

Required $M^+260$.

$^1$H NMR (CDCl$_3$, 300 MHz) $\delta_H$ 1.70 (3H, s, C$\underline{H}_3$), 3.38 (2H, br s, C$\underline{H}_2$), 3.71 (2H, ab q, J=22.5 Hz, COC$\underline{H}_2$), 6.40 (1H, br s, C$\underline{H}$), 7.17 (9H, br m, 8×Ar—$\underline{H}$).

$^{13}$C NMR (CDCl$_3$, 75.47 MHz) δ$_C$ 22.6 (CH$_3$), 38.2, 41.6 (2×CH$_2$), 57.2 (qC), 120.7, 123.5, 124.5, 124.6, 124.7, 126.3, 127.7, 127.8, 128.9 (8×Ar—CH & 1×C=CH), 135.5, 143.5, 144.1, 146.1, 149.8 (4×Ar—C & 1×CCH), 215.5 (C=O).

LDA Method

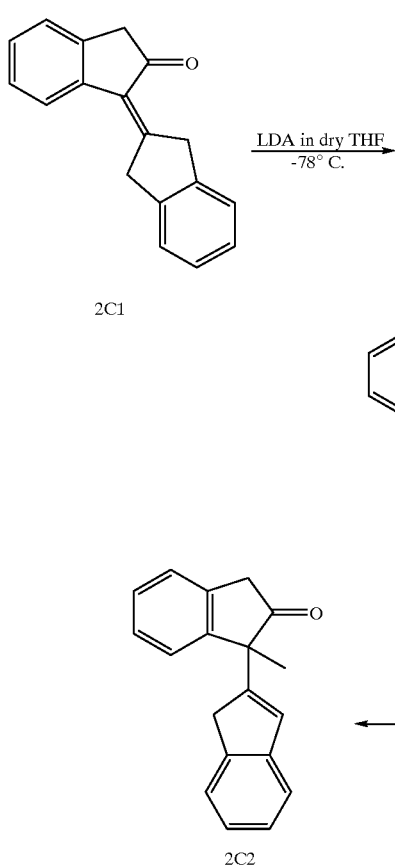

A three necked 100 ml round bottomed flask was oven dried and fitted with a septum and a nitrogen inlet line. The flask was then evacuated and heated with a heat gun to dry. To this flask, which was filled with nitrogen was added indan-2-one dimer 2C1 (500 mg, 2.0 mmol) in dry THF (25 ml). The solution was cooled to −78° C. with a liquid nitrogen/ethyl acetate bath and lithium diisoprapylamid (LDA) in THF/heptane/ethyl benzene (1.0 ml of 2M solution of LDA) was added. After stirring for 10 minutes at −78° C., iodomethane (1.14 g, 8.0 mmol, 4 equivalents) was added and the solution was allowed to warm to room temperature for 3 hours under vacuum and in a nitrogen atmosphere.

To this solution was added ether (30 ml) and aqueous ammonium chloride solution (30 ml). The organic layer was isolated and the aqueous layer was extracted with ether (2×30 ml). The combined organic extracts were dried over sodium sulphate and on evaporation of the solvent afforded an oil. The crude product was purified by flash column chromatography (eluent:petroleum ether (b.p. 40–60° C.): ethyl acetate, 9:1), to yield 2C2.

Low resolution mass spectra: Found M$^+$260, M$^+$−15=245. Required M$^+$260.

$^1$H NMR (CDCl$_3$, 300 MHz) δ$_H$ 1.70 (3H, s, CH$_3$), 3.38 (2H, s CCH$_2$) 3.68 (2H, q, J=22.5, COCH$_2$), 6.40 (1H, br s, CH), 7.17 (8H, m, 8×Ar—H). $^{13}$C NMR (CDCl$_3$, 75.47 MHz) δ$_C$ 22.6 (CH$_3$), 38.2, 41.6 (2×CH$_2$), 57.2 (qC), 120.7, 123.5, 124.5, 124.6, 124.7, 126.3, 127.7, 127.8, 128.9 (8×Ar—CH & 1×C=CH), 135.5, 143.5, 144.1, 146.1, 149.8 (4×Ar—C & 1×C=CH), 215.5 (C=O).

Synthesis of 2C3

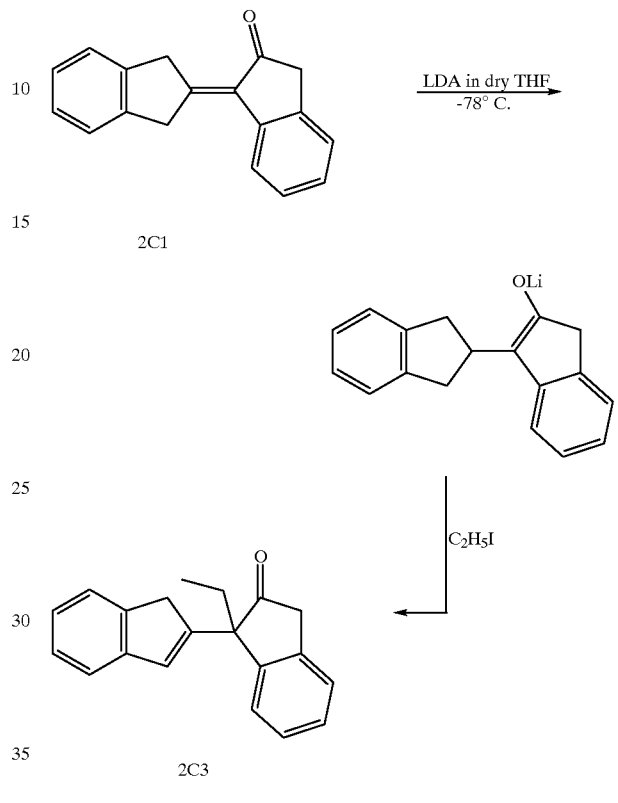

The reaction yield for 2C3 was 27 mg, 24.24%.

$^1$H NMR (CDCl$_3$, 300 MHz) δ$_H$ 0.71 (3H, t, CH$_2$CH$_3$), 2.05 & 2.40 (2H, 2×br m, CH$_2$CH$_3$), 3.40 (2H, d, HC=CC H$_2$), 3.57 (2H, ab q, COCH$_2$), 6.34 (1H, br s, CH=C), 7.25 (8H, br m, 8×Ar—H).

$^{13}$C NMR (CDCl$_3$, 75.47 MHz) δ$_C$ 9.5 (CH$_2$CH$_3$), 29.7, 38.4, 42.7 (3×CH$_2$), 62.5 (qC), 120.7, 123.6, 124.5, 124.8, 125.2, 126.3, 127.7, 127.7, 129.9 (8×Ar—CH & 1×C=CH), 136.7, 143.5, 143.9, 144.1, 149.7 (4×Ar—C & 1×C=CH), 216.1 (C=O).

Synthesis of 2C4 and 2C5

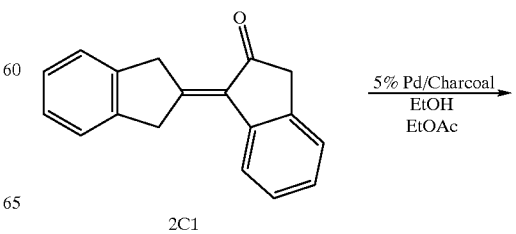

-continued

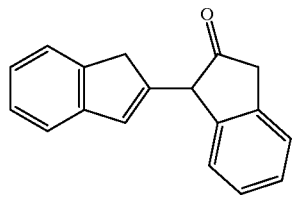

2C4

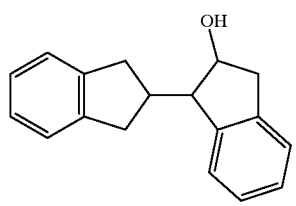

2C5

2C1 (100 mg, 0.04 mmol) was dispersed in ethanol (10 ml) and ethyl acetate (5 ml) and to this was added 5% Palladium on carbon (0.01 g). The mixture was stirred under nitrogen for 14 hours. The Palladium residues were removed by filtration and the solvent was removed to afford the crude reaction product. Flash column chromatography (eluent:petroleum spirits b.p. 40–60° C.: ethyl acetate 95:5) afforded 2C4 (83 mg, 83.0%) and 2C5 (10.0 mg, 10%).
NMR Data for 2C4
$^1$H NMR (CDCl$_3$, 300 MHz) $\delta_H$ 3.30 (2H, br s, HC=CC H$_2$), 3.69(2H, ab q, J=7.43 Hz COCH$_2$), 5.38 (1H, d, J=25.23 Hz CHCOCH$_2$), 6.94 (1H, d, J=7.47 Hz 1×Ar—H), 7.30 (8H, br m, 7×Ar—H & 1×C=CHCH$_2$).
$^{13}$C NMR (CDCl$_3$, 75.47 MHz) $\delta_C$ 37.6 & 43.5 (2×CH$_2$), 54.3 (CHC=CHCH$_2$), 120.6, 123.7, 124.7, 125.0, 125.1, 126.5, 127.5, 127.6, 136.5, (8×Ar—CH & 1×C=CH), 137.4, 141.7, 143.0, 143.4, 145.0, (4×Ar—C & 1×C=CH) 215.7 (C=O).
NMR data for 2C5
$^1$H NMR (CDCl$_3$, 300 MHz) $\delta_H$ 3.0, 3.02, 3.40 (8H, 3×br m, 3×CH$_2$ & CH—CH), 4.65 (1H, br d, J=2.19 Hz CHOH), 7.20 (7H, br m, 7×Ar—H), 7.47 (1H, ab m, 1×Ar—H).
$^{13}$C NMR (CDCl$_3$, 75.47 MHz) $\delta_C$ 38.4, 38.5 (2×CH$_2$), 39.4 (1×CH), 41.2 (CH$_2$), 55.3 (CH$_2$), 75.6 (CHOH), 124.2, 124.2, 125.1, 125.2, 126.1, 126.1, 126.6, 126.7 (8×Ar—CH), 141.3, 142.8, 143.3, 143.6 (4×Ar—C).
Synthesis of 2C6
2C6: 1-(2-indenyl)-1-prop-2-enyl-2-indanone

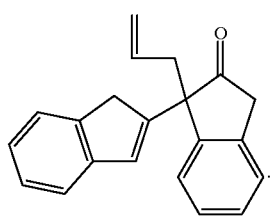

2C6

The synthesis uses the same procedure as for 2C3, but using allylbromide rather than ethyl iodide.
$^1$H NMR (CDCl$_3$, 300 MHz) $\delta_H$.
$^{13}$C NMR (CDCl$_3$, 75.47 MHz) $\delta_C$ 38.3, 41.1, 41.9, 44.2 (4×CH$_2$) 57.3, 60.2 (2×CH), 118.6, 124.5, 126.2, 127.7, 130.5, 132.8, 133.6, 133.7 (8×Ar—H) 143.0, 143.7, 143.9. 148.7 (4×Ar—C), 217.8 (C=O).
Synthesis of 2C7

Alkylation of 2C1

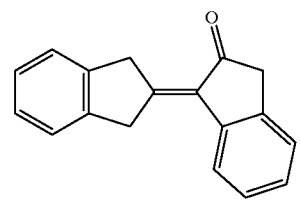

2C1

LDA in dry THF
-78° C.

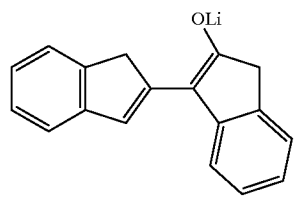

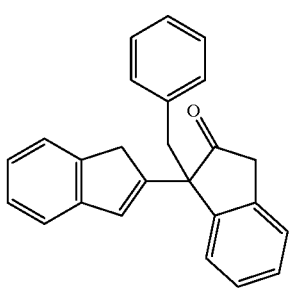

2C7

Yield (57 mg, 42%).

$^1$H NMR (CDCl$_3$, 300 MHz) $\delta_H$ 3.22–3.80 (6H, m, C H$_2$'s), 6.63 (1H, s, CH=C), 6.83–7.42 (8H, m, 8×Ar—H).

$^{13}$C NMR (CDCl$_3$, 75.47 MHz) $\delta_C$ 38.9, 42.8, 43.6 (3× CH$_2$), 63.4 (qC), 120.9, 123.6, 124.6, 124.7, 125.8, 126.3, 126.3, 126.4, 126.4, 127.4, 127.4, 127.7, 127.8, 129.5, 130.2 (13×Ar—CH & 2×C=CH), 136.1, 136.7, 143.3, 143.5, 149.2 (5×Ar—C), 216.3 (C=O).

Synthesis of 2C8

2C7 (100 mg, 0.3 mmol) was dissolved in ethyl acetate:ethanol (2:1, 10 ml) to this solution was added NaBH$_4$ (100 mg). The reaction was stirred at room temperature for 2 hrs. The product was extracted into ethyl acetate and the product was purified by flash column chromatography being isolated as a mixture of diasteriomers 2C8 (0.067 g, 66.1%).

$^1$H NMR (CDCl$_3$, 300 MHz) $\sigma_H$ 2.65–3.60 (6H, m, C H$_2$'s), 4.66 (1H, b m, CHOH), 6.75 (1H, s, C=CH), 7.00–7.39 .(13H, m, 13×Ar—H.

$^{13}$C NMR (CDCl$_3$, 75.47 MHz) $\sigma_C$ 26.9, 29.7, 39.6 (3× CH$_2$), 58.8, 60.3 (qC), 78.4, 80.4 (CHOH), 120.5, 123.4, 124.0, 125.0, 125.6, 126.0, 126.3, 126.3, 126.5, 127.3, 127.6, 127.7, 128.1, 130.3, 130.5 (13×Ar—CH & C=CH), 138.2, 139.8, 142.9, 144.7, 145.5, 152.7 (5×Ar—C & 1× C=CH).

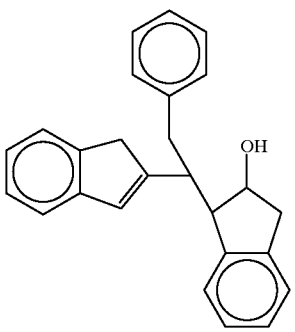

2C8

Synthesis of 2C9

Usual procedure using 10% palladium on carbon. (0.078 g, 76.5%).

$^1$H NMR (CDCl$_3$, 300 MHz) σ$_H$ 1.96 (1H, br s, CHOH), 2.55 (1H, q, J=8.13, 12.4 Hz, CHOHCH$_2$), 2.69–2.83 (2H, m, CH$_2$CHCH$_2$), 2.99 (1H, d, J=13.4 Hz, 1H of AR—CH$_2$), 3.10–3.21 (2H, m, CH$_2$CHCH$_2$), 3.19 (1H, d, J=13.4 Hz, 1H of Ar—CH$_2$), 3.28–3.36 (1H, m, CH of CHCH$_2$), 3.48–3.56 (1H, m, CH of CH$_2$CHCH$_2$), 4.66 (1H, t, J=9.9 Hz, CHOH), 6.61 (1H, d, J=7.5 Hz, Ar—CH), 6.84 (1H, t, J=2.0 Hz, Ar—CH), 7.09–7.38 (11H, m, Ar—H).

$^{13}$C NMR (CDCl$_3$, 75.47 MHz) σ$_C$ 34.0, 35.3, 38.2, 39.3 (4×CH$_2$), 42.7 (CH), 55.4 (qC), 75.7 (CHOH), 124.3, 124.3, 124.3, 125.7, 125.8, 125.9, 126.2, 126.8, 127.4, 131.0, 131.0, (13×Ar×CH), 139.1, 143.1, 145.4 (5×Ar—C).

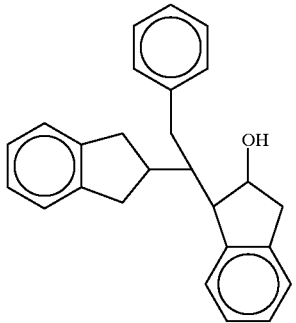

2C9

Synthesis of 2C10

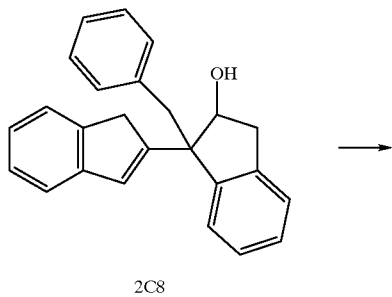

2C8

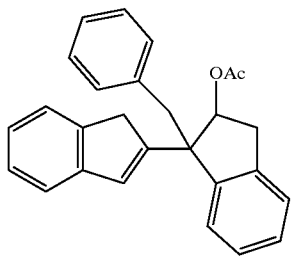

2C10

2C8 (100 mg, 0.3 mmol) was dispersed in clean dry DCM (5 ml) to this was added triethylamine (0.1 ml), acetic anhydride (0.25 ml) and DMAP (0.05 g). The reaction was stirred at room temperature for 15 minutes. The crude reaction mixture was then passed through a column, eluting with petroleum ether:ethyl acetate, 9:1.

$^1$H NMR (CDCl$_3$, 300 MHz) σ$_H$ 2.34 (3H, 2×s, COCH), 2.89–3.65 (6H, m, 3×CH$_2$), 5.75 (1H, m, CHOAc), 6.93 (1H, t, J=2.2 Hz, C=CH), 6.95–7.52 (13H, m, Ar—CH).

$^{13}$C NMR (CDCl$_3$, 75.47 MHz) σ$_C$ 20.6, 21.0 (COCH$_3$), 36.8, 37.4, 39.1, 39.4, 40.4, 40.6 (3×CH$_2$), 57.2, 58.7 (qC), 79.40, 80.9 (CHOH), 120.4, 120.5, 123.2, 123.3, 124.1, 124.2, 124.5, 124.7, 125.5, 125.9, 126.0, 126.1, 126.2, 126.4, 126.6, 127.3, 127.3, 127.4, 127.5, 127.8, 127.7, 128.4, 128.4, 129.5, 129.8, 130.3, 130.8 (13×Ar—CH), 136.8, 137.5, 139.5, 140.2, 140.7, 142.8, 143.3, 144.3, 144.9, 145.1, 150.6, 151.7 (5×Ar—C and 1×C=CH), 170.1, 170.2 (COCH$_3$).

Synthesis of 2C11 and 2C15

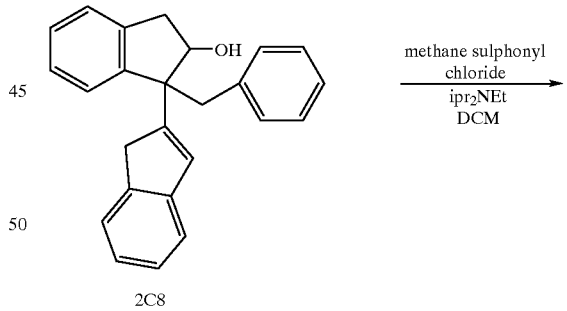

2C8

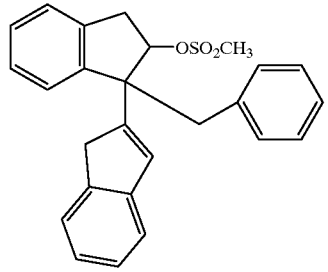

2C15

+

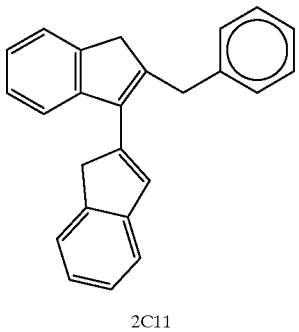

2C11

To an iced cooled solution of 2C8 (0.10 g, 0.295 mmol) was added methane sulphonyl chloride (37.3 mg, 0.325 mmol) as a solution in DCM (1 ml). To this solution was then added dropwise a solution of diisopropyl ethylamine (42.0 mg, 0.325 mmol) in DCM l(1 ml). The reaction solution was allowed to stir at 0° C. for 1 hour. The solution was then loaded on to a column of flash silica. The product mesylate was eluted out with petroleum spirits:ethyl acetate 9:1. Evapaporation of the eluent left the mesylate 2C15 as a mobile oil (0.11 g, 89%). 2C11 was isolated as a side product in the reaction.

Synthesis of 2C12

Coupling of 3-Bromo Indan-1-one to the Silyl Enol Ether of Indan-1-one

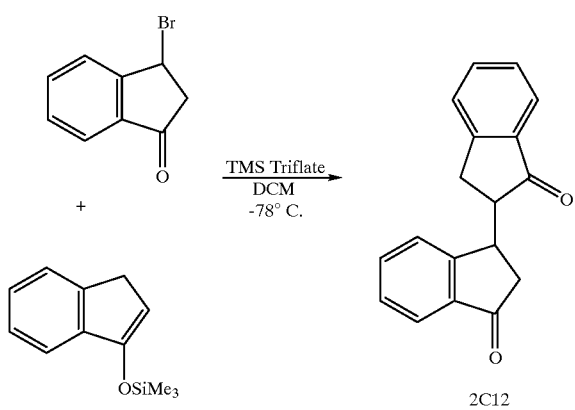

2C12

To a stirred solution of the silyl enol ether of indan-1-one (0.8 g, 3.92 mmol) and the corresponding 3-Bromo indan-1-one (0.82 g, 3.92 mmol) in dichloromethane at −78° C., was added a catalytic amount of TMS Triflate (30 μl). The solution was left stirring at −78° C. for 10 min and at room temperature for 3 hours. To this solution was then added solid sodium bicarbonate (approx 2 g) and the solution was stirred rapidly for 10 minutes. The solution was then filtered and the filtrate was evaporated to leave a mobile oil which was passed through a plug of silica elutant with petroleum ether:ethyl acetate, 9:2. After evaporation of the eluent, 2C12 was obtained as a yellow solid, 38%.

Low resolution mass spectra: Found M$^+$262 Require M$^+$262

$^1$H NMR (CDCl$_3$, 300 MHz) δ$_H$ 1.91 (1H, dd, J=3.3 Hz, CH of CH$_2$), 235 (1H, dd, J=4.05 Hz, CH of CH$_2$), 2.65 (1H, dd, J=7.8 Hz, CH of CH$_2$), 2.89 (1H, dd, CH of CH), 3.36 & 4.22 (2H, 2×m, 2×CHCH), 7.38 (3H, m, 3×Ar—H), 7.53 (1H, dd, J=1.2 Hz, 1×Ar—H), 7.60 (2H, m, 2×Ar—H), 7.75 (2H, 2×t, J=1.2 Hz, 2×Ar—H).

$^{13}$C NMR (CDCl$_3$, 75.47 MHz) δ$_C$ 27.6, 37.9 (2×CH$_2$), 37.7, 49.7 (2×CH), 123.6, 123.9, 125.1, 126.5, 127.6, 127.9, 135.0, 135.1, (8×Ar—CH), 136.6, 137.3, 153.7, 156.4 (4×Ar—C), 205.1, 206.5 (2×C=O).

Synthesis of 2C14

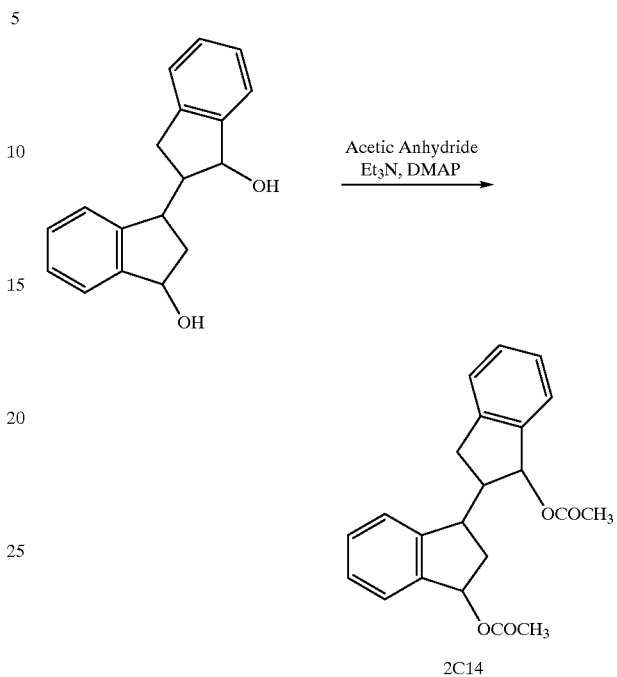

2C14

The resultant alcohol from the sodium borohydride reduction of 2C12 (200 mg, 0.75 mmol) was dissolved in clean, dry DCM (5 ml). To this solution was added triethylamine (0.36 ml), DMAP (0.1 g) and acetic anhydride (0.25 ml, 10 equivalents). The reaction mixture was stirred at room temperature for 15 minutes and passed through a plug of silica eluting with petroleum spirit (b.p. 40–60° C.):ethyl acetate (8:2) to afford 2C14 (140 mg, 53.3%).

$^1$H NMR (CDCl$_3$, 300 MHz) δH 1.94–2.06 (1H, m, CH of CH$_2$), 2.07 (3H, s, OCOCH$_3$), 2.08 (3H, s, OCOCH$_3$), 2.70–3.00 (4H, m, CH, CH$_2$ CH of CH$_2$), 3.54–3.62 (1H, m, CHCH$_2$CHO), 6.17 (1H, t, J=2.85 Hz, CH$_2$CHO), 6.32 (1H, d, J=5.7 Hz, CHCHO), 7.21–7.52 (8H, m, Ar—CH)

$^{13}$CNMR (CDCl$_3$, 75.47 MHz) δ$_C$ 22.4, 22.4 (2×COCH$_3$), 34.7, 36.7 (2×CH$_2$), 41.9, 48.5 (2×CH), 76.8, 77.6 (2×CHOCOCH$_3$), 124.0, 124.4, 125.4, 126.3, 126.6, 127.1, 129.0, 129.1 (8×Ar—CH), 140.9, 141.3, 143.7, 145.9 (4×Ar—C), 170.8, 170.9 (2×COCH$_3$)

Synthesis of 2C16

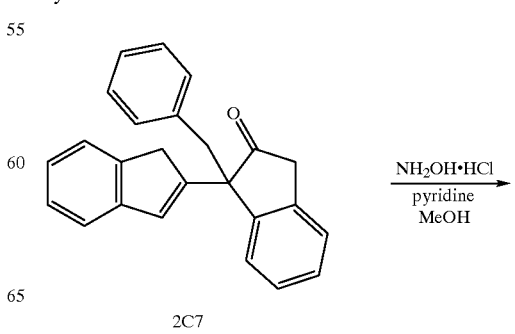

2C7

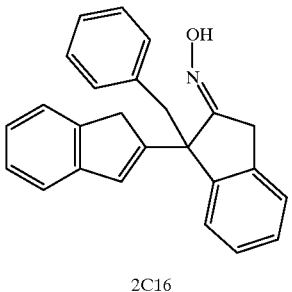

2C16

2C7 (100 mg) was dissolved in pyridine (0.5 ml) and to this was added hydroxylamine hydrochloride (300 mg) and methanol (3 ml) was added. The solution was then allowed to reflux for 1 hour. The reaction was then quenched with 2M aqueous HCl (10 ml) and the product was extracted into ether and dried with Na2SO4. The crude reaction mixture was then passed through a flash silica column, eluting with petroleum ether:ethyl acetate, 8:2. On evaporation of the desired eluent 2C16 was obtained as a mixture of syn and anti isomers (80 mg).

$^1$H NMR (CDCl$_3$, 300 MHz) $\sigma_H$ 2.86–3.76 (6H, br m, 3×C$\underline{H}_2$), 6.80–7.36 (14H, br m, 13×Ar—H, 1×C=C$\underline{H}$).

$^{13}$C NMR (CDCl$_3$, 75.47 MHz) $\sigma_C$ 33.7, 33.9 ($\underline{C}$H$_2$), 39.1, 41.4 ($\underline{C}$H$_2$), 46.3, 47.7 ($\underline{C}$H$_2$), 58.1, 58.6 (qC), 120.9, 123.5, 124.4, 124.6, 124.7, 124.8, 126.0, 126.1, 126.3, 126.4, 127.1, 127.1, 127.1, 127.3, 127.5, 127.8, 130.4, 130.4, 130.4 (Ar—$\underline{C}$H and C=$\underline{C}$H), 136.7, 137.2, 138.5, 138.7, 143.5, 144.0, 144.5, 145.2, 152.8 (Ar—$\underline{C}$O, 167.4, 167.7 ($\underline{C}$=N—OH).

Coupling reaction of the corresponding silyl enol ether of indan-1-one to the corresponding dimethyl acetal of indan-2-one.

Synthesis of a Silyl Enol Ether of Indan-1-One

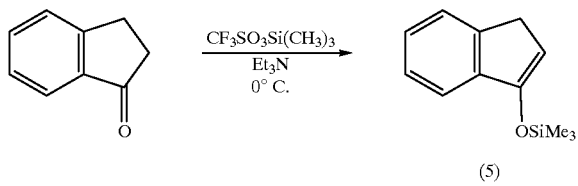

(5)

To a stirred solution of indan-1-one (1.0 g, 7.57 mmol) and triethylamine (0.84 g, 1.16 ml, 8.32 mmol) in dichloromethane at 0° C. was added trimethylsilyl trifluoromethanesulfonate (1.68 g, 1.36 ml, 7.58 mmol). The solution was left stirring at 0° C. for 15 minutes and then the solution was rapidly passed through a plug of silica, eluting with petroleum ether (b.p. 40–60° C.):ethyl acetate 100:0.5. After evaporation of the eluent the silyl enol ether was isolated as a clear colourless oil (5) (1.0 g, 77.0%).

Synthesis of Dimethyl Acetal of Indan-2-one

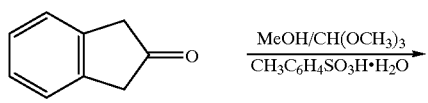

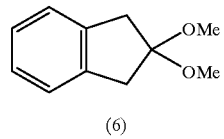

(6)

To a stirred solution of indan-2-one (1.0 g, 7.57 mmol) in methanol (12 ml) was added trimethyl orthoformate (2 ml) and p-toluenesulfonic acid (approx 1 mol %). The solution was then allowed to stir at room temperature for 2 hours. To this solution was then added solid sodium bicarbonate (approx. 0.50 g). The methanol was evaporated from the reaction mixture. The crude solid was then partitioned between ether:water (1:1) (50 ml). The organic layer was isolated and the aqueous layer extracted with ether (3×20 ml). The combined organic layers were dried with sodium sulphate. After evaporation of the solvent the crude product was then passed through a plug of silica, eluting with petroleum ether 100% grading to petroleum ether:ethyl acetate, 100:1. After evaporation of the eluent the dimethyl acetal of indan-2-one was isolated as a clear colourless oil (0.80 g, 60%).

$^1$H NMR (CDCl$_3$, 300 MHz) $\delta_H$ 3.21 (4H, s, 2×C$\underline{H}_2$), 3.35 (6H, s, 2×☐OC$\underline{H}_3$), 7.22 (4H, s, 4×Ar—$\underline{H}$).

$^{13}$C NMR (CDCl$_3$, 75.47 MHz) $\delta_C$ 41.2, 41.2 ($\underline{C}$H$_2$), 49.4, 49.4 (2×O$\underline{C}$H$_3$), 111.4 ($\underline{C}$(OMe)$_2$), 124.5, 124.5, 126.5, 126.5 (4×Ar—$\underline{C}$H), 139.8, 139.8 (2×q$\underline{C}$).

Synthesis of 3C1

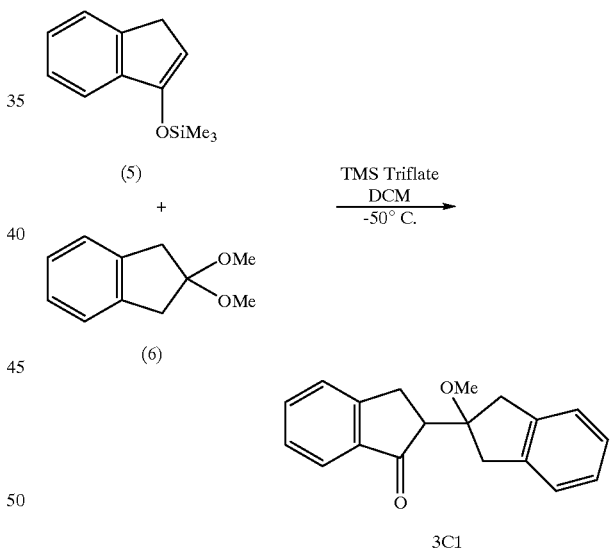

3C1

To a stirred solution of the silyl enol ether of indan-1-one (5) (0.80 g, 3.92 mmol) and the corresponding dimethyl acetal of indan-2-one (0.70 g, 3.92 mmol) in dichloromethane at −78° C., was added a catalytic amount of TMS Triflate. The solution was left stirring at −78° C. for 3 hours and then allowed to reach −50° C. for 1 hour. To this solution was then added a 5% solution of sodium bicarbonate (approx 20 ml). The organic layer was isolated and the aqueous layer extracted with dichloromethane (2×20 ml). The combined organic layers were dried with sodium sulphate. After evaporation of the solvent, the crude product was passed through a plug of silica, eluting with petroleum ether 100% grading to petroleum ether:ethyl acetate, 100:4. After evaporation of the eluent 3C1 was isolated as a slightly coloured oil (0.50 g, 50.5%). On addition of ether to the oil 3C1 crystallised out as white crystals.

$^1$H NMR (CDCl$_3$, 300 MHz) δ$_H$ 3.06 (3H, s, OCH$_3$), 3.10 (1H, m, CH), 3.37 (2H, q, J=17, CHCH$_2$), 3.21 (2H, s C—CH$_2$), 3.30 (2H, br t, CH$_2$), 7.16 (4H, m, 4×Ar—H), 7.57 (1H, t, 1×Ar—H), 7.59 (1H, d, 1×Ar—H), 7.59 (1H, t, 1×Ar—H), 7.73 (1H, d, 1×Ar—H).

$^{13}$C NMR (CDCl$_3$, 75.47 MHz) δ$_C$: 29.7, 40.6, 41.7 (3×CH$_2$), 51.1 (CH), 53.5 (OCH$_3$), 87.4 (qC), 123.9, 124.1, 124.3, 126.4, 126.49, 126.52, 127.2, 134.7 (8×Ar—CH), 137.7, 140.9, 141.5, 153.7 (4×Ar—C), 206.3 (C=O).

Synthesis of 3C2

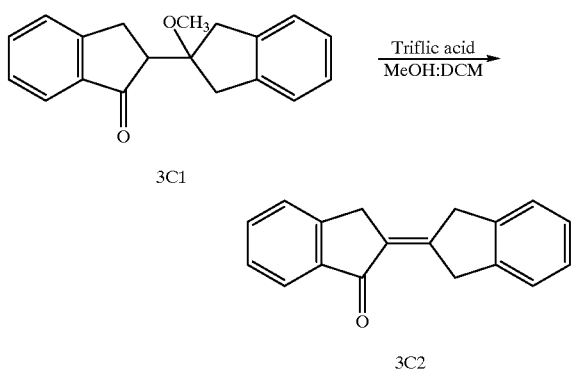

3C1 (200 mg, 0.689 mmol) was dissolved in methanol (3 ml) and DCM (1 ml), to this stirring solution triflic acid (45 µl) was added. The reaction mixture was allowed to reflux for 1 hour, a precipitate formed. The solution was then cooled in an ice bath, filtered and the solid was dried. Analysis of this yellow solid provided to be 3C2 (100 mg, 50%).

$^1$H NMR (CDCl$_3$, 300 MHz) δ$_H$ 3.65, 3.90, 4.40 (6H, 3×br s, 3×CH$_2$), 7.20 (2H, m, 2×Ar—H), 7.35 (3H, m, 3×Ar—H), 7.52 (2H, m, 2×Ar—H), 7.84 (1H, d, J=7.7 Hz, 1×Ar—H).

$^{13}$C NMR (CDCl$_3$, 75.47 MHz) δC 31.9, 39.3, 40.2 (3×CH$_2$), 123.8, 124.4, 124.9, 126.1, 126.6, 126.9, 127.3, 135.4 (8×Ar—CH), 129.1, 139.1, 139.7, 142.2, 148.4, 154.8 (4×Ar—C& 2×C=C), 193.5 (C=O).

Preparation of 3C3 m, CH=CH$_2$), 6.69 (1H, s, C=CHCH$_2$), 7.05–7.30 (3H, m, 3×Ar—H), 7.34–7.42 (2H, m, 2×Ar—H), 7.48–7.56 (1H, dd, J=0.87 Hz, 7.3 Hz, 1×Ar—H), 7.56–7.67 (1H, m, 1×Ar—H), 7.71–7.79 (1H, m, 1×Ar—H).

$^{13}$C NMR (CDCl$_3$, 75.47 MHz) δ$_C$ 38.3, 38.6, 41.3 (3×CH$_2$), 55.8 (qC), 118.7 (CH=CH$_2$), 120.5, 123.4, 124.7, 126.3, 127.6, 127.9, 133.7, 135.1, 135.3 (8×Ar—CH & 1×CH=CH$_2$), 143.2, 144.2, 148.9, 152.5 (4×Ar—C), 205.9 (C=O).

Synthesis of 3C4
Reduction of 3C3

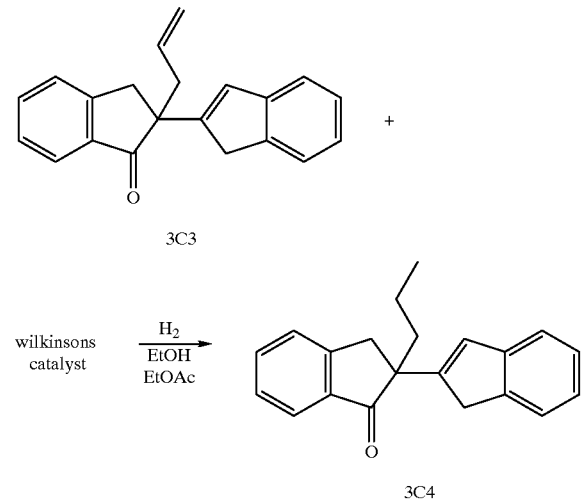

3C3 (100 mg, 0.351 mmol) was dissolved in ethanol (20 ml) and ethyl acetate (10 ml). To this stirring solution Wilkinsons catalyst (0.1 g) was added. The reaction mixture was then stirred under hydrogen for 20 hours. An additional quantity of Wilkinsons catalyst (200 mg) was then added. The reaction was allowed to stir under hydrogen for a further 12 hours. The solvent was then removed and the crude product was purified by flash column chromatography to yield 3C4 (90 mg, 90%).

$^1$H NMR (CDCl$_3$, 300 MHz) δ$_H$ 1.00 (3H, t, J=1.6 Hz, CH$_2$CH$_2$CH$_3$), 1.33 (2H, m, CH$_2$CH$_2$CH$_3$), 1.90 (1H, m, CH of CH$_2$CH$_2$CH$_3$), 2.10 (1H, m, CH of CH$_2$CH$_2$CH$_3$), 3.45

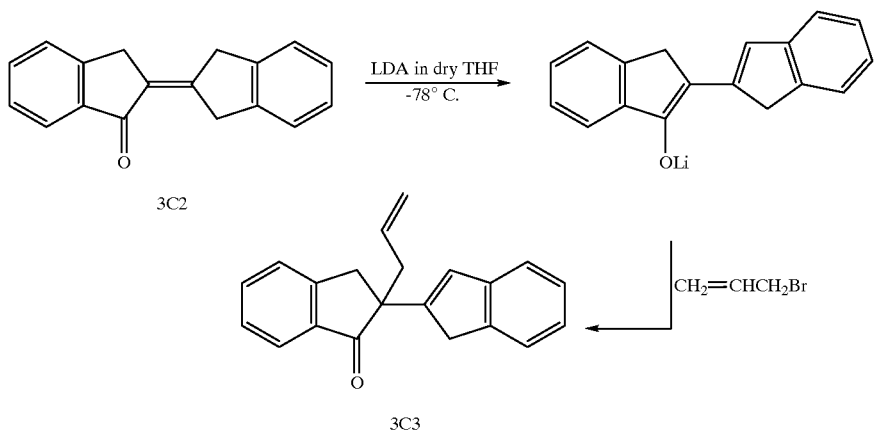

$^1$H NMR (CDCl$_3$, 300 MHz) δ$_H$ 2.62–2.90 (2H, m, CH$_2$=CHCH$_2$) , 3.28–3.68 (4H, m, 2×CH$_2$), 4.99–5.21 (2H, (2H, ab q, CH=C—CH$_2$), 3.54 (2H, ab q, J=17.7 Hz, C—CH$_2$), 6.71 (1H, s, CH=C—CH$_2$), 7.14 (1H), dt, J=1.5 Hz &

5.7 Hz, Ar—H), 7.25 (2H, br m, 2×Ar—H), 7.36 (2H, br t, 2×Ar—H), 7.52 (1H, br d, Ar—H), 7.63 (1H, dt, J=1.0 Hz, 7.9 Hz, Ar—H), 7.77 (1H, br d, J=7.7 Hz, Ar—H).

$^{13}$C NMR (CDCl$_3$, 75.47 MHz) $\delta_C$ 14.5 (CH$_3$), 18.3, 38.6, 39.0, 39.5 (4×CH$_2$), 56.5 (qC), 120.5, 123.5, 124.7, 125.1, 126.2, 126.2, 127.0, 127.7, 134.9 (8×Ar—CH & 1×C═CH), 135.5, 143.3, 144.4, 149.5, 152.5 (4×Ar—C & 1×CH═C), 206.6 (C═O).

Synthesis of 3C5

Alkylation of 3C1

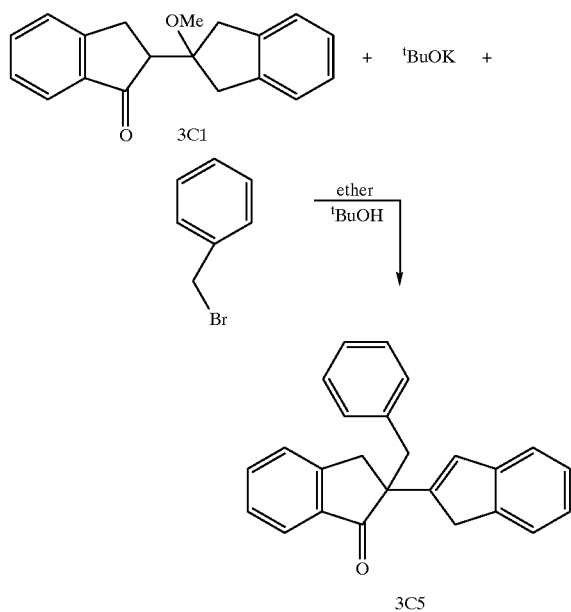

3C1 (400 mg, 1.44 mmol) was dissolved in ether (12 ml) and $^t$butanol (2 ml), to this benzyl bromide (1.0 g, 0.66 ml, 5.76 mmol) was added. To this stirring solution, potassium tert-butoxide (160 mg, 1.44 mmol) in $^t$butanol (7 ml) was added dropwise over 20 minutes. The solution was allowed to stir for 3 hours. To this solution saturated aqueous ammonium chloride solution (20 ml) was added and the organic phase was extracted with ether (2×50 ml). The organic layers were combined, dried and the crude product was purified by flash column chromatography to yield 3C5 (388 mg, 80%).

$^1$H NMR (CDCl$_3$, 300 MHz) $\delta_H$ 3.48 (2H, ab q, J=13.0 Hz, CH$_2$), 3.45 (2H, d, J=7.4Hz, CH$_2$), 3.65 (2H, d, CH$_2$), 6.78 (1H, d, J=0.7 Hz, CH═C), 7.22–7.45 (11H, br m, 11×Ar—H), 7.54 (1H, dt, J=1.2 Hz & 7.6 Hz, Ar—H), 7.81 (1H, d, J=7.2 Hz, Ar—H)

$^{13}$C NMR (CDCl$_3$, 75.47 MHz) $\delta_C$ 37.5, 38.8, 42.2 (3× CH$_2$), 57.2 (qC) , 120.5, 123.4, 124.1, 124.3, 124.5, 125.9, 126.2, 126.4, 127.4, 128.1, 128.3, 129.9, 134.8, (13×Ar—CH & 1×C═CH), 135.1, 137.3, 143.1, 144.1, 149.1, 152.4 (5×Ar—C & 1×C═CH), 205.9 (C═O).

Synthesis of 3C6 & 3C7

Sodium Borohydride Reduction of 3C5

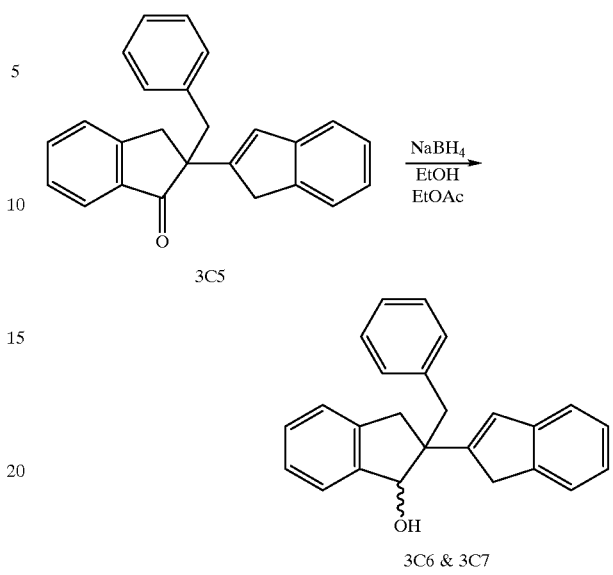

3C5 (0.50 g, 1.48 mmol) was dissolved in ethyl acetate:ethanol (2:1, 21 ml) and sodium borohydride (0.50 g, 13.15 mmol) was added to the reaction. The reaction was stirred at room temperature for 3 hours. Evaporation of the solvent left a white solid to which was added DCM (2 ml) and the slurry passed through a plug of silica, eluting with petroleum spirit (b.p. 40–60° C.):ethyl acetate, 100:1. The first pair of enantiomers 3C6 were eluted and evaporation of the solvent gave a white solid (0.24 g, 96%). The second pair of enantiomers 3C7 were then eluted and evaporation of the solvent gave a mobile oil (0.24 g, 96%).

3C6

$^1$H NMR (CDCl$_3$, 300 MHz) $\delta_H$ 2.99 (2H, dd, CH$_2$), 3.21 (2H, dd, CH$_2$), 3.45 (2H, ab q, CH$_2$), 5.05 (1H, m, CHOH), 6.68 (1H, s, J=0.5 Hz, CH═C—CH$_2$), 6.96 (2H, m, 2×Ar—H), 7.16–7.45 (11H, br m, 11×Ar—H).

$^{13}$C NMR (CDCl$_3$, 75.47 MHz) $\delta_C$ 38.4, 40.4, 43.4 (3× CH$_2$) 56.4 (1×qC), 81.8 (1×CHOH), 120.6, 123.5, 124.3, 124.9, 125.0, 126.3, 126.3, 126.9, 128.0, 128.0, 128.7, 130.2, 130.2, 130.4 (13×Ar—CH & 1×C═CH), 138.1, 141.7, 143.3, 143.7, 144.5, 151.0 (5×Ar—C & 1×C═CH).

3C7

$^1$H NMR (CDCl$_3$ 300 MHz) $\delta_H$ 2.32 (1H, br m, CHOH), 2.75 & 3.20 (2H, dd, J=13.4 Hz, CH$_2$), 3.17 (2H, ab q, J=15.7 Hz, CH$_2$), 3.55 (2H, ab q, J=22.6 Hz, CH$_2$), 5.25 (1H, br s, CHOH), 6.52 (1H, d, J=0.4 Hz, C═CH), 6.91 (2H, dd, 2×Ar—H), 7.20 (4H, br m, 4×Ar—H0, 7.30 (5H, br m, 5×Ar—H), 7.50 (2H, br m, 2×Ar—H).

$^{13}$C NMR (CDCl$_3$, 75.47 MHz) $\delta_C$ 29.9, 39.9, 40.4 (3× CH$_2$), 55.8 (qC), 83.8 (CHOH), 120.4, 123.5, 123.9, 124.0, 124.9, 126.0, 126.3, 126.8, 127.7, 127.9, 128.3, 128.6, 130.1, 130.4 (13×Ar—CH & 1×C═CH), 138.3, 140.6, 142.9, 143.8, 144.7, 153.2 (5×Ar—C & 1×C═CH).

Synthesis of 3C8 & 3C9 by Reduction with Lithium Tri-tert-butoxyaluminohydride

Synthesis of 3C10

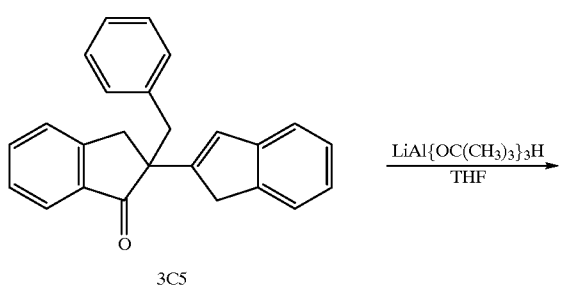

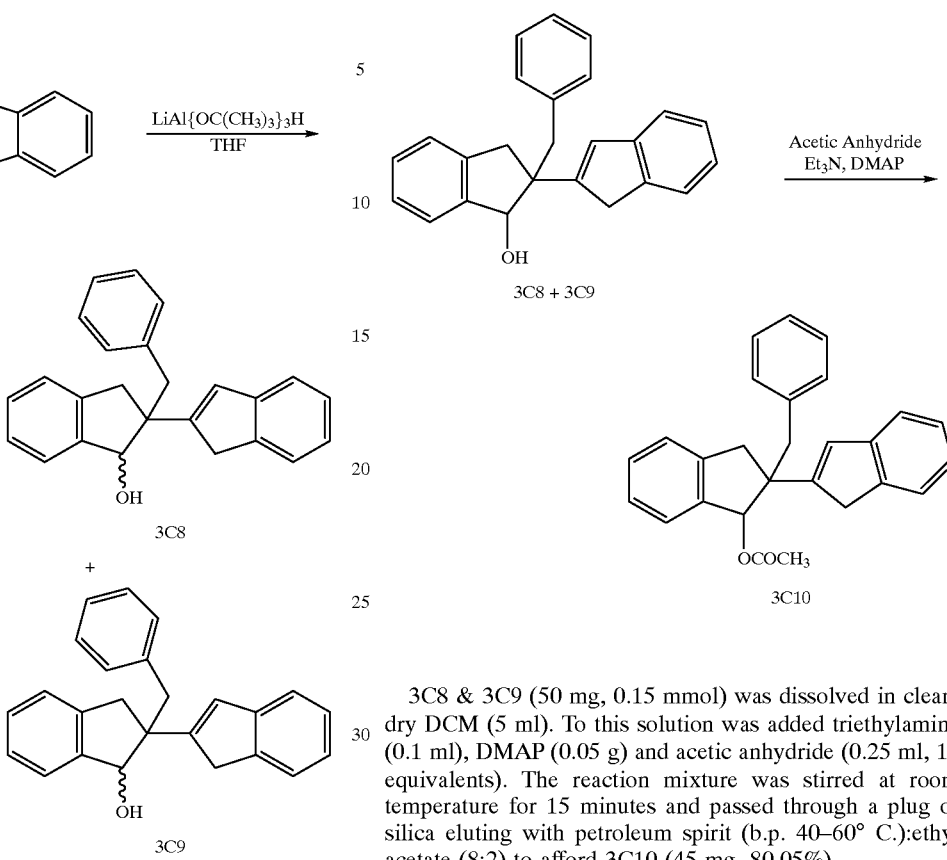

3C8 & 3C9 (50 mg, 0.15 mmol) was dissolved in clean, dry DCM (5 ml). To this solution was added triethylamine (0.1 ml), DMAP (0.05 g) and acetic anhydride (0.25 ml, 10 equivalents). The reaction mixture was stirred at room temperature for 15 minutes and passed through a plug of silica eluting with petroleum spirit (b.p. 40–60° C.):ethyl acetate (8:2) to afford 3C10 (45 mg, 80.05%).

$^1$H NMR (CDCl$_3$, 300 MHz) δH 2.24 (3H, s, COC$\underline{H}_3$), 3.05–3.40 (6H, m, 3×C$\underline{H}_2$), 6.40, 6.53 (2H, 2×s, C=C$\underline{H}$ and C$\underline{H}$OCOCH$_3$), 6.93–6.95 (2H, m, 2×Ar—$\underline{H}$), 7.13–7.17 (11H, m, 11×Ar—$\underline{H}$)

$^{13}$C NMR (CDCl$_3$, 75.47 MHz) δ$_C$ 21.3 (OCO$\underline{C}$H$_3$), 39.6, 40.6, 40.7 (3×$\underline{C}$H$_2$), 54.4 (q$\underline{C}$), 82.8 ($\underline{C}$HOCOCH$_3$), 120.5, 123.4, 124.2, 124.5, 125.7, 126.2, 126.3, 126.8, 127.9, 127.9, 128.9, 128.9, 129.4, 129.9, (13×Ar—$\underline{C}$H, vinylic $\underline{C}$H), 138.1, 140.6, 142.5, 142.7, 144.5, 151.8, (5×Ar—$\underline{C}$ and 1×$\underline{C}$H=CH$_2$), 170.8 (O$\underline{C}$OCH$_3$)

Synthesis of 3C11

Alkylation of 3C1

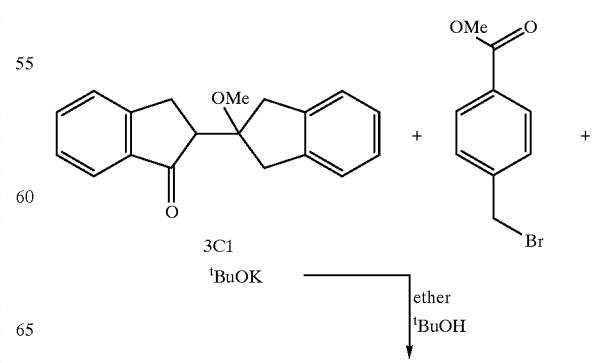

3C5 (200 mg, 0.593 mmol) was dissolved in dry THF (5 ml) and to this was added lithium tri-tert-butoxyaluminohydride (0.50 g, 1.97 mmol). The solution was allowed to stir for 3 hours. The solvent was removed and the crude reaction mixture was filtered and purified by flash column chromatography to yield 3C8 (90 mg, 96%) and 3C9 (90 mg, 96%).

3C8

$^1$H NMR (CDCl$_3$, 300 MHz) δ$_H$ 2.99 (2H, dd, J=13.7 Hz, C$\underline{H}_2$), 3.21 (2H, t, J=4.4 Hz, C$\underline{H}_2$), 3.45 (2H, abq, J=22.6 Hz, C$\underline{H}_2$), 5.05 (1H, m, C$\underline{H}$OH), 6.68 (1H, s, C$\underline{H}$=C—CH$_2$), 6.96 (2H, m, 2×Ar—$\underline{H}$), 7.16–7.45 (11H, br m, 11×Ar—$\underline{H}$).

$^{13}$C NMR (CDCl$_3$, 75.47 MHz) δ$_C$ 38.4, 40.4, 43.4 (3× $\underline{C}$H$_2$), 56.4 (q$\underline{C}$), 81.8 (1×$\underline{C}$HOH), 120.6, 123.5, 124.3, 124.9, 125.0, 126.3, 126.3, 126.9, 128.0, 128.0, 128.7, 130.2, 130.2, 130.4, (13×Ar—$\underline{C}$H & 1×C=$\underline{C}$H), 138.1, 141.7, 143.3, 143.7, 144.5, 151.0 (5×Ar—$\underline{C}$ & 1×$\underline{C}$=CH).

3C9

$^1$H NMR (CDCl$_3$, 300 MHz) δ$_H$ 2.32 (1H, br m, CHO$\underline{H}$), 2.99 (2H, dd, J=13.4 Hz, CH=C—C$\underline{H}_2$), 3.17 (2H, ab q, J=15.7 Hz, C$\underline{H}_2$), 3.55 (2H, ab q, J=22.6 Hz, C$\underline{H}_2$), 5.25 (1H, br s, C$\underline{H}$OH), 6.52 (1H, d, J=0.4 Hz, C=C$\underline{H}$), 6.91 (2H, dd, 2×Ar—$\underline{H}$), 7.20 (4H, br m, 4×Ar—$\underline{H}$), 7.30 (5H, br m, 5×Ar—$\underline{H}$), 7.50 (2H, br m, 2×Ar—$\underline{H}$).

$^{13}$C NMR (CDCl$_3$, 75.47 MHz) δ$_C$ 38.4, 38.5, 40.0 (3× $\underline{C}$H$_2$), 55.8 (q$\underline{C}$), 83.8 ($\underline{C}$HOH), 120.4, 123.5, 123.9, 124.0, 124.9, 126.0, 126.3, 126.8, 127.7, 127.9, 128.3, 128.6, 130.1, 130.4 (13×Ar—$\underline{C}$H & 1×C=$\underline{C}$H), 138.3, 140.6, 142.9, 143.8, 144.7, 153.2 (5×Ar—$\underline{C}$ & 1×$\underline{C}$=CH).

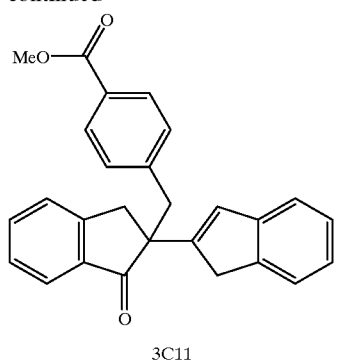

3C11

3C1 (200 mg, 0.719 mmol) was dissolved in ether (6 ml) and $^t$butanol (1 ml), to this solution methyl-4-(bromomethyl)benzoate (660 mg, 2.88 mmol) was added. Potassium tert-butoxide (80 mg, 0.719 mmol) was dissolved in $^t$BuOH (6 ml) and ether (1 ml). The $^t$BuOK solution was added over a period of 3 hours. The solution was allowed to stir for a further 2 hours. To this solution, aqueous ammonium chloride (20 ml) was added. The organic phase was extracted with ether and the crude reaction mixture was purified by flash column chromatography to yield 3C11 (230 mg, 82%).

$^1$H NMR (CDCl$_3$, 300 MHz) $\delta_H$ 3.29–3.61 (6H, m, 3×C$\underline{H}_2$), 3.84 (3H, s, CO$_2$C$\underline{H}_3$), 6.73 (1H, br s, C$\underline{H}$=CCH$_2$), 7.14 (1H, dt, J=1.5 Hz & 7.2 Hz, Ar—$\underline{H}$), 7.20 (6H, m, 6×Ar—$\underline{H}$), 7.35 (1H, d, J=7.6 Hz, 1×Ar—$\underline{H}$), 7.53 (1H, dt, J=1.2 Hz, & 7.4 Hz, Ar—$\underline{H}$), 7.75 (1H, d, J=7.6 Hz, Ar—$\underline{H}$), 7.85 (2H, d, 2×Ar—$\underline{H}$).

$^{13}$C NMR (CDCl$_3$, 75.47 MHz) $\delta_C$ 37.5, 38.7, 42.1 (3×$\underline{C}$H$_2$), 51.8 (CO$_2\underline{C}$H$_3$), 56.9 (q$\underline{C}$), 120.6, 123.4, 124.5, 124.6, 126.0, 126.3, 127.6, 128.3, 128.5, 129.3, 129.3, 129.9, 129.9, 135.0, (12×Ar—$\underline{C}$H & 1×Ar—$\underline{C}$ & 1×$\underline{C}$=$\underline{C}$H) 142.8, 142.9, 143.9, 148.6, 152.1 (5×Ar—$\underline{C}$), 166.7 ($\underline{C}$O$_2$CH$_3$), 205.5 ($\underline{C}$=O).

Synthesis of 3C12
Coupling Reaction

Silyl enol ether of 4-Methoxy-1-indanone

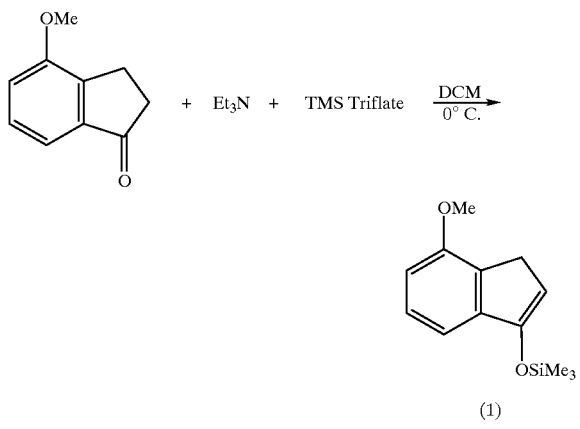

To a stirred solution of 4-Methoxy-1-indanone (200 mg, 1.24 mmol) and triethylamine (0.15 g, 0.21 ml, 1.48 mmol) in dichloromethane at 0° C. was added trimethylsilyl trifluoromethanesulfonate (0.27 g, 0.22 ml, 1.24 mmol). The solution was left stirring at 0° C. for 15 minutes and then the solution was rapidly passed through a plug of silica, eluting with petroleum ether (b.p. 40–60° C.):ethyl acetate 100:0.5. After evaporation of the eluent the silyl enol ether (1) was isolated as a clear colourless oil (260 mg, 91%).

Synthesis of 3C12

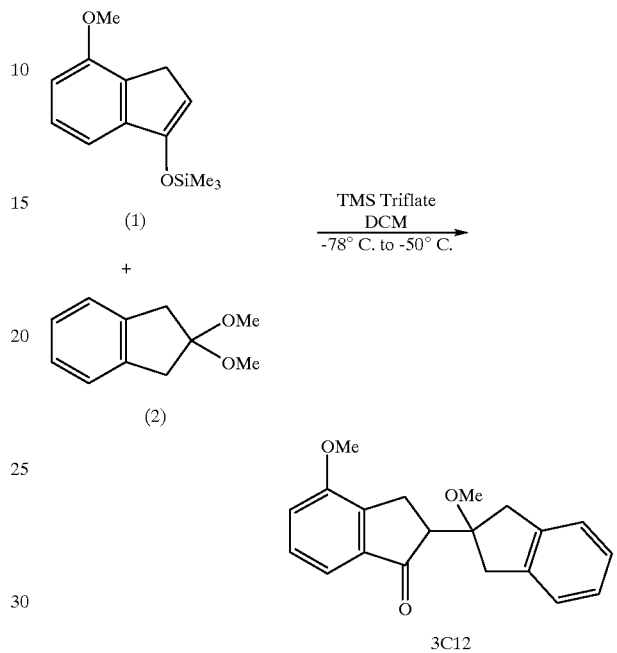

To a stirred solution of the silyl enol ether of 4-Methoxy-1-indanone (200 mg, 0.854 mmol) and the corresponding dimethyl acetal of indan-2-one (180 mg, 1.03 mmol) in dichloromethane at −78° C., was added a catalytic amount of TMS Triflate (45 µl). The solution was left stirring at −78° C. for 3 hours and then allowed to reach −50° C. for 1 hour. To this solution was then added solid sodium bicarbonate (approx 2.0 g). The organic layer was decanted and the residual solid was extracted with dichloromethane (2×20 ml). The combined organic layers were dried with sodium sulphate. After evaporation of the solvent, the crude product was passed through a plug of silica, eluting with petroleum ether 100% grading to petroleum ether:ethyl acetate, 100:4. After evaporation of the eluent 3C12 was isolated as a slightly coloured oil (0.16 g, 61%). On addition of ether to the oil 3C12 crystallised out as white crystals.

3C12

$^1$H NMR (CDCl$_3$, 300 MHz) $\delta_H$ 3.06 (3H, s, CH$_2$C—OC$\underline{H}_3$), 3.07 (2H, m, C$\underline{H}_2$), 3.25 (4H, m, 1×CH of C$\underline{H}_2$ & 1×C$\underline{H}$CH$_2$ & 1×C$\underline{H}_2$), 3.50 (1H, d, J=17.0 Hz, CH of C$\underline{H}_2$), 3.92 (3H, s, ArOC$\underline{H}_3$), 7.03 (1H, t, J=4 Hz, Ar—$\underline{H}$), 7.15 (4H, m, 4×Ar—$\underline{H}$), 7.38 (2H, d, J=5.0 Hz, 2×Ar—$\underline{H}$).

$^{13}$C NMR (CDCl$_3$, 75.47 MHz) $\delta$C 26.5, 40.5, 41.6 (3×$\underline{C}$H$_2$), 51.0, 53.4, 55.4 (2×O$\underline{C}$H$_3$ & 1×$\underline{C}$H), 87.4 (q$\underline{C}$), 114.6, 115.2, 115.3, 124.1, 124.2, 126.4, 128.7 (7×Ar—$\underline{C}$H), 139.1, 140.9, 141.5, 142.5, 156.8 (5×Ar—$\underline{C}$), 206.3 ($\underline{C}$=O).

Synthesis of 3C13

Alkylation of 3C12

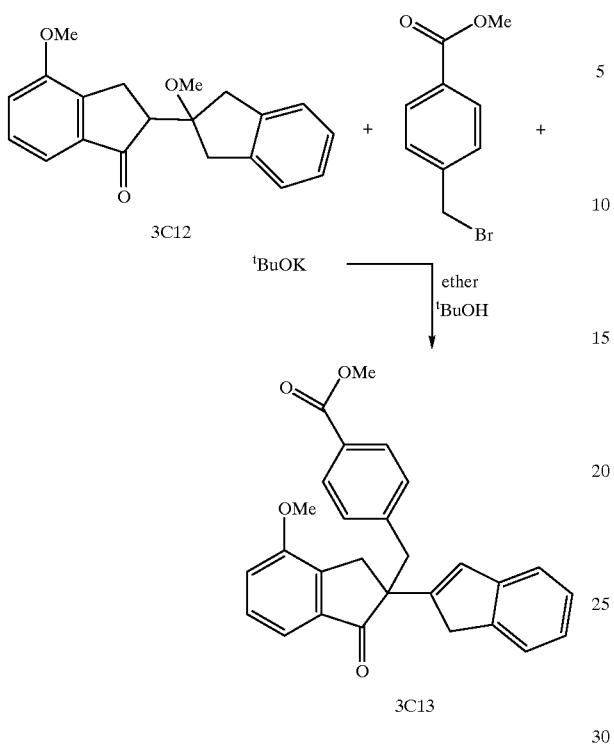

Usual procedure for alkylation of β-methoxy carbonyl compounds. 3C13 was isolated (160 mg, 80%).

$^1$H NMR (CDCl$_3$, 300 MHz) $\delta_H$ 3.26 (2H, ab q, J=17.8 Hz, C$\underline{H}_2$), 3.45 (4H, m, 2×C$\underline{H}_2$), 3.85, 3.86 (6H, 2×s, CO$_2$C$\underline{H}_3$ & Ar—OC$\underline{H}_3$), 6.73 (1H, br s, C=C$\underline{H}$), 6.98 (1H, m, Ar—$\underline{H}$), 7.21 (1H, dt, J=1.8 Hz & 6.7 Hz, Ar—$\underline{H}$), 7.23 (7H, br m, 7×Ar—$\underline{H}$), 7.83 (2H, br d, 2×Ar—$\underline{H}$).

$^{13}$C NMR (CDCl$_3$, 75.47 MHz) $\delta_C$ 34.2, 38.8, 42.2 (1× $\underline{C}$H$_2$), 51.9, 55.4 (1×O$\underline{C}$H$_3$ & CO$_2$$\underline{C}$H$_3$), 56.9 (q$\underline{C}$), 115.2, 116.1, 120.7, 123.5, 124.5, 126.3, 128.5, 129.2, 129.4, 129.4, 130.1, 130.1 (11×Ar—$\underline{C}$H & 1×$\underline{C}$H=C), 128.4, 136.6, 140.9, 142.9, 143.1, 144.1, 148.7, 156.5 (7×Ar—$\underline{C}$ & 1×$\underline{C}$=CH), 166.9 ($\underline{C}$O$_2$CH$_3$), 205.8 ($\underline{C}$=O).

Synthesis of 3C14
Coupling Reaction

Silyl enol ether of 5-Methoxy-1-indanone

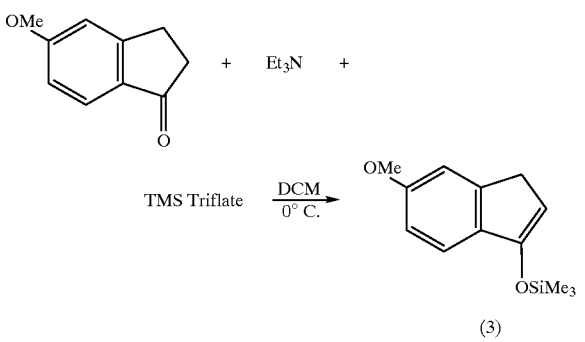

To a stirred solution of 5-Methoxy-1-indanone (200 mg, 1.24 mmol) and triethylamine (0.15 g, 0.21 ml, 1.48 mmol) in dichloromethane at 0° C. was added trimethylsilyl trifluoromethanesulfonate (0.27 g, 0.22 ml, 1.24 mmol). The solution was left stirring at 0° C. for 15 minutes and then the solution was rapidly passed through a plug of silica, eluting with petroleum ether (b.p. 40–60° C.):ethyl acetate 100:0.5. After evaporation of the eluent the silyl enol ether (3) was isolated as a clear colourless oil (240 mg, 85%).

Synthesis of 3C14

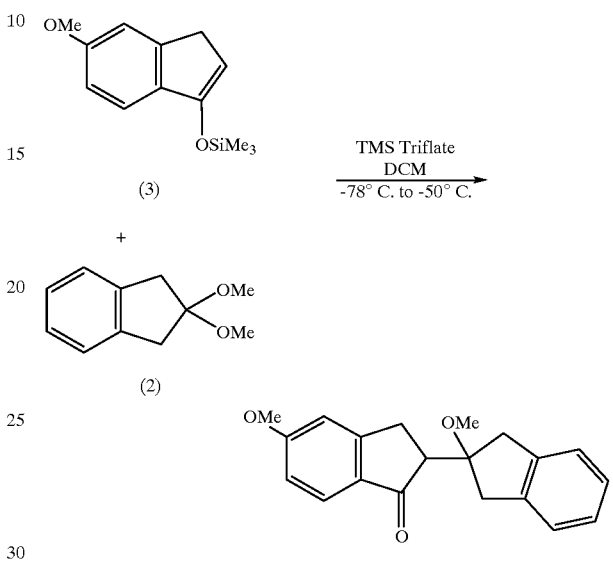

To a stirred solution of the silyl enol ether of 5-Methoxy-1-indanone (3) (200 mg, 0.854 mmol) and the corresponding dimethyl acetal of indan-2-one (180 mg, 1.025 mmol) in dichloromethane at −78° C., was added a catalytic amount of TMS Triflate (45 µl). The solution was left stirring at −78° C. for 3 hours and then allowed to reach −50° C. for 1 hour. To this solution was then added solid sodium bicarbonate (approx. 2 g). The organic layer was decanted and the residual solid extracted with dichloromethane (2×20 ml). The combined organic layers were dried with sodium sulphate. After evaporation of the solvent, the crude product was passed through a plug of silica, eluting with petroleum ether 100% grading to petroleum ether:ethyl acetate, 100:4. After evaporation of the eluent 3C14 was isolated as a slightly coloured oil (100 mg, 40.5%). On addition of ether to the oil 3C14 crystallised out as white crystals.

3C14

$^1$H NMR (CDCl$_3$, 300 MHz) $\delta_H$ 3.05 (3H, s, CH$_2$C—OC$\underline{H}_3$), 3.06 (1H, m, C$\underline{H}$), 3.25–3.47 (6H, br m, 3×CH$_2$), 3.89 (3H, s, Ar—OCH$_3$), 6.90 (2H, m, 2×Ar—H), 7.15 (4H, m, 4×Ar—H), 7.65 (1H, d, J=8.3 Hz, Ar—H).

$^{13}$C NMR (CDCl$_3$, 75.47 MHz) $\delta$C 29.4, 40.5, 41.6 (3× $\underline{C}$H$_2$), 51.1, 53.5, 55.6 (2×O$\underline{C}$H$_3$ & 1×$\underline{C}$H), 87.4 (q$\underline{C}$), 109.5, 115.3, 124.1, 124.3, 125.6, 126.5, 126.5 (7×Ar—$\underline{C}$H), 131.2, 141.0, 141.5, 156.6, 165.3 (5×Ar—$\underline{C}$), 204.3 ($\underline{C}$=O).

Synthesis of 3C15

Coupling Reaction

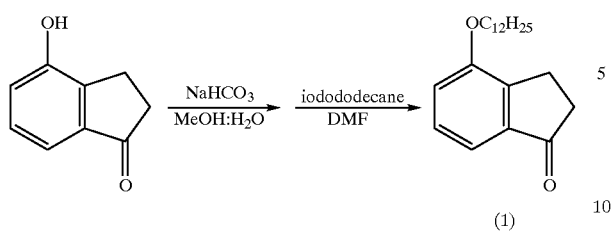

(1)

To a stirred solution of 4-hydroxy-1-indanone (0.5 g, 3.38 mmol) in methanol:water (10:1, 40 ml) was added sodium hydrogen carbonate (0.30 g, 3.57 mmol). The solvent was evporatored to dryness and to the salt which remained was added DMF (20 ml) and 1-iodododecane (2.0 g, 1.67 ml, 6.67 mmol). The solution was allowed to stir at reflux for 2 hours and then additional amount of 1-iodododecane (2.0 g) and sodium hydrogen carbonate (0.38 g) were added. The solution was allowed to stir at reflux for 1 hour. The reaction solution was allowed to cool and ether:water (1:1, 40 ml) was added. The organic phase was isolated and the aqueous layer was washed with ether. The combined organic layers were dried with $Na_2SO_4$ and the crude reaction mixture was purified by flash column chromatography to yield dodecylether (1) (660 mg, 62%).

Synthesis of the silyl enol ether

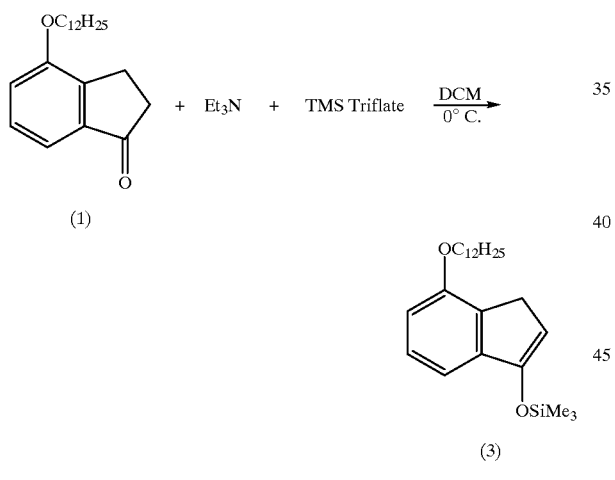

Usual procedure for silyl enol ether synthesis.

Yield (200 mg, 92%).

Synthesis of 3C15

Coupling Reaction

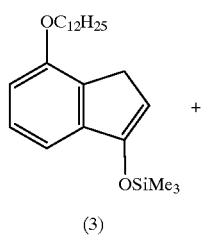

-continued

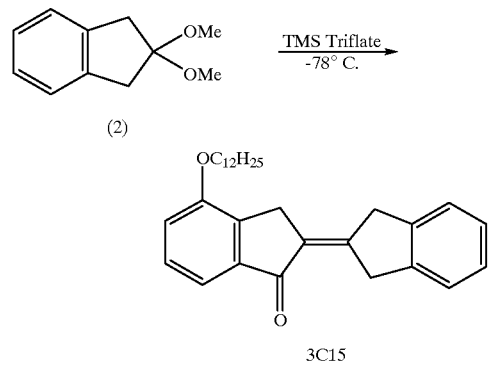

Usual procedure for coupling synthesis.

Yield (90 mg, 41%).

$^1$H NMR (CDCl$_3$, 300 MHz) $\delta_H$ 0.91 (3H, m, (CH$_2$)$_{10}$CH$_2$CH$_3$), 1.28 (18H, m, OCH$_2$CH$_2$(CH$_2$)$_9$CH$_3$), 1.86 (2H, m, OCH$_2$CH$_2$(CH$_2$)$_9$CH$_3$), 3.52, 3.91, 4.37 (6H, 3×br s, 3×CH$_2$), 4.05 (2H, t, J=13.0 Hz, OCH$_2$CH$_2$(CH$_2$)$_9$CH$_3$), 6.98 (1H, d, J=7.3 Hz, Ar—H), 7.35 (6H, br m, 6×Ar—H).

$^{13}$C NMR (CDCl$_3$, 75.47 MHz) $\delta$C 14.1 (CH$_3$), 22.7, 25.9, 26.1, 28.9, 29.2, 29.3, 29.4, 29.6, 29.7, 31.9, 39.2, 40.3 68.3, 65.9 (14×CH$_2$), 115.3, 115.4, 124.4, 124.9, 126.6, 126.9, 128.7 (7×Ar—CH), 129.2, 137.4, 139.3, 141.2, 142.3, 154.7, 156.2 (5×Ar—C & 2×C=C), 209.1 (C=O).

Synthesis of 3C16

Alkylation of 3C15

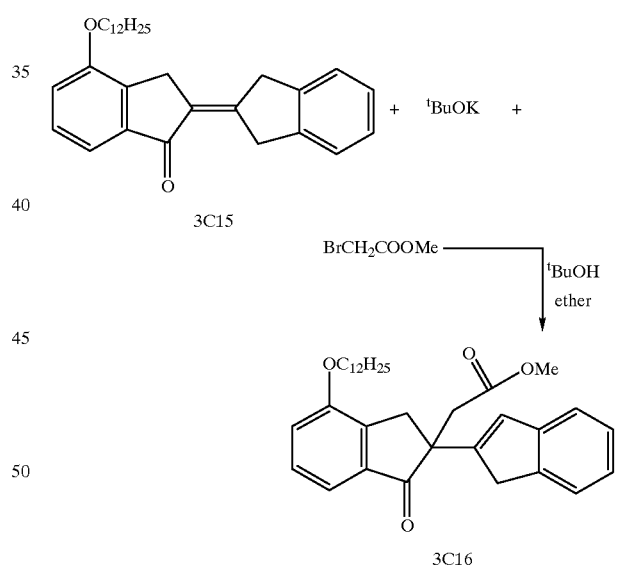

Usual potassium tert-butoxide method.

Yield (120 mg, 51%).

Synthesis of 3C17

Synthesis of the silyl enol ether of Bromo-indanone

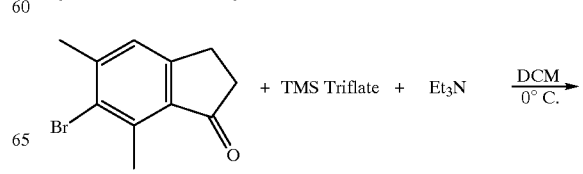

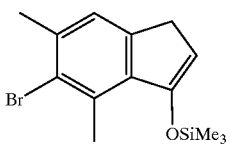

To a stirred solution of 6-Bromo-5,7-dimethyl-1-indanone (0.5 g, 2.11 mmol) in DCM (3 ml) at 0° C. was added triethylamine (0.21 g, 0.29 ml, 2.08 mmol) and TMS triflate (0.466 g, 0.38 ml, 2.09 mmol). The solution was left stirring at 0° C. for 10 min and then the solution was passed through a plug of silica eluting with petroleum ether to give the silyl enol ether of 6-Bromo-5,7-dimethyl-1-indanone as a mobile oil (0.62 g, 95%).

Synthesis of Bromo-methoxy dimer

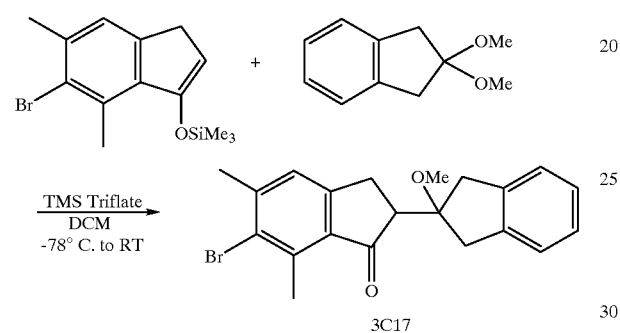

To a solution of the dimethyl acetal of 2-indanone (0.50 g, 2.81 mmol) and the silyl enol ether of 6-Bromo-5,7-dimethyl-1-indanone (0.50 g, 1.76 mmol) in DCM at −78° C. was added a catalytic amount of TMS triflate (40 μl). The reaction was then allowed to slowly warm to room temperature and then left stirring at room temperature for 4 hours. To this solution at room temperature was added solid sodium bicarbonate (1.0 g) and the heterogenous mixture left stirring for 15 minutes. The mixture was then passed through a plug of silica and the Bromo-methoxy dimer 3C17 was isolated as a yellowish solid, which rapidly crystallised from diethyl ether to give white crystals of the titled compound (0.3 g, 49.2%).

$^1$H NMR (CDCl$_3$, 300 MHz) δ$_H$ 2.50 (3H, s, Ar—C$\underline{H}_3$), 2.80 (3H, s, Ar—C$\underline{H}_3$), 2.95 (3H, s, OC$\underline{H}_3$), 3.18 (1H, br m, COC$\underline{H}$CH$_2$), 3.16 (2H, br m, C$\underline{H}_2$), 3.28 (2H, br m, C$\underline{H}_2$), 3.30 (2H, ab q, J=12.6 Hz, CC$\underline{H}_2$), 7.15 (4H, m, 4×Ar—$\underline{H}$), 7.24 (1H, br s, Ar—$\underline{H}$).

$^{13}$C NMR (CDCl$_3$, 75.47 MHz) δC 17.5, 25.1 (2×$\underline{C}$H$_3$), 29.6, 40.6, 41.6 (3×$\underline{C}$H$_2$), 51.1, 54.2 (1×$\underline{C}$H & 1×O$\underline{C}$H$_3$), 87.4 (q$\underline{C}$), 124.1, 124.3, 125.7, 126.5, 128.1, 134.1, 139.0, 140.9, 141.5, 141.8, 144.8, 153.1 (5×Ar—$\underline{C}$H, 4×Ar—$\underline{C}$ & 2×Ar$\underline{C}$—CH$_3$, 1×Ar$\underline{C}$Br), 205.7 ($\underline{C}$=O).

Synthesis of 3C18

Alkylation of 3C17

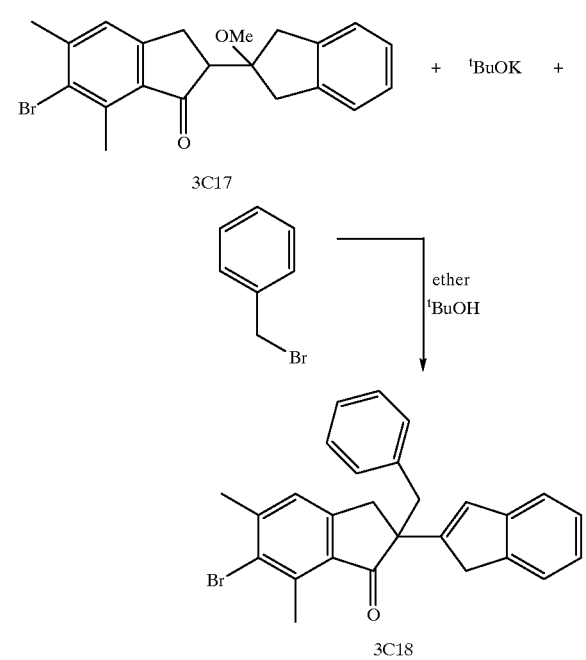

To a solution of Bromo-methoxy 3C17 (200 mg, 0.519 mmol) in ether (6 ml) was added benzyl bromide (0.30 g, 0.20 ml, 1.75 mmol). To this solution at room temperature was added dropwise a solution of potassium tert-butoxide (0.05 g, 0.439 mmol) in $^t$BuOH (6 ml). Analysis of this solution indicated that all of the bromo-methoxy 3C17 was converted to the bromobenzyl 3C18 with a second product having a slightly lower R$_f$ than the starting bromo-methoxy 3C18. The crude reaction mixture was purified by flash column chromatography to yield 3C18 (0.12 g, 52%).

Synthesis of 3C19 & 3C20 by reduction with Lithium tri-tert-butoxyaluminohydride

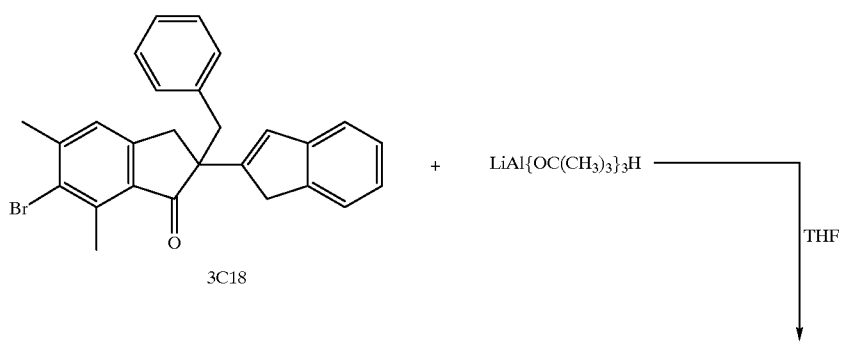

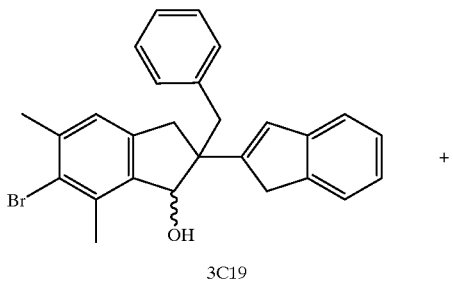

3C19

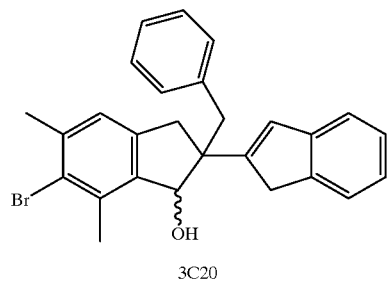

3C20

3C18 (200 mg, 0.451 mmol) was dissolved in dry THF (5 ml) and to this was added lithium tri-tert-butoxyaluminohydride (0.50 g, 1.97 mmol). The solution was allowed to stir for 3 hours. The solvent was removed and the crude reaction mixture was purified by flash column chromatography to yield the two diasteriomers 3C19 (90 mg, 96%) and 3C20 (90 mg, 96%).

3C20

$^1$H NMR (CDC13, 300 MHz) dH 2.40 (3H, s, C$\underline{H}_3$), 2.48 (3H, s, C$\underline{H}_3$), 2.80 (1H, d, J=13.6 Hz, CH of CH$_2$), 3.00 (2H, ab q, J=15.6 Hz, CH of CH$_2$), 3.23 (1H, d, J=13.6 Hz, CH of CH$_2$), 3.54 (2H, ab q, J=22.6 Hz, CH$_2$), 5.18 ( 1H, br m, C$\underline{H}$OH), 6.52 (1H, br s, C=CH), 6.89 (2H, m, 2×Ar—H), 7.20 (5H, m, 5×Ar—H), 7.30 (3H, 2×Ar—H), 7.45 (1H, d, J=6.0 Hz, 1×Ar—H).

Synthesis of 3C21

Coupling Reaction

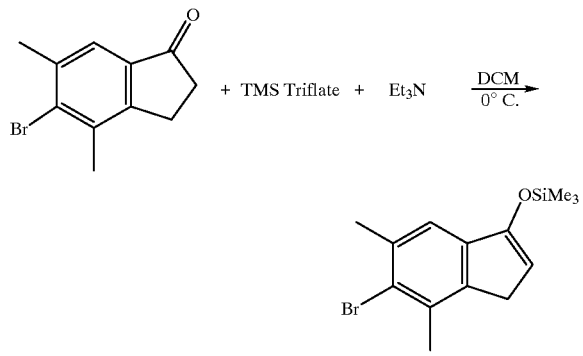

To a stirred solution of 5-Bromo-4,6-dimethyl-1-indanone (0.5 g, 2.11 mmol) in DCM (3 ml) at 0° C. was added triethylamine (0.21 g, 0.29 ml, 2.08 mmol) and TMS triflate (0.466 g, 0.38 ml, 2.09 mmol). The solution was left stirring at 0° C. for 10 min and then the solution was passed through a plug of silica eluting with petroleum ether to give the silyl enol ether of 5-Bromo-4,6-dimethyl-1-indanone as a white crystalline solid (0.60 g, 94%).

Synthesis of Bromo-methoxy Dimer 3C21

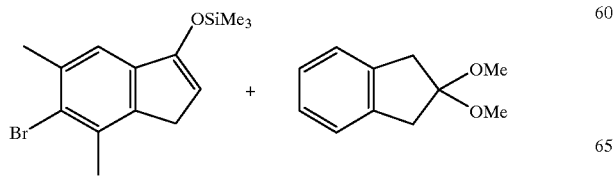

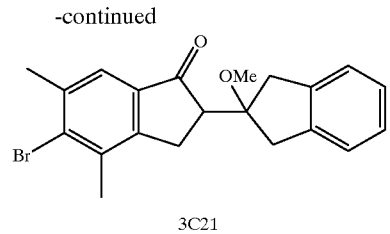

3C21

To a solution of the dimethyl acetal of 2-indanone (0.50 g, 2.81 mmol) and the silyl enol ether of 5-Bromo-4,6-dimethyl-1-indanone (0.50 g, 1.76 mmol) in DCM at −78° C. was added a catalytic amount of TMS triflate (40 μl). The reaction was then allowed to slowly warm to room temperature and then left stirring at room temperature for 4 hours. To this solution at room temperature was added solid sodium bicarbonate (1.0 g) and the heterogenous mixture left stirring for 15 minutes. The mixture was then passed through a plug of silica and the Bromo-methoxy 3C21 was isolated as a yellowish solid, which rapidly crystallised from diethyl ether to give fine white crystals (271 mg, 40%).

$^1$H NMR (CDCl$_3$, 300 MHz) δ$_H$ 2.54 (6H, br s, 3×overlapping C$\underline{H}_3$), 3.10 (3H, s, OC$\underline{H}_3$), 3.12 (1H, m, C$\underline{H}$CH$_2$), 3.21–3.38 (5H, m, 2×C$\underline{H}$2 & 1×CH of CH$_2$), 3.73 (1H, d, CH of CH$_2$), 7.16 (4H, m, 4×Ar—$\underline{H}$), 7.44 (1H, s, Ar—$\underline{H}$).

Synthesis of 3C22

Alkylation of 3C21

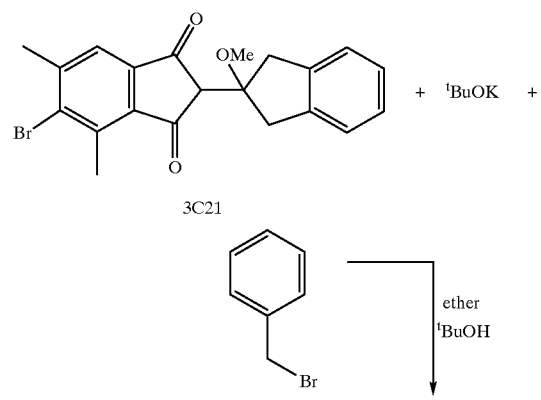

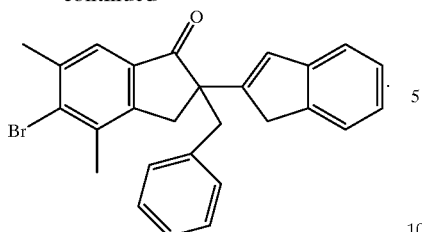

3C22

To a solution of Bromo-methoxy dimer 3C21 (200 mg, 0.519 mmol) in ether (6 ml) was added benzyl bromide (0.30 g, 0.20 ml, 1.75 mmol). To this solution at room temperature was added dropwise a solution of potassium tert-butoxide (0.05 g, 0.439 mmol) in $^t$BuOH (6 ml). Analysis of this solution indicated that all of the bromo-methoxy dimer was converted to the bromobenzyl dimer 3C22 and a product having a slightly lower $R_f$ than the staring bromo-methoxy dimer. The crude reaction mixture was purified by flash column chromatography to yield 3C22 (0.14 g, 61%).

Synthesis of 3C23 & 3C24 by Reduction with Lithium Tri-tert-butoxyaluminohydride

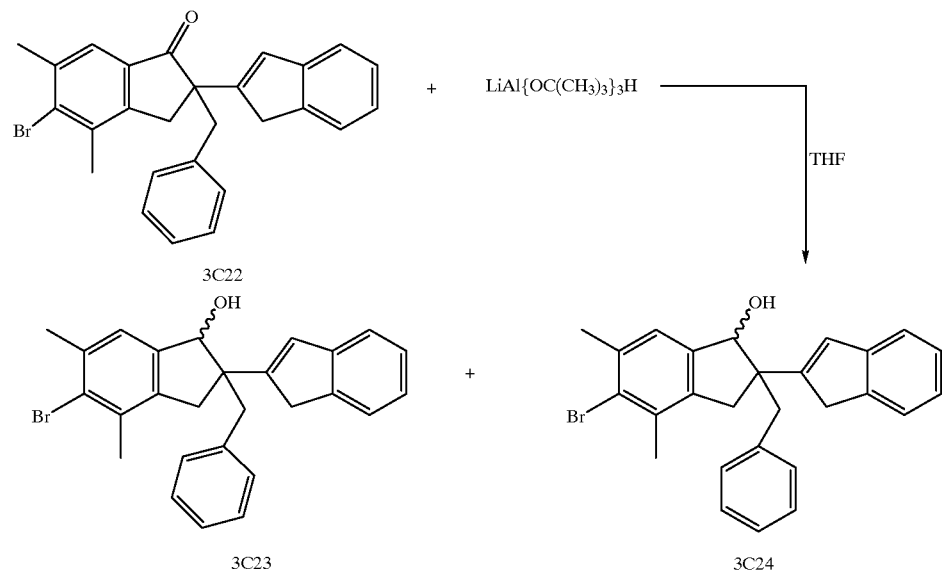

3C22 (200 mg, 0.451 mmol) was dissolved in dry THF (5 ml) and to this was added lithium tri-tert-butoxyaluminohydride (0.50 g, 1.97 mmol). The solution was allowed to stir for 3 hours. The solvent was removed and the crude reaction mixture was purified by flash column chromatography to yield 3C23 (90 mg, 96%) and 3C24 (90 mg, 96,).

Synthesis of 3C25 was allowed to stir at room temperature for 1 hour. The solvent was removed and the product was purified by flash column chromatography to yield compound (1).

Aluminium chloride (15.55 g, 0.116 mol) was suspended in $CS_2$ (30 ml) and to this β-chloropropionylchloride (6.36 g, 0.05 mol) was added dropwise over 20 mins. The suspension was cooled to 0° C. and compound (1) (6.8 g, 0.042 mol) in $CS_2$ (6ml) was added dropwise over 20 min. The

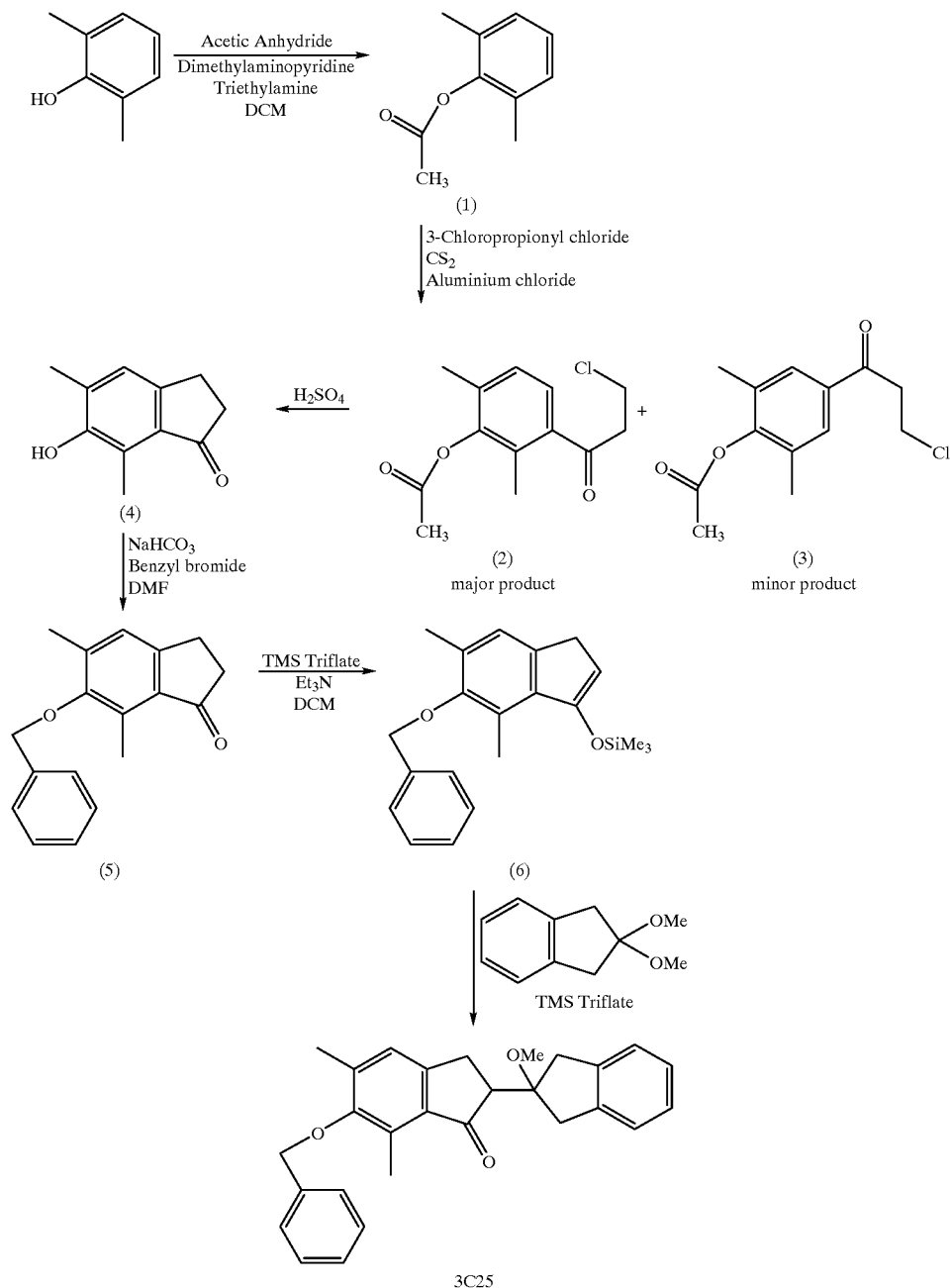

Synthesis of 3C25

2,6-dimethylphenol (5.0 g, 0.041 mol) was dissolved in DCM (20 ml) and to this was added triethylamine (8.29 g, 11.41 ml, 0.082 mol) and acetic anhydride (6.28 g, 5.80 ml, 0.0615 mol). To this stirring solution was added dimethylaminopyridine (500 mg, 0.0041 mol). The reaction mixture reaction was allowed to stir at room temperature for 3 hrs. The reaction was quenched with iced water and the organic phase was extracted with ethyl acetate. The organic layers were combined and dried over $Na_2SO_4$. The solution was filtered and the excess solvent was removed by distillation.

The crude product was purified by flash column chromatography to yield compound (2).

Compound (2) was placed in a round bottomed flask and to it was added conc. $H_2SO_4$ on addition of the acid the solution turned red. The solution was allowed to stir at room temperature for 3 hrs. The reaction mixture was then poured onto iced water and the organic phase was extracted with ethyl acetate and washed with water (2×20 ml). The excess solvent was removed and the crude reaction mixture was purified by flash column chromatography. Compound (4) was isolated as a yellow powder.

To a stirred solution of 5,7-dimethyl-6-hydroxy-indan-1-one; compound 4 (1.0 g, 5.68 mmol) in DMF (15 ml) was added sodium bicarbonate (2.0 g, 23.5 mmol) and benzyl bromide (2.0 g, 11.6 mmol). The mixture was left stirring at reflux for 3.5 hours. At this point benzyl bromide (1.0 g, 5.8 mmol) and solid sodium bicarbonate (1.0 g, 11.7 mmol) were added gradually to the refluxing mixture. The reaction was then left refluxing for 1 hour. After cooling the reaction mixture to room temperature, Ether (50 ml) and water (50 ml) were added. The organic layer was extracted and the aqueous phase re-extracted with 2×25 ml of ether. The combined organic layers were dried with sodium sulphate. Filtration followed by evaporation left a mobile oil which was passed through a plug of silica eluting with petroleum ether grading to petroleum ether:ethyl acetate 98:2. Evaporation of the eluent left the benzyl ether as a mobile oil compound (5) (1.20 g, 8%).

To a stirring solution of compound (5) (200 mg, 0.75 mmol) in dry DCM (10 ml), to this was added triethylamine (84 mg, 0.115 ml, 0.83 mmol) and TMS triflate (0.158 g, 0.136 ml, 0.76 mmol). The solution was allowed to stir at 0° C. for 15 mins and was then passed through a plug of silica, eluting with petroleum ether. Evaporation of the solvent afforded compound (6) as a mobile oil (0.19 g, 81%).

To a stirring solution of compound (6) and dimethyl acetal of indan-2-one in DCM (10 ml) at −78° C. was added TMS triflate (45 μl). The mixture was allowed to stir at room temperature for 2 hours. The crude reaction mixture was then passed through a plug of silica, eluting with petroleum ether:ethyl acetate 98:2. This then afforded 3C25.

$^1$H NMR (CDCl$_3$, 300 MHz) $\delta_H$ 2.37 (3H, s, Ar—CH$_3$), 2.62 (3H, s, Ar—CH$_3$), 3.08 (3H, s, OMe), 3.09–3.52 (7H, m, 3-CH$_2$ & 1×CH), 4.79 (2H, s, PhCH$_2$O—), 7.16–7.43 (10H, 2×br m, Ar—H).

$^{13}$C NMR (CDCl$_3$, 75.47 MHz) $\delta_C$ 11.2, 17.5 (2×Ar—CH$_3$), 28.6, 40.6, 41.5 (3×CH$_2$), 51.1, 54.2 (CH & OCH$_3$), 74.4 (PhCH$_2$), 87.4 (C—OMe), 124.2, 124.5, 125.9, 126.2, 126.2, 127.8, 127.8, 128.2, 128.8, 128.8 (10×Ar—CH), 131.2, 134.5, 137.1, 138.9, 141.1, 141.6, 150.1, 155.0 (8×Ar—C).

Synthesis of 3C26

Alkylation of 3C25

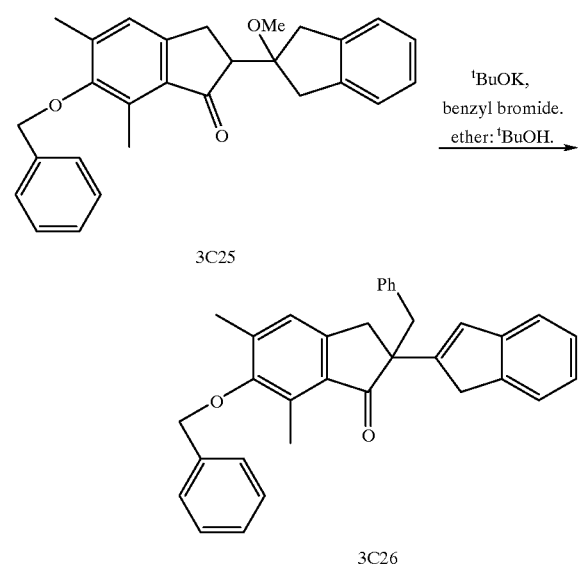

To a stirring solution of 3C25 (50 mg, 0.12 mmol) in ether/$^t$butanol 6:1 (7 ml) at room temperature was added potassium-tert-butoxide (13.8 mg, 0.12 mmol) dropwise over 2 hours. To this solution was then added a saturated aqueous, solution of ammonium chloride (20 ml) and ether (25 ml). The organic layer was isolated and the aqueous layer extracted with ether (2×20 ml). The combined organic layers were dried with sodium sulphate and filtered. Evaporation of the solvent left an oil, which passed through a plug of silica, eluting with petroleum ether:ethyl acetate 98:2. Evaporation of the solvent left the product 3C26 as an oil (40 mg).

$^1$H NMR (CDCl$_3$, 300 MHz) $\delta_H$ 2.31 (3H, s, ArCH$_3$), 2.61 (3H, s, ArCH$_3$), 3.13–3.56 (6H, m, 3×CH$_2$), 4.74 (2H, s, PhCH$_2$O), 6.71 (1H, br s, CH=CCH$_2$), 7.12 (15H, br m, 15 Ar—H).

$^{13}$C NMR (CDCl$_3$, 75.47 MHz) $\delta_C$ 11.4, 17.5 (2×CH$_3$), 36.6, 38.9, 42.4, 57.9 (4×CH$_2$), 74.4 (CH), 120.6, 123.5, 124.3, 125.4, 125.9, 126.3, 126.4, 127.8, 128.1, 28.1, 128.6, 129.9, 131.9, 137.1, 137.8 (15×Ar—CH) 139.2, 143.3, 144.4, 148.9, 149.8, 155.2 (6×Ar—C), 206.3 (C=O).

Synthesis of 3C27 and 3C28

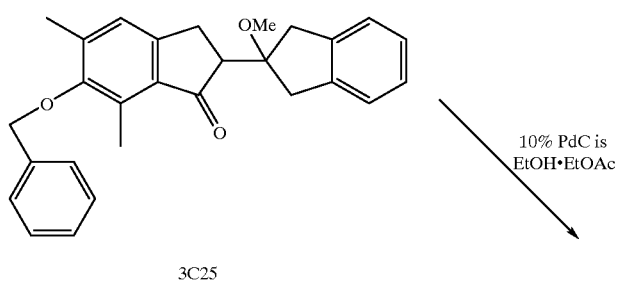

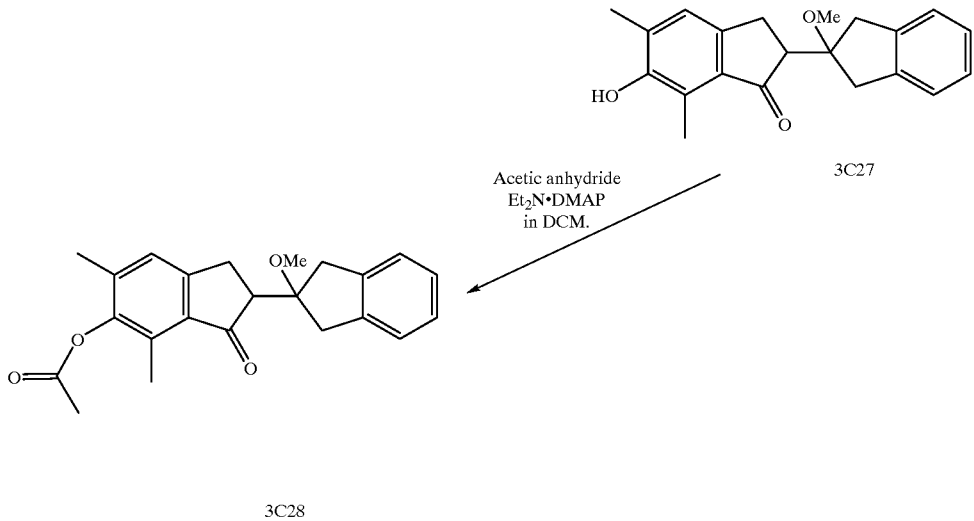

To a stirring solution of 3C25 (0.20 g, 0.49 mmol) in EtOH:EtOAc 1:1 (10 ml) was added 10% palladium on carbon (0.20 g). Hydrogenolysis of the benzyl ether of 3C25 was carried out under an atmosphere of hydrogen at room temperature and 1 atm pressure. After stirring the mixture for 24 hr, the solvent was evaporated off, and to the residue was added ether (20 ml). The mixture was then filtered and evaporation of the solvent left the phenol 3C27 as a mobile oil (0.12 g, 76%). To a solution of the phenol 3C27 (0.10 g, 0.31 mmol) in dry DCM (3 ml) was added triethylamine (63 mg, 2 eq.) acetic anhydride (63 mg, 2 eq) and a catalytic amount of DMAP (10 mol %). The solution was left stirring at room temperature for 3 hr. The solution was then passed through a plug of silica eluting with petroleum ether:ethyl acetate 98:2. After evaporation of the solvent 3C28 was isolated as a mobile oil.

$^1$H NMR (CDCl$_3$, 300 MHz) $\delta_H$ 2.22 (3H, S, OC=OC$\underline{H}_3$), 2.35 (3H, s, ArC$\underline{H}_3$), 2.45 (3H, s, ArC$\underline{H}_3$), 3.05 (3H, s, OC$\underline{H}_3$), 3.08–3.50 (7H, br m, 3×C$\underline{H}_2$ & 1×C$\underline{H}$), 7.15 (5H, br m, 5×Ar$\underline{H}$).

Synthesis of Chloroketone

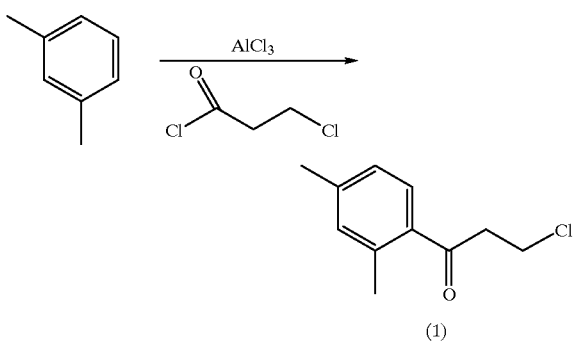

To a solution of aluminium chloride (6.28 g, 47.2 mmol) in carbon disulfide (30 ml) was added 3-chloropropionyl chloride (6.0 g, 47.2 mmol). The mixture was left stirring at 0° C. for 1 hour and then to the mixture was added m-xylene (5.0 g, 47.2 mmol). The mixture was left stirring for a further half hour. At this point a TLC indicated that all of the starting material was consumed. The mixture was then added to approx. 200 g of crushed ice and the resulting mixture partitioned using ether. The organic layer was obtained and the aqueous layer extracted with ether (2×100 ml). The combined organic layers were dried and concentrated in vacuo to leave a mobile oil, which was passed through a plug of silica, eluting with petroleum spirits (40–60° C.): ethyl acetate 9:1, to yield chloroketone (1) after evaporation of the eluent as the major product (5.50 g, 59.4%).

Synthesis of 5,7-dimethyl-1-indanone

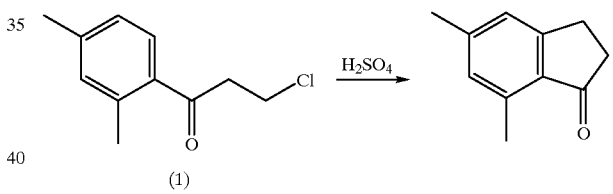

A solution of the chloroketone (1) (5.0 g, 25.5 mmol) in concentrated sulphuric acid (100 ml) was heated to 95° C. and left stirring for 1 hour. The solution was cooled and then it was added slowly to 700 g of crushed ice. The crude product was then extracted with ethyl acetate (3×200 ml). The combined organic layers were washed with water and the resulting organic solvent was dried with sodium sulphate. The solvent was filtered and evaporation of the solvent left a mobile oil, which was passed through a plug of silica yielding the 5,7-dimethyl-1-indanone (3.80 g, 93%) as the major product.

$^1$H NMR (CDCl$_3$, 300 MHz) $\delta_H$ 2.34, 2.56 (6H, 2×s, 2×C$\underline{H}_3$), 2.59, 2.98 (4H, 2×br m, 2×C$\underline{H}_2$), 6.86, 7.03 (2H, 2×s, 2×Ar—$\underline{H}$).

$_{13}$C NMR (CDCl$_3$, 75.47 MHz) $\delta_C$ 18.1, 21.7 (2×$\underline{C}$H$_3$), 25.0, 36.8 (2×$\underline{C}$H$_2$), 124.3, 130.1 (2×Ar—$\underline{C}$H), 132.1, 138.3, 144.8, 156.4 (4×Ar—$\underline{C}$), 207.3 ($\underline{C}$=O).

Synthesis of the Silyl Enol Ether of 5,7-dimethyl-1-indanone

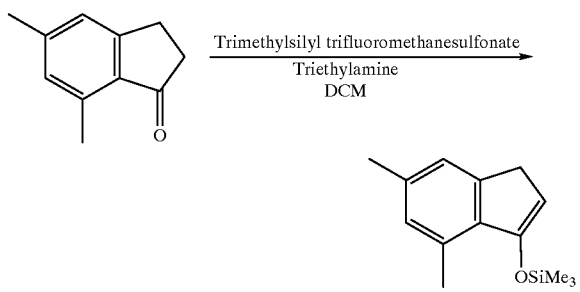

To a stirring solution of 5,7-dimethyl-1-indanone (0.50 g, 3.12 mmol) in DCM (5 ml) at 0° C. was added triethylamine (0.374 g, 0.525 ml, 3.77 mmol) and a 25% solution of trimethyl silyl trifluoromethanesulfonate in DCM (0.55 ml, 3.70 mmol) was added dropwise. The solution was left stirring at 0° C. for 10 min and analysis by TLC indicated that the formation of the silyl enol ether was approx 75% complete as judged by TLC with only starting material present. The solution was then rapidly passed through a plug of silica. Evaporation of the eluent left the silyl enol ether of 5,7-dimethyl-1-indanone as a mobile oil (0.51 g, 70.4%).
Coupling of the Corresponding Silyl Enol Ether of 5,7-dimethyl-1-indanone to the Dimethylacetal of 2-indanone

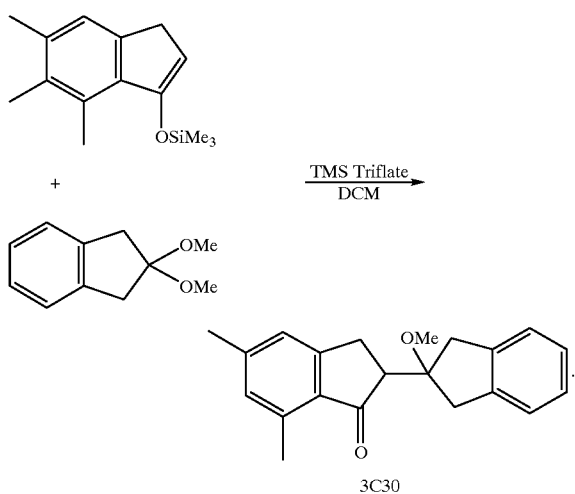

To a stirred solution of the silyl enol ether of 5,7 dimethyl-1-indanone (0.50 g, 2.16 mmol) and the corresponding dimethyl acetal of indan-2-one (0.50 g, 2.81 mmol) in DCM (5 ml) at −78° C. was added a dilute solution of TMS Triflate (25 ml in 1 ml DCM). The solution was left stirring at −78° C. for half an hour and then the temperature was allowed to reach room temperature and the reaction was allowed to stir at this temperature for 18 hours. To this solution was then added solid sodium bicarbonate approx 0.5 g and the mixture was stirred rapidly for 10 mins. The mixture was filtered and purified by flash column chromatography. After evaporation of the eluent the expected dimer 3C30 was isolated as a mobile oil, (0.15 g, 22.6%).

$^1$H NMR (CDCl$_3$, 300 MHz) δ$_H$ 2.41, 2.58 (6H, 2×s, 2×C$\underline{H}_3$), 3.06 (1H, m, COC$\underline{H}$), 3.07 (3H, s, OC$\underline{H}_3$), 3.20 (5H, br m, 1×C$\underline{H}_2$ & 3×CH of C$\underline{H}_2$), 3.50 (1H, d, J=15 Hz, CH of C$\underline{H}_2$), 6.91 (1H, s, 1×Ar—$\underline{H}$), 7.10–7.20 (4H, br m, 4×Ar—$\underline{H}$).

Synthesis of 3C31

Same procedure as for the synthesis of 3C5.

Synthesis of 3C32 & 3C33

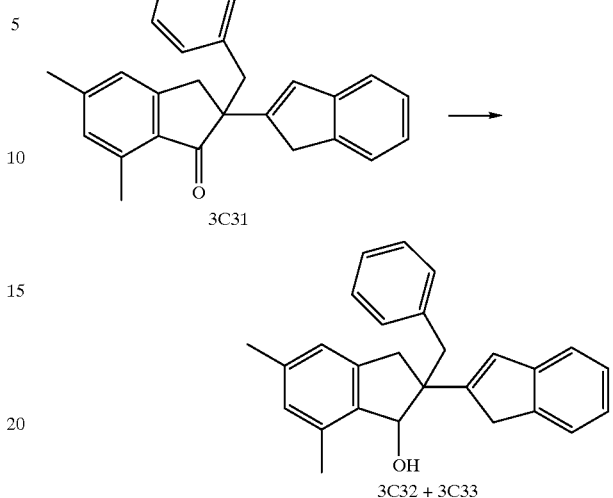

To a stirring solution of the benzyl dimer 3C31 (0.10 g, 0.27 mmol) in the THF (4 ml) at 0° C. was added lithium tri-tert-butoxyaluminohydride (0.20 g, 0.79 mmol). The mixture was left stirring at 0° C. for 1 hour and then at room temperature for 2 hours. To this solution was then added (80 mg, 0.31 mmol) of lithium tri-tert-butoxyaluminohydride and the mixture left stirring at room temperature for 3 days. The solvent was then evaporated off and the residue was taken up in DCM (2 ml). The cloudy mixture was then passed through a plug of silica to remove the lithium tri-tert-butoxyaluminohydride. The eluent containing the mixture of alcohols was evaporated off to dryness to leave an oil which was then taken up in the minimum amount of DCM. The two pairs of diasteriomeric alcohols were separated from each other by flash column chromatography to leave both pairs of alcohols as mobile oils 3C32 & 3C33, total combined yield (95 mg, 95%).

Top Spot $^1$H NMR (CDCl$_3$, 300 MHz) δ$_H$ 2.38, 2.45 (6H, 2×s, 2×C$\underline{H}_3$), 2.80 (2H, ab q, J=13.4 Hz, C$\underline{H}_2$), 3.00 (2H, ab q, J=15.9 Hz, C$\underline{H}_2$), 3.65 (2H, ab q, C$\underline{H}_2$), 5.03 (1H, s, C$\underline{H}$OH), 6.58 (1H, s, C=C$\underline{H}$), 6.80 (2H, br m, 2×Ar—H), 6.93 (1H, s, 1×Ar—H), 7.15–7.23 (6H, br m, 6×Ar—H), 7.47 (1H, d J=3.0 Hz, 1×Ar—H).

Synthesis of 3C36/3C37

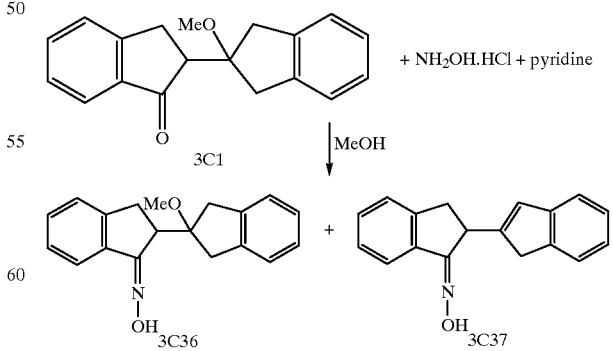

Dimer 3C1 (100 mg, 0.359 mmol) was dissolved in pyridine (0.5 ml) and to this hydroxylamine hydrochloride (300 mg, 4.34 mmol) and methanol (2 ml) were added. The reaction solution was then allowed to reflux for 3 hrs. The reaction was quenched with 2M aqueous HCl (10 ml) and the organic phase was extracted into ether. The organic layers were combined and dried over $Na_2SO_4$. The crude reaction mixture was passed through a flash silica column, eluting with petroleum ether:ethyl acetate, 9:1. The product was isolated as an oxime mixture of 3C36 and 3C37.

$^1$H NMR (CDCl$_3$, 300 MHz) $\delta_H$ 3C37 3.02 (1H, dd, J=2.6, 16.9 Hz, CH of CH$_2$), 3.23 (2H, q, J=16.0 and 7.3 Hz, CH$_2$), 3.52 (1H, dd, J=8.6 and 8.6 Hz, CH of CH$_2$), 4.59 (1H, dd, J=8.6 and 1.4 Hz, CHCH$_2$), 6.08 (1H, s, C=CHCH$_2$), 7.16–7.40 (8H, br m, 8×Ar—H), 7.94 (1H, d, J=7.8 Hz, 1×Ar—H).

$^{13}$C NMR (CDCl$_3$, 75.47 MHz) $\sigma_C$ 37.2, 37.6 (2×CH$_2$), 39.8 (1×CH), 118.9, 123.4, 123.9, 124.9, 125.6, 126.0, 127.4, 128.0, 132.3 (9×Ar—CH and 1×C=CH).

Synthesis of 3C38 and 3C39

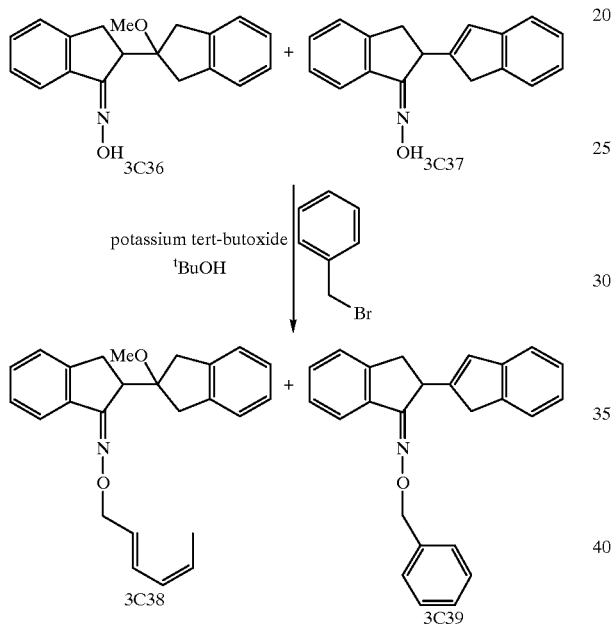

Oxime mixture 3C36 and 3C37 (200 mg) was dissolved in $^t$BuOH (10 ml) and to this was added bromide (1.6 g, 0.82 ml). To this stirring solution potassium tert-butoxide (0.76 g) in $^t$BuOH (10 ml) and ether (2 ml) was added dropwise over a period of 2 hrs. The reaction was then quenched with aqueous ammonium chloride solution and the organic phase was extracted into ether. The organic phases were combined and dried over Na$_2$SO$_4$. The crude reaction mixture was passed through a flash silica column, eluting with petroleum ether:ethyl acetate, 7:3. This afforded 3C38 and 3C39. 3C39

$^1$H NMR (CDCl$_3$, 300 MHz) $\delta_H$ 3.00 (1H, d, J=2.2, 14.9 Hz, CH of CH$_2$), 3.22 (2H, br d, J=6.6 Hz, CH$_2$), 3.55 (2H, dd, J=16.8, 8.8 Hz, CH of CH$_2$), 4.62 (1H, br d, J=7.0 Hz, CH), 5.12 (2H, s, PhCH$_2$O), 606 (1H, d, J=1.32 Hz, C=CHCH$_2$), 7.25 (12H, br m, 12×Ar—H), 7.81 (1H, br d, J=6.0 Hz, 1×Ar—H).

$^{13}$C NMR (CDCl$_3$, 75.47 MHz) $\delta_C$ 37.0, 37.5 (CH$_2$), 39.0 (CH), 76.11(PhCH$_2$O), 119.3, 121.8, 123.8, 124.5, 125.5, 126.0, 127.1, 127.4, 1:27.8, 127.8, 128.0, 128.0, 128.0, 130.4, 136.2, 138.1, 143.3, 144.1, 144.6, 146.6, (5×Ar—C and C=CH), 162.7 (PhCH$_2$ON=C).

Synthesis of 3C40

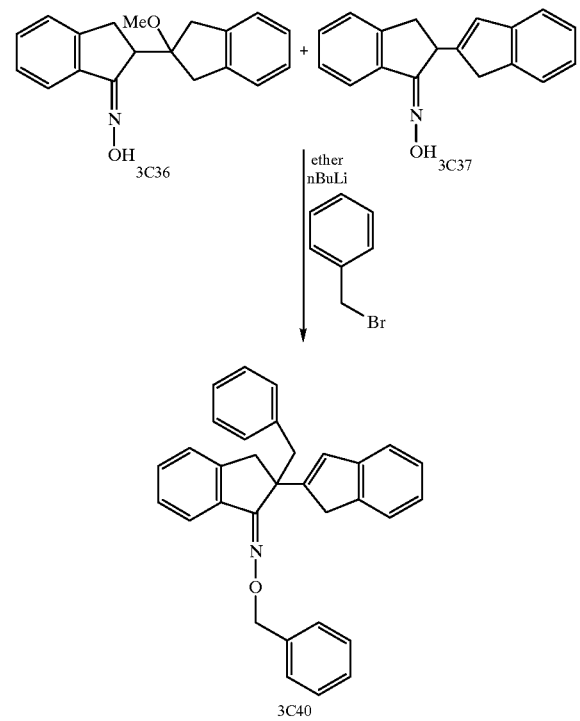

Oxime mixture 3C36 and 3C37 (200 mg) was dissolved in dry ether (10 ml). The reaction flask was then cooled to −78° C. and N-butyl lithium (1 ml, 2.5 M) was added. After 5 mins benzyl bromide (1 ml) was added. The reaction was allowed to stir at −78° C. for 2 hrs. The reaction was allowed to stir at room temperature for 3 hrs. Aqueous HCl and ether were added to the reaction flask. The organic layer was isolated and dried over Na$_2$SO$_4$. The crude reaction mixture was passed through a flash silica column eluting with petroleum ether:ethyl acetate 8:2 to afford 3C40.

$^1$NMR (CDCl$_3$, 300 MHz) $\delta_H$ 3.65, 3.81 and 4.0 (6H, s, CH$_2$), 5.40 (2H, s, PhCH$_2$O), 7.21–7.40 (16H, br m, 15×Ar—H and 1×C=CHCH$_2$), 7.53 (2H, br d, 2×Ar—H), 8.47 (1H, d, J=7.7 Hz 1×Ar—H).

Synthesis of 3C43

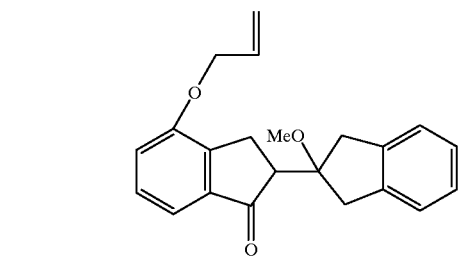

The silyl enol ether of 4-propi-2-enyloxy indan-1-one (1.0 g, 5.3 mmol) and the dimethyl acetal of indan-2-one (1.0 g, 5.6 mmol) were dispersed in clean dry DCM and cooled to −78° C. To this TMS triflate (25 µl) was added and the reaction was stirred at −78° C. for 3 hrs and allowed to stir at room temperature for a further hour. The crude reaction mixture was then passed through a flash silica column, eluting with petroleum ether:ethyl acetate, 9:1. The afforded 3C43 (1.37 g, 77.4%).

$^1$H NMR (CDCl$_3$, 300 MHz) σ$_H$ 3.04–3.08 (4H, m, 2×CH$_2$), 3.24–3.54 (6H, m, CHCH$_2$, CHCH$_2$, OCH$_3$), 4.64 (2H, d J=5.31 Hz, CH$_2$CHCH$_2$), 5.43 (2H, dq, J=1.3 Hz 17.25 Hz, CH=CH$_2$), 6.06–6.17 (1H, m, CHOCH$_2$CHCH$_2$), 7.03 (1H, dd, J=1.3 & 7.05 Hz, Ar—H), 7.15–7.36 (6H, m, Ar—CH).

$^{13}$C NMR (CDCl$_3$, 75.47 MHz) σ$_C$ 26.4, 40.5, 41.5, 68.7 117.7 (5×CH$_2$), 50.9 (CH), 53.3 (OCH$_3$), 87.3 (qC), 115.4, 115.9, 123.9, 124.2, 126.3, 128.5, 132.7 (7×Ar—CH), 139.2, 140.9, 141.4, 142.7, 155.7 (5×Ar—C), 206.1 (C=O).

Synthesis of 4C1

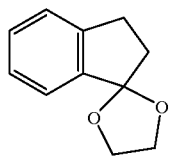

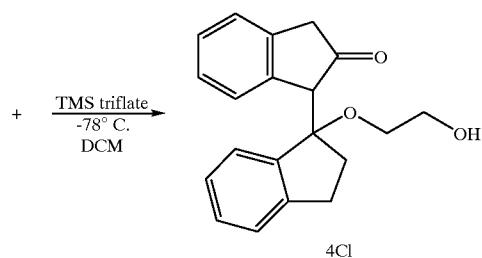

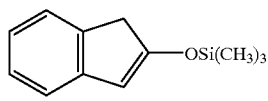

Silyl enol ether of indan-2-one (1 g, 4.9 mmol) and the cyclic ketal of indan-1-one (1 g, 5.6 mmol) were dispersed in clean dry DCM. The solution was cooled to −78° C. and TMS triflate (25 ml) was added. The reaction was stirred at −78° C. for 2 hours and allowed to come to room temperature. The product was extracted into ethyl acetate. Column chromatography was used to isolate the desired product, eluting with petroleum ether:ethyl acetate, 8:2. 4C1 was isolated (1.07 g, 70.9%).

$^1$H NMR (CDCl$_3$ δ$_H$ 2.01 (1H, br s, CH$_2$OH), 2.94–3.04 (4H, m, CH$_2$CH$_2$), 3.67–3.70 (2H, m, CH$_2$), 3.78 (2H, s, COCH$_2$), 4.13–4.18 (2H, m, CH$_2$), 7.06 (1H, t, COCH), 7.23–7.34 (6H, m, Ar—H), 7.50 (1H, d, J=7.4 Hz, Ar—H), 7.64 (1H, t, J=4.6 Hz, Ar—H).

$^{13}$C NMR (CDCl$_3$, 75.47 MHz) δ$_C$ 30.5, 39.3, 60.9 , 66.3 (5×CH$_2$), 116.0 (CH), 120.3, 125.3, 126.6, 126.8, 127.2, 128.4, 128.5, 130.4 (8×Ar—CH), 132.5, 137.5, 141.9, 145.7, 146.1 (4×Ar—C and 1×qC), 171.9 (C=O).

Low resolution mass spec Requires M$^+$308 Found M$^+$308

Synthesis of 4C2

Coupling of 3-Bromo Indan-1-one to the Silyl Enol Ether of Indan-2-one

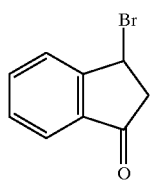

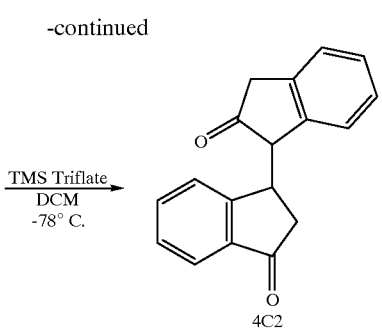

To a stirred solution of the silyl enol ether of indan-2-one (0.8 g, 3.92 mmol) and the corresponding 3-Bromo indan-1-one (0.82 g, 3.92 mmol) in dichloromethane at −78° C., was added a catalytic amount of TMS Triflate (30 μl). The solution was left stirring at −78° C. for 10 min and at room temperature for 3 hours. To this solution was then added solid sodium bicarbonate (approx 2 g) and the solution was stirred rapidly for 10 minutes. The solution was then filtered and the filtrate was evaporated to leave a mobile oil which was passed through a plug of silica elutant with petroleum ether:ethyl acetate, 9:2. After evaporation of the eluent, 4C2 was obtained as a yellow solid, 45%.

Low resolution mass spectra: Found M$^+$262 Require M$^+$262

$^1$H NMR (CDCl$_3$, 300 MHz) δ$_H$ 2.14 (1H, dd, J=3.4 Hz, CHCH$_2$), 2.64 (1H, dd, J=7.68 Hz, CHCH$_2$), 3.42 (2H, q, J=23 Hz, COCH$_2$), 4.10 (1H, br s, CHCOCH$_2$), 4.18 (1H, m, CH$_2$CH) 6.25 (1H, d, J=7.7 Hz, 1×Ar—H), 6.97 (1H, t, 7.2 Hz ,1×Ar—H), 7.25 (2H, m, 2×Ar—H), 7.45 (2H, m, 2×Ar—H), 7.70 (1H, t, J=7.2 Hz, 1×Ar—H), 7.80 (1H, d, J=7.0 Hz, 1×Ar—H).

$^{13}$C NMR (CDCl$_3$, 75.47 MHz) δ$_C$ 38.6, 43.2 (2×CH$_2$), 39.5, 55.5 (2×CH), 123.6, 124.4, 125.0, 125.2, 127.4, 127.5, 128.1, 128.1, 134.9, 137.4, 137.8, 155.2 (8×Ar—CH & 4×Ar—C), 204.5, 215.6 (2×C=O).

Synthesis of 4C3

Sodium Borohydride Reduction of 4C2

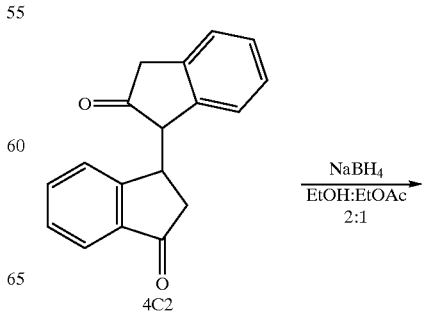

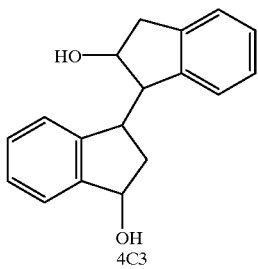

OH
4C3

To a stirred solution of dione 4C2 (100 mg, 0.38 mmol) in ethyl acetate:ethanol (2:1, 9 ml) was added sodium borohydride (100 mg). This solution was left stirring at room temperature for 1 hour. The solution was then concentrated on the rotary evaporator and the concentrate was then passed through a plug of silica eluting with petroleum ether (b.p. 40–60° C.):ethyl acetate 9:1 grading to ethyl acetate. Evaporation of the eluent left the diol 4C3 as a white solid (90 mg, 90%).

Low resolution mass spectra: Found M$^+$262 Required M$^+$262

$^1$H NMR (CDCl$_3$, 300 MHz) δ$_H$ 1.50–3.81 (6H, m, CH & CH$_2$'s), 4.73 and 5.02 (2H, m, 2×CHOH), 7.38 (3H, m, 3×Ar—H), 7.53 (1H, dd, J=1.2 Hz, 1×Ar—H), 7.60 (2H, m, 2×Ar—H), 7.75 (2H, 2×t, J=1.2 Hz, 2×Ar—H).

$^{13}$C NMR (CDCl$_3$, 75.47 Mhz) δ$_C$ 39.1, 41.2 (2×CH2), 42.0, 51.5 (2×CH), 74.5, 74.9 (2×CHOH), 124.0, 124.4, 124.7, 124.9, 125.1, 126.1, 127.0, 128.0 (8×Ar—CH), 141.3, 141.8, 144.7, 145.1 (4×Ar—C).

It will be appreciated that the compounds include pharmacologically acceptable salts, esters, isomers and solvates thereof. One example of a possible ester is a salicylate in at least one and possibly several suitable positions on the compound. This opens up the possibility of a combination therapy using an indane dimer and aspirin in a single molecule. The weight ratio of the base indane dimer to aspirin may be selected by providing a salicylate at a number of selected positions on the dimer.

It will be appreciated most of the compounds have one or more chiral centres and hence exist as a pair of enantiomers or as a mixture of diastereomers. This may have an effect on the pharmacological properties. For example, 3C8 above is a mixture of enantiomers 3C9 is also a mixture of enantiomers. The two enantiomers in 3C8 are diastereomers of the two enantiomers in 3C9. As shown by the data below, the two enantiomers in 3C8 are apparently more pharmacologically active than the two enantiomers in 3C9. Indeed, one of the enantiomers in 3C8 may be more pharmacologically active than the other.

Pharmacology

Introduction

The indane dimers according to the invention have potent mast cell stabilising activity, smooth muscle relaxing activity, and anti-inflammatory activity. The compounds are, therefore, potential anti-asthmatic agents with bronchodilator activity. The mast cell stabilising activity of the compounds suggests their potential use in the treatment of allergic rhinitis, allergic conjunctivitis and other anaphylactic or allergic conditions. The anti-inflammatory activity may have applications in gout, rheumatic diseases, ankylosing spondylitis, polymyalgia rheumatica, temporal arteritis, polyarteritis nodosa, polymyositis and systemic lupus arteriosis and other inflammatory conditions. Topical applications may include: atopic excema, weeping excemas psoriasis, chronic discoid lupus erythematosus, lichen simplex chronicus, hypertrophic lichen planus, palmar plantar pustulosis. They may also have potential in the treatment of some malignant diseases and as immunosuppressants.

The smooth muscle relaxing activity of the compounds may have potential in the treatment of hypertension and peripheral vascular disease, such as intermittent claudication and Reynaud's syndrome, as well as other cardiovascular disorders, such as congestive heart failure, angina pectoris, cerebral vascular disease and pulmonary hypertension. Such compounds are also indicated for potential use in the treatment of certain disorders of the gastro-intestinal tract, such as diverticular disease and irritable bowel syndrome. Similarly, these compounds may have potential as agents for the treatment of disorders of the genito-urinary tract, such as premature labour, incontinence, renal colic and disorders associated with the passage of kidney stones. Members of this group of compounds may also have potential as diuretics, analgesics, antipyretics, local anaesthetics, central nervous system depressants and hypoglycaemic agents.

The compounds were assessed for their ability to stabilize mast cell membranes in vitro. Mast cells treated with the compounds and un-treated mast cells were stimulated to release histamine. A reduction in histamine release by the treated cells compared to the un-treated cells indicates stabilisation of the membrane. The compounds were assessed for their ability to relax smooth muscle in vitro. Smooth muscle was stimulated to contract, using calcium chloride, and subsequently treated with the compounds, and relaxation of the contraction was measured for each compound. The compounds which showed the most activity in these assays were tested for mutagenicity using the Salmonella mutagenicity test (plate incorporation assay). One of these (3C8) was further assessed using an in vivo asthma model. Sensitised rats were treated with the drug by aerosol prior to challenge with allergen and alterations in respiration were recorded. As a result of this study further tests were carried out to determine the anti-inflammatory activity of 3C8. In the rat paw oedema test, the drug was administered systemically prior to inducing inflammation by the injection of carageenan below the plantar aponeurosis of the hind paw. The volume of the paw was determined both before and after treatment as an index of oedema. In the mouse ear oedema test, the drug was administered topically prior to inducing inflammation by the topical application of arachidonic acid. The width of the ear was determined both before and after treatment as an index of oedema. The ability of 3C8 to prevent oedema was determined.

There follows protocols of each of these assays and a summary of the results.

| ABBREVIATIONS | |
|---|---|
| BSS | buffered salt solution |
| CaCl$_2$ | calcium chloride |
| CO$_2$ | carbon dioxide |
| DMSO | dimethyl sulphoxide |
| DSCG | disodium cromoglycate |
| dH$_2$O | distilled water |
| Hcl | hydrochloric acid |
| HEPES | N-2-hydroxyethylpiperazine-n-2-ethanesulphonic acid |
| KCl | postassium chloride |
| 1$_{em}$ | emission wavelength |
| 1$_{ex}$ | excitation wavelength |
| M | Molar |
| MgCl$_2$ | magnesium chloride |
| min | minutes |

-continued

| ABBREVIATIONS | |
|---|---|
| ml | microliters |
| mM | milli-molar |
| NaCl | sodium chloride |
| NaHCO$_3$ | sodium hydrogen carbonate |
| NaH$_2$PO | sodium hydrogen phosphate |
| NaOH | sodium hydroxide |
| O$_2$ | oxygen |
| oPT | o-phthaldialdehyde |
| S.E.M. | standard error of mean |
| w/v | weight per volume |
| v/v | volume per volume |

Methods
Histamine Release Assay

The buffered salt solution (BSS) was prepared in advance (NaCl 137 mM; KCl 2.7 mM; MgCl$_2$ 1.0 mM; CaCl$_2$ 0.5 mM; NaH$_2$PO$_4$ 0.4 mM; Glucose 5.6 mM; HEPES 10 mM). This was dispensed into test tubes and heated to 37° C., each test tube contained 4.5 ml BSS. The solvent blank was supplemented with 0.5% (v/v) dimethyl sulphoxide (DMSO) or 0.5% (v/v) distilled water (dH$_2$O). The two positive controls were supplemented with 0.5% (v/v) dH$_2$O/ 2×10$^{-5}$M disodium cromoglycate (DSCG) and 0.5% (v/v) DMSO/2×10$^{-5}$M DSCG. The test compounds' incubation tubes contained 2×10$^{-5}$M test compound 1 0.5% (v/v) DMSO. The basal release, maximum release and total histamine content incubation tubes contained no additions.

Female Wistar rats (200–300 g) were killed in an atmosphere of saturated CO$_2$. Pre-warmed BSS (10 ml) was injected i.p. and the abdomen was massaged for 3 min. The BSS, with suspended mast cells and other cells, was aspirated following a mid-line incision. The aspirate was centrifuged for 5 min at 400 g and the supernatent removed. The cells were re-suspended in BSS, at 4° C., and centrifuged as before. The cells were washed in this manner a total of three times. Following the final wash, the pelleted cells were stored at 4° C., for use as soon as possible.

The cells were re-suspended in 7 ml BSS. From this, 0.5 ml aliquots were transferred to each of the incubation tubes. After 10 min at 37° C., with gentle agitation, Compound 48/80 was added to a final concentration of 2 mg/ml, in order to stimulate histamine release. The cell stimulation was stopped after 2 min by the addition of 0.5 ml ice cold BSS, the incubation tubes were transferred to an ice bath. The cell suspensions were centrifuged for 5 min at 400 g. The "total histamine content" tube was placed at 100° C. for 2 min prior to centrifugation. The supernatants were retained for histamine assay.

To 2 ml of supernatent from each tube was added 0.4 ml of 1M NaOH and 0.1 ml oPT (1% (w/v) in methanol). This was incubated at room temperature for 4 min. The reaction was stopped by the addition of 0.2 ml of 3M HCl. The supernatant from each incubation tube was assayed in duplicate and run simultaneously with a standard curve in the range 0–1000 ng/ml. The presence of the fluorescent product of the reaction was measured using a Shimadzu RF-1501 spectrofluorophotometer set at $\lambda_{ex}$=360 nm, $\lambda_{em}$=450 nm.

Each drug was tested on at least five animals (n=5). The results were expressed as a percentage of maximum inhibition of compound 48/80 induced-histamine release in the solvent blank sample. Each drug was compared to DSCG on the same tissues. The basal histamine release in untreated cells was noted, expressed as a percentage of the total histamine content of the cells in suspension. The maximum histamine released by the cells in response to compound 48/80, in the relevant solvent blank sample, was expressed in the same manner,. Overall, the mean basal release was 9.60% (S.E.M.=1.02) of total histamine content of the cells (n=55). The maximum stimulated histamine release was 67.38% (S.E.M.=2.90) in the presence of 0.5% (v/v) dH$_2$O and 54.87% (S.E.M.=2.69) on the presence of 0.5% (v/v) DMSO of total histamine content of the cells (n=55).

Smooth Muscle Effects

Guinea pigs (350 g approx.), of either sex, were killed in an atmosphere of saturated CO$_2$. The abdomen was opened by a mid-line incision and the small intestine was removed.

Segments of ileum (1–1.5 cm) were suspended in a high potassium, no calcium Krebs buffer (NaCl 160.4 mM; KCl 45 mM; MgCl$_2$ 0.54 mM; NaH$_2$PO$_4$ 0.89 mM; NaH$_2$CO$_3$ 24.9 mM, Glucose 11.1 mM). This was maintained at 37° C. by a jacketed organ bath and gassed with 95% O$_2$ and 5% CO$_2$. The tissues were anchored by thread to the bottom of the organ bath and suspended from force displacement transducers under a resting tension of 1 g approx. Isotonic contractions were recorded using a MacLab/4e system in conjunction with the Chart 3.3.1 software package. Surplus tissue was stored at 4° C. in Krebs buffer (NACl 236.5 mM; KCl 4.7 mM; CaCl$_2$ 2.5 mM; MgCl$_2$ 0.54 mM; NaH$_2$PO$_4$ 0.89 mM; NaHCO$_3$ 24.9 mM; Glucose 11.1 mM), for a maximum of 48 hours.

Four segments of tissue were suspended and observed concurrently. Contractions were initiated by the addition of 25 µl of 1M CaCl$_2$ (a final concentration of 2.5 mM). The contractions stabilized with time, 10–15 min, and could be maintained for up to 45 min. from the addition of the CaCl$_2$.

Stock solutions of drug were prepared at 10$^{-3}$M in 50% (v/v) DMSO. These were diluted to give; 10$^{-4}$M in 5% (v/v) DMSO and 10$^{-5}$M in 0.5% (v/v) DMSO. In cases of poor solubility the 10$^{-3}$M stock was made up in higher concentrations of DMSO. Solvent "blank" solutions were prepared containing 50%, 5% and 0.5% (v/v) DMSO (or as appropriate). The drug solution was added to the organ bath once a stable contraction of the tissue had been achieved. A cumulative dose-response assay was carried out in the range 5×10$^{-8}$M to 10$^{-5}$M. The organ bath was washed out and the tissue allowed to relax. A second cumulative dose-response assay was carried out using DMSO "blank" solutions only.

Each drug was tested, in duplicate, on at least three different animals (n=3). The results were expressed as percentage inhibition of the CaCl$_2$ induced contraction, for each tissue, at each concentration of drug in DMSO. The effect of DMSO, for each tissue at each concentration, was substracted from the effect of the drug in DMSO, to give the effect of the drug alone. A log dose vs. response curve was plotted for each drug using the mean and the standard error of the mean for the cumulated results.

Salmonella Mutagenicity Test

The compounds were tested for mutagenicity under the protocol designed by Ames et al. (Mutation Res. 31, 347–364, 1975) and modified by Maron and Ames (Mutation Res. 113, 173–215, 1983). The *Salmonella Typhimurium* LT2 histidine requiring strains TA98, TA100, TA102 and TA1535 were used for mutagenicity testing. These strains contain a number of other mutations which greatly increase their ability to detectmuta gens. These are (1) a mutation (rfa$^+$) causing partial lots of the lipopolysaccharide cell wall, thus increasing the permeability of the cell to larger molecules and (2) a deletion (uvrB$^-$) causing loss of the DNA excision repairs systems. TA102 retains the excision repair system (uvrB$^+$), rendering it capable of detecting mutagens needing this system. In addition, TA102 contains the PAQ1 plasmid, with the his G428 mutation, confering tetracycline resistance to this strain. TA98, TA100 and TA102 also embody an R factor plasmid, PKM101, containing an ampicillin resistance gene. Mutation of the genome, causing revertion to histidine independence can be detected using selection media.

Solutions of the test compounds were prepared in DMSO in the range 0–50 mg/ml. Top agar (2 ml), held at or above 45° C., containing 0.5 mM L-histidine HCl/0.5 mM biotin, was distributed into sterile 5 ml sample vials. Fresh overnight culture of the relevant strain (0.1 ml) was added along with the test compound (0.1 ml). Rat liver microsomal enzymes may also be included (0.5 mls of S9 mix) in order to test for mutagenic metabolites of the test compounds. The contents of the sample vial were transferred onto minimal glucose agar plates and left stand to dry for one hour. The plates were inverted and incubated at 37° C. for 48 h. Cell growth take place only in the event of a mutation occuring. The number of revertant colonies on each plate were counted. Six negative control plates, including DMSO, and six positive control plates, including a diagnostic mutagen, were tested concurrently with each compound. Three to four test plates were conducted for each compound at each of five different ocncentrations. A significant rise in the number of revertant colonies on a test plate compared to the background revertion rate would indicate that the test compound was mutagenic. Significance testing was carried out using Dunnett's multiple comparison test (Dunnett C. W., Jnl. Am. Statist. Assoc. 50, 1096–1121, 1955).

In vivo Bronchial Asthma Model

Experiments were performed in male wistar rats aged 10–12 weeks (200–250 g). Sensitisation was by the injection (1 ml s.c.) of ovalbumin (1 mg/ml)/aluminium hydroxide (200 mg/ml) and Freunds complete adjuvant (1 ml i.p.).

Three weeks following sensitisation, each animal was sedated with sodium phenobarbitone (40 mg/kg i.p.), sedation was maintained with supplemental injections (5 mg/kg i.p.) as required. The nose was occluded by surgical tape to prevent deposition of aerosols. The animal was placed in a respiratory chamber, respiratory parameters were measured by a differential volumetric transducer. Animals were treated by an aerosol of ethanol (50% v/v as a negative control), DSCG (5 mg/ml in ethanol 50% v/v as a positive control) or 3C8 (5 mg/ml in ethanol 50% v/v). The animals were subsequently challenged by an aerosol of saline (negative control) or ovalbumin (5% w/w). Changes in respiration were monitored for three hours. Each animal was given three further such treatments to induce bronchial hyper-reactivity, a condition more closely resembling bronchial asthma.

Three to four weeks after the initial treatment, the experiment was repeated. The animals were exposed to an aerosol of acetyl-methyl-choline (metacholine) at a dose (8 mg/ml), which stimulates a significant response in hyper-reactive airways only. None of the animals were pre-treated with drug. Changes in airway responses were monitored for one hour.

In vivo Inflammation Models

The rat paw oedema model was performed using female Wistar rates (180–200 g). The animals were sedated with sodium pentobarbitone, 40–70 mg/kg i.p. The animals were treated by the i.p. injection of one of a range of concentrations of test drug (0–100 mg/kg in 50% DMSO) or hydrocortisone (100 mg/kg in 50% DMSO) or indomethacin (100 mg/mk in 50% DMSO). After 30 min, oedema was induced by the injection of carageenan (100 $\mu$l at 2% w/v) below the plantar aponeurosis of the hind paw. The volume of the paw was measured, both before and 60 min after treatment, by displacement of water in a graduated cylinder. Paw oedema was calculated by comparing the paw volume before a and after induction of oedema and expressed as percentage normal.

The mouse ear oedema model was performed using Laca mice (25–35 g), of either sex. The animals were sedated with fentanyl/fluanizone (Hypnorm, Janssen). One ear was treated by the topical application of one of a range of test compounds, indomethacin or dexamethazone (all at 300 $\mu$g ear in acetone) drug. After 30 min, oedema was induced by the topical application of arachidonic acid (10 $\mu$l at 0.4 g/ml in acetone). The thickness of each ear was measured, both before and 60 min after the induction of oedema, using a micrometer screw guage. Ear oedema was calculated by comparing the ear width before and after induction of oedema and expressed as percentage normal.

Results

Mast Cells Stabalisatin and Smooth Muscle Relaxation

The findings of the histamine release and the smooth muscle effect assays are summarised in the acompanying tables of results. The results from some of the compounds are illustrated in the accompanying graphs. The results indicate that these compounds show a wide variety of smooth muscle relaxing and mast cell stabilising activity, and that these two effects are not related (i.e. a good mast cell stabiliser is not necessarily a good smooth muscle relaxant and vice versa).

Results for Histamine release assay and Smooth muscle

Percentage Inhibition of:

| Conc. (M) | CaCl2 Induced Contractions ($\pm$S.E.M.) | | | | | | Histamine Release ($\pm$S.E.M.) |
|---|---|---|---|---|---|---|---|
| | $5 \times 10^{-8}$ | $10^{-7}$ | $5 \times 10^{-7}$ | $10^{-6}$ | $5 \times 10^{-6}$ | $10^{-5}$ | $2 \times 10^{-5}$ |
| 1C1 | 0.39 ± 0.79 | 0.03 ± 0.90 | 0.79 ± 0.66 | 0.66 ± 0.68 | 1.83 ± 1.46 | 7.95 ± 2.47 | 3.62 ± 4.69 |
| 1C2 | 0.91 ± 1.23 | 0.29 ± 1.52 | 1.92 ± 3.07 | 6.45 ± 3.86 | 21.62 ± 3.91 | 41.27 ± 3.84 | 15.55 ± 3.23 |
| 1C3 | 1.89 ± 1.38 | 2.29 ± 1.36 | 2.45 ± 2.48 | 5.71 ± 3.20 | 15.50 ± 3.55 | 29.52 ± 4.79 | 15.98 ± 1.90 |
| 1C4 | −1.03 ± 0.99 | −2.36 ± 0.59 | −3.00 ± 0.91 | −4.03 ± 1.63 | −3.75 ± 2.05 | −5.17 ± 2.46 | 23.05 ± 2.24 |
| 1C5 | 3.04 ± 1.16 | 4.75 ± 2.13 | 5.43 ± 3.24 | 13.13 ± 4.46 | 27.07 ± 3.86 | 44.86 ± 3.73 | |

-continued

Results for Histamine release assay and Smooth muscle

Percentage Inhibition of:

| Conc. | CaCl2 Induced Contractions (±S.E.M.) | | | | | | Histamine Release (±S.E.M.) |
|---|---|---|---|---|---|---|---|
| (M) | $5 \times 10^{-8}$ | $10^{-7}$ | $5 \times 10^{-7}$ | $10^{-6}$ | $5 \times 10^{-6}$ | $10^{-5}$ | $2 \times 10^{-5}$ |
| 1C6 | 2.81 ± 0.50 | 3.88 ± 0.54 | 5.11 ± 1.02 | 9.84 ± 2.11 | 21.91 ± 2.63 | 45.50 ± 4.04 | 6.13 ± 3.93 |
| 1C12 | 2.60 ± 2.18 | 1.28 ± 1.71 | 2.60 ± 1.65 | 3.68 ± 2.30 | 33.09 ± 3.49 | 51.26 ± 1.99 | 16.64 ± 1.71 |
| 1C13 | 1.73 ± 0.72 | 2.64 ± 1.14 | 8.55 ± 2.17 | 14.68 ± 2.66 | 39.34 ± 3.10 | 51.70 ± 3.71 | 37.79 ± 4.85 |
| 1C24 | 0.72 ± 0.61 | 1.07 ± 0.74 | 2.36 ± 1.22 | 3.05 ± 1.40 | 12.38 ± 2.70 | 18.86 ± 3.17 | 24.72 ± 3.22 |
| 1C25 & 1C26 | 0.19 ± 0.61 | 1.48 ± 0.92 | 3.22 ± 1.22 | 5.97 ± 1.48 | 21.32 ± 3.20 | 36.14 ± 2.82 | 41.40 ± 8.33 |
| 1C28 | 0.31 ± 0.94 | 3.29 ± 0.90 | −1.05 ± 0.83 | −3.21 ± 0.68 | −2.26 ± 1.11 | −2.49 ± 0.58 | 10.27 ± 3.73 |
| 1C29 | 0.76 ± 1.37 | 0.34 ± 1.22 | 0.44 ± 0.60 | 2.37 ± 0.74 | 12.47 ± 3.44 | 21.00 ± 3.69 | 21.62 ± 3.90 |
| 1C31 | 1.22 ± 1.09 | −0.61 ± 1.08 | 0.80 ± 1.77 | 4.90 ± 2.06 | 12.95 ± 2.25 | 31.53 ± 2.53 | −27.78 ± 7.68 |
| 1C36 | −0.56 ± 0.50 | −1.29 ± 0.69 | −0.05 ± 0.96 | −3.09 ± 1.23 | −1.26 ± 2.26 | −1.31 ± 3.54 | 16.63 ± 2.15 |
| 2C2 | 1.07 ± 0.48 | 0.45 ± 0.66 | 1.09 ± 1.47 | 3.31 ± 1.29 | 22.42 ± 5.00 | 33.36 ± 4.62 | 22.41 ± 4.99 |

Percentage Inhibition of:

| Conc. | CaCl2 Induced Contractions (±S.E.M.) | | | | | | Histamine Release (±S.E.M.) |
|---|---|---|---|---|---|---|---|
| (M) | $3 \times 10^{-8}$ | $10^{-7}$ | $3 \times 10^{-7}$ | $10^{-6}$ | $3 \times 10^{-6}$ | $10^{-5}$ | $2 \times 10^{-5}$ |
| 1C8 | | | | | | | 35.93 ± 8.06 (n = 4) |
| 1C9 | | | | | | | 64.14 ± 3.87 |
| 1C10 | 1.15 ± 0.55 | 1.40 ± 1.05 | 4.35 ± 0.86 | 9.48 ± 1.59 | 26.53 ± 1.78 | 49.64 ± 1.71 | 19.43 ± 1.98 |
| 1C11 | 0.22 ± 0.60 | 1.67 ± 0.62 | 1.29 ± 1.13 | 2.77 ± 1.62 | 9.59 ± 1.66 | 23.38 ± 1.81 | −5.57 ± 7.20 |
| 1C14 | 0.63 ± 0.35 | 1.86 ± 0.79 | 2.51 ± 0.54 | 3.72 ± 0.66 | 8.53 ± 1.38 | 21.68 ± 2.65 | 24.80 ± 3.93 |
| 1C15-T | −0.45 ± 0.67 | 1.14 ± 0.88 | 3.27 ± 1.41 | 5.82 ± 1.71 | 12.45 ± 2.38 | 26.88 ± 4.08 | −21.64 ± 4.61 |
| 1C15-B | 3.48 ± 1.78 | 4.95 ± 1.90 | 9.73 ± 1.21 | 22.12 ± 3.30 | 41.97 ± 2.42 | 79.51 ± 2.60 | −35.52 ± 6.32 |
| 1C16 | | | | | | | 74.45 ± 3.06 |
| 1C17 | −1.40 ± 0.90 | −1.98 ± 1.62 | −1.58 ± 1.30 | 0.31 ± 2.43 | 8.02 ± 3.30 | 35.19 ± 2.85 | −23.14 ± 9.73 |
| 1C18 | 1.73 ± 0.52 | 1.46 ± 0.43 | 3.27 ± 0.87 | 6.09 ± 1.21 | 22.04 ± 3.35 | 39.54 ± 6.91 | −28.83 ± 2.15 |
| 1C19 | | | | | | | 27.77 ± 7.40 |
| 1C20 | −1.80 ± 0.88 | 1.79 ± 1.55 | 3.60 ± 2.44 | 4.25 ± 2.95 | 6.81 ± 2.84 | 19.90 ± 1.44 | 32.49 ± 3.05 |
| 1C21 | 1.32 ± 1.44 | 0.72 ± 1.59 | 1.94 ± 2.24 | 3.73 ± 3.63 | 5.06 ± 3.68 | 17.95 ± 2.92 | −3.17 ± 12.02 |
| 1C22 | 1.17 ± 1.19 | 1.16 ± 1.99 | 1.72 ± 2.86 | 2.68 ± 3.64 | 7.43 ± 4.81 | 26.78 ± 6.06 | 42.90 6.13 |
| 1C23 | 0.05 ± 1.11 | −0.72 ± 0.53 | 0.06 ± 0.60 | 3.37 ± 0.60 | 6.63 ± 1.03 | 24.42 ± 1.99 | 56.53 ± 8.04 |
| 1C27 | | | | | | | 23.52 ± 8.35 |
| 1C30 | 2.63 ± 1.68 | 4.54 ± 1.66 | 6.79 ± 1.81 | 12.32 ± 1.85 | 20.27 ± 2.11 | 36.26 ± 3.61 | 8.65 ± 5.09 |
| 1C32 | 0.89 ± | 0.99 ± | 2.90 ± | 2.27 ± | 0.73 ± | 2.90 ± | 10.26 ± |

-continued

| | Percentage Inhibition of: | | | | | | |
|---|---|---|---|---|---|---|---|
| | CaCl2 Induced Contractions (±S.E.M.) | | | | | | Histamine Release (±S.E.M.) |
| Conc. (M) | $3 \times 10^{-8}$ | $10^{-7}$ | $3 \times 10^{-7}$ | $10^{-6}$ | $3 \times 10^{-6}$ | $10^{-5}$ | $2 \times 10^{-5}$ |
| 1C33 | 0.37 ± 0.71 | 0.75 ± 0.70 | 0.78 ± 1.86 | 0.77 ± 1.95 | 0.88 ± 2.14 | 3.99 ± 1.44 | 2.27 ± 4.40 |
| 1C35 | 1.03 ± 1.16 | 2.22 ± 1.60 | 5.06 ± 2.58 | 6.54 ± 3.09 | 10.24 ± 3.01 | 20.53 ± 3.58 | 21.87 ± 3.24 |
| | −1.94 ± | −4.01 ± | −3.51 ± | −4.43 ± | −2.32 ± | −2.45 ± | 4.48 ± |
| 1C38 | 0.95 ± 0.44 | 2.23 ± 0.86 | 2.95 ± 1.19 | 5.29 ± 1.62 | 7.18 ± 1.40 | 16.84 ± 1.72 | 33.73 ± 5.28 |
| 1C39 | 1.00 ± 0.62 | 3.10 ± 0.89 | 4.12 ± 0.97 | 4.23 ± 0.71 | 4.50 ± 0.87 | 2.59 ± 1.43 | 21.03 ± 8.27 |
| 1C40 | 2.19 ± 1.00 | 2.57 ± 1.41 | 4.62 ± 1.33 | 5.78 ± 0.98 | 7.37 ± 1.31 | 14.10 ± 2.69 | 26.78 ± 7.04 |
| 1C42 | | | | | | | 78.44 ± 4.25 |
| 2C1 | 1.51 ± 0.78 | 2.52 ± 0.92 | 3.21 ± 1.19 | 3.60 ± 1.31 | 4.80 ± 1.15 | 9.07 ± 1.49 | 14.96 ± 5.27 |
| 2C4 | 2.01 ± 0.95 | 2.45 ± 1.51 | 3.21 ± 1.41 | 4.85 ± 1.50 | 11.03 ± 1.68 | 23.16 ± 1.37 | 16.16 ± 11.54 |
| 2C8 | | | | | | | 56.51 ± 2.03 |
| 2C9 | | | | | | | 26.78 ± 7.71 |
| 3C1 | 0.10 ± 0.26 | −1.01 ± 0.62 | 0.09 ± 0.84 | 2.59 ± 1.27 | 5.77 ± 1.44 | 21.35 ± 2.08 | 9.50 ± 2.49 |
| 3C2 | 3.47 ± 1.44 | 3.92 ± 1.65 | 4.70 ± 2.07 | 6.74 ± 3.26 | 9.01 ± 2.94 | 17.70 ± 2.83 | 26.78 ± 7.04 |
| 3C3 | 2.25 ± 0.78 | 4.69 ± 1.21 | 5.91 ± 1.70 | 8.50 ± 2.70 | 15.22 ± 3.76 | 31.76 ± 2.78 | 4.56 ± 4.63 |
| 3C4 | −0.20 ± 0.42 | −1.56 ± 1.22 | 0.13 ± 1.37 | 4.46 ± 1.69 | 9.40 ± 1.49 | 23.36 ± 2.03 | 22.81 ± 8.44 |
| 3C5 | 0.54 ± 0.64 | 2.38 ± 1.49 | 0.86 ± 1.33 | 2.91 ± 1.69 | 7.50 ± 1.55 | 14.57 ± 1.94 | 7.10 ± 6.21 |
| 3C6 | 0.33 ± 0.89 | 1.76 ± 0.97 | 6.00 ± 1.17 | 10.95 ± 1.18 | 23.92 ± 3.56 | 45.47 ± 4.87 | 57.88 ± 3.13 |
| 3C7 | 2.83 ± 1.54 | 5.23 ± 1.30 | 8.11 ± 1.61 | 10.72 ± 1.79 | 20.73 ± 3.18 | 46.67 ± 6.02 | 42.05 ± 5.87 |
| 3C8 | 6.69 ± 1.28 | 9.36 ± 1.29 | 10.35 ± 1.28 | 14.46 ± 2.37 | 22.15 ± 4.32 | 53.37 ± 3.51 | 88.69 ± 1.53 |
| 3C9 | 5.96 ± 1.41 | 4.42 ± 1.71 | 4.27 ± 1.89 | 5.73 ± 1.80 | 9.61 ± 2.40 | 18.88 ± 2.16 | 75.74 ± 2.22 |
| 3C10 | | | | | | | 22.59 ± 4.80 |
| 3C11 | 2.52 ± 1.89 | 1.79 ± 1.82 | 1.62 ± 2.29 | 3.25 ± 1.73 | 4.75 ± 2.22 | 10.90 ± 4.39 | −45.60 ± 32.56 |
| 3C12 | −0.74 ± 1.17 | −1.68 ± 2.52 | 5.58 ± 3.00 | 6.76 ± 2.62 | 14.16 ± 2.33 | 23.66 ± 2.16 | −3.91 ± 7.04 |
| 3C13 | 2.51 ± 0.72 | 3.47 ± 0.85 | 6.41 ± 1.26 | 7.98 ± 1.88 | 11.18 ± 1.67 | 24.34 ± 2.36 | 16.98 ± ±4.97 |
| 3C17 | 0.90 ± 0.88 | −0.94 ± 0.70 | 0.87 ± 0.45 | 1.77 ± 0.80 | 4.04 ± 2.08 | 20.24 ± 2.78 | 47.50 ± 10.49 |
| 3C18 | −0.75 ± 0.81 | 0.74 ± 1.98 | 2.42 ± 2.46 | 3.90 ± 3.31 | 8.15 ± 3.36 | 20.77 ± 3.73 | −59.75 ± 14.09 |
| 3C19 | 2.75 ± 0.85 | 5.51 ± 2.07 | 5.74 ± 1.88 | 9.18 ± 2.61 | 14.14 ± 2.82 | 21.19 ± 2.04 | −18.69 ± 5.71 |
| 3C20 | 0.81 ± 0.87 | 1.40 ± 0.84 | 1.04 ± 0.55 | 0.90 ± 1.19 | 2.76 ± 1.48 | 10.30 ± 2.80 | −54.52 ± 8.53 |
| 3C21 | 0.19 ± 1.32 | 1.45 ± 1.59 | 1.72 ± 1.92 | 5.01 ± 2.43 | 8.02 ± 3.82 | 19.99 ± 4.90 | −14.48 ± 4.50 |
| 3C25 | 3.02 ± 1.29 | 3.03 ± 1.24 | 5.92 ± 2.40 | 10.49 ± 3.54 | 17.33 ± 1.71 | 36.58 ± 2.43 | −0.46 ± 2.61 |
| 3C34 | 1.85 ± 0.48 | 3.31 ± 0.70 | 4.87 ± 0.83 | 7.24 ± 1.15 | 14.41 ± 1.83 | 31.71 ± 3.19 | −35.74 ± 4.87 |
| 3C35 | 0.19 ± 0.59 | −0.12 ± 0.89 | 0.80 ± 0.67 | 2.13 ± 1.05 | 7.59 ± 2.08 | 15.27 ± 2.46 | −50.90 ± 5.34 |
| 3C43 | | | | | | | 64.04 ± 8.37 (n = 3) |
| 4C2 | 4.91 ± 2.12 | 8.13 ± 3.07 | 11.95 ± 3.22 | 16.86 ± 3.07 | 26.28 ± 3.02 | 40.11 ± 1.04 | 15.73 ± 4.88 |
| 4C3 | −1.43 ± 0.68 | −0.05 ± 1.28 | −0.46 ± 1.10 | −0.31 ± 1.44 | 4.50 ± 1.95 | 14.25 ± 3.01 | −2.20 ± 4.61 |
| 2C12 | 5.32 ± 1.61 | 8.59 ± 2.73 | 8.56 ± 2.50 | 11.67 ± 1.51 | 17.31 ± 1.73 | 32.77 ± 3.84 | −8.70 ± 2.89 |

-continued

| Conc. | Percentage Inhibition of: | | | | | | |
|---|---|---|---|---|---|---|---|
| | CaCl2 Induced Contractions (±S.E.M.) | | | | | | Histamine Release (±S.E.M.) |
| (M) | $3 \times 10^{-8}$ | $10^{-7}$ | $3 \times 10^{-7}$ | $10^{-6}$ | $3 \times 10^{-6}$ | $10^{-5}$ | $2 \times 10^{-5}$ |
| 2C14 | | | | | | | 38.08 ± 7.68 |
| 3C30 | | | | | | | 4.26 ± 6.80 |
| 3C32 | | | | | | | 22.34 ± 2.51 |

Toxicology

Following the salmonella mutagenicity test, 1C13, 1C14, 1C25/26 and 3C8 did not significantly increase the number of revertant colonies in the *Salmonella typhimurium* LT2 strains TA98, TA100, TA102 and TA1535 at concentrations up to 5 mg/plate, in the presence or absence of the liver microsomal enzymes (S9 mix). The compound 3C9did not significantly increase the number of revertant colonies in the *Salmonella typhimurium* LT2 strain TA98, incubated without the S9 mix, at concentrations up to 5 mg/plate. It was concluded that 1C13, 1C14, 1C25/26, 3C8 and 3C9 are not mutagenic, using the above mentioned concentrations and bacterial strains, according to the Ames salmonella mutagenicity test.

Bronchial Asthma Model

All animals responded to aerosol treatment with a 30% drop in rate of respiration and a 50% drop in tidal volume, regardless of the content of the aerosolised solution. This may well have masked the early response of animals exposed to ovalbumin, since none was observed. The animals were divided into four treatment groups:

Group I—Negative Control

Figure 2:
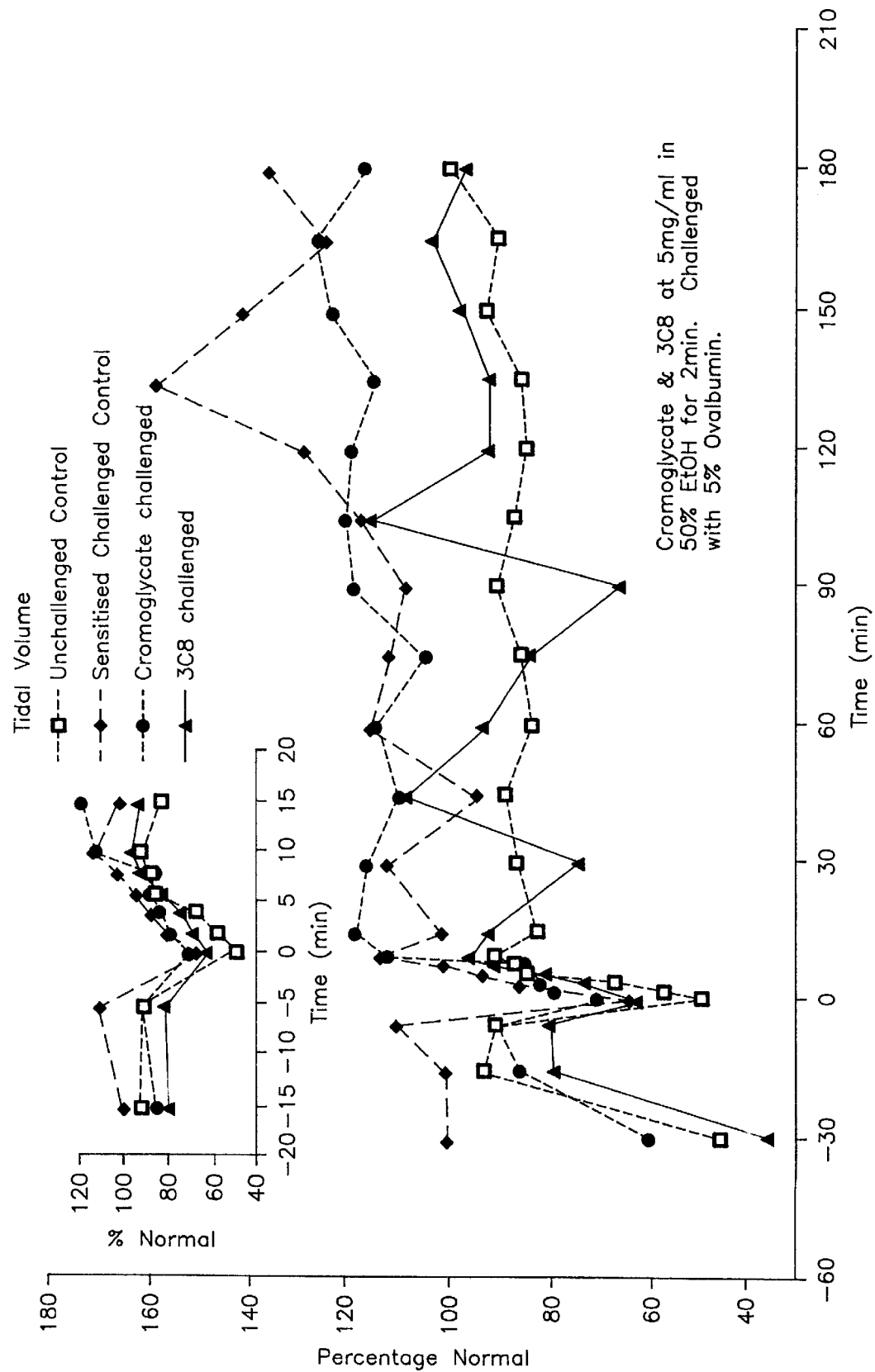
Figure 3:
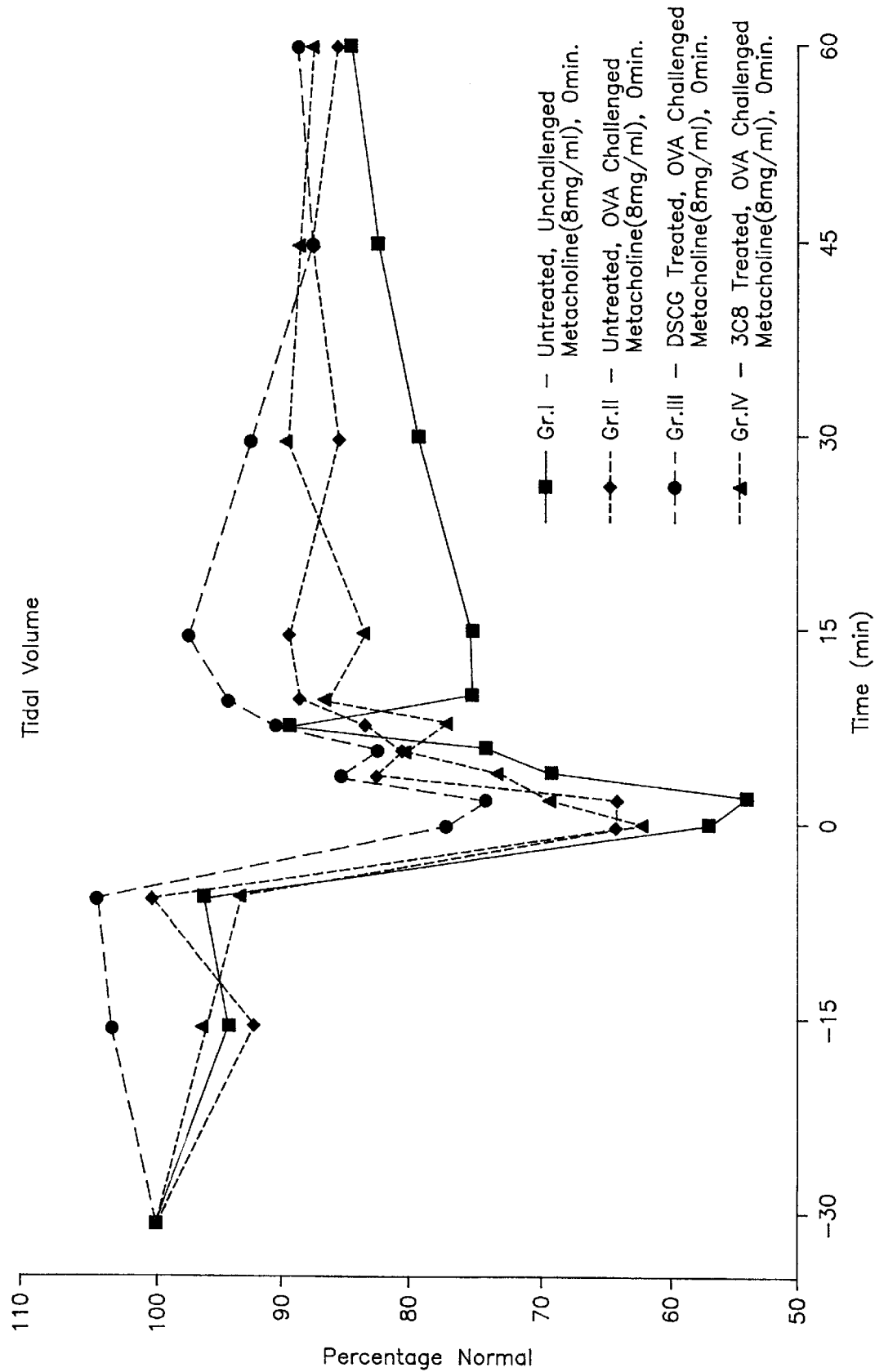
Figure 4:
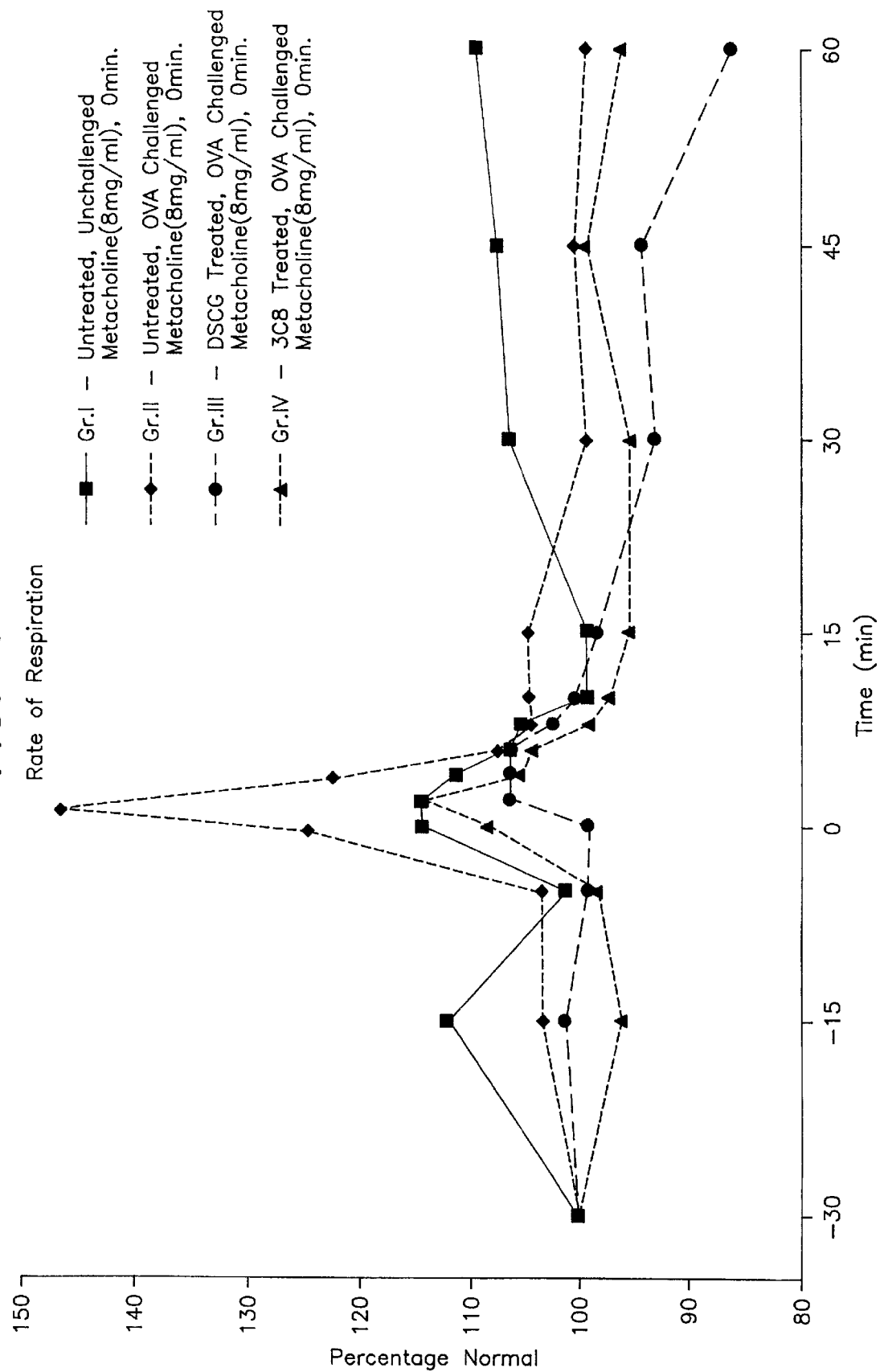

These animals were exposed to ethanol (50% v/v) by aerosol 30 min prior to exposure to saline (NaCl 0.9% w/v), also by aerosol. There was a fall in respiration rate of 30% and in tidal volume of 50%, in response to the aerosol. Both parameters returned to normal within 10 min and remained normal throughout the monitoring period. (FIG. 1) Following exposure to metacholine the tidal volume fell by 50% but the respiration rate rose by 10%. (FIG. 2) This may indicate a response to the metacholine insufficient to overcome the expected response to the aerosol. A response to metacholine was not anticipated given that the animals were not treated with allergen.

Post-mortem examination revealed that the animals had all developed severe sterile peritonitis. This took the form of extensive, vascularised fibrosis within the abdomen, particularly around the liver and upper intestines. In addition, small, caseous nodules developed, again primarily around the liver, but also scattered throughout the abdomen with an occasional focus at the injection sites. This is thought to have developed as a result of multiple i.p. injections of phenobarbitone, an acidic irritant.

Group II—Positive Control

These animals were exposed to ovalbumin (5% w/v) by aerosol. There was a fall in respiration rate of 35% and in tidal volume of 40%, in response to the aerosol. The early phase of the allergic response to the ovalbumin is masked by the aerosol effect. Both parameters returned to normal within 10 min and remained normal for 100 min. Two hours (120 min) following exposure to ovalbumin the rate of respiration rose by 35% and the tidal volume rose by 60%. This represents the late phase of the allergic response. Both parameters returned to normal within 30 min and remained normal for the rest of the monitoring period. (FIG. 1) Following exposure to metacholine the tidal volume fell by 35% but the respiration rate rose by 50%. This indicates a response to the metacholine sufficient to overcome the expected response to the aerosol and implies that multiple exposures to allergen (ovalbumin) have induced hyper-reactivity in the airway. Both parameters returned to normal in 10 min and remained normal during the monitoring period. (FIG. 2) Post-mortem examination revealed that the animals had all developed severe sterile peritonitis. The nature and severity of the reaction was similar to that observed in Group I animals.

Group III—Treatment Control

These animals were exposed disodium cromoglycate (5 mg/ml in ethanol 50% v/v) and, 30 min later, to ovalbumin (5% w/v) by aerosol. There was a fall in respiration rate of 30% and in tidal volume of 40%, in response to the aerosol. Both parameters returned to normal within 10 min, the tidal volume remained normal throughout the monitoring period. The respiration rate rose by 10% 90 min after ovalbumin exposure, this lasted about 15 min. The major late phase peak did not occur in either parameter, indicating that the disodium cromoglycate pre-treatment has protected the animals from developing an asthmatic response to the ovalbumin. (FIG. 1) Following exposure to metacholine the tidal volume fell by 25% but the respiration rate rose by 5%. This may indicate a response to the metacholine insufficient to overcome the expected response to the aerosol. (FIG. 2) The reduced response to metacholine, compared to Group II controls, indicates that exposure to disodium cromoglycate has protected the animals from induced hyper-reactivity in the airway.

Post-mortem examination revealed that the animals had all developed severe sterile peritonitis. The nature of the reaction was similar to that observed in Group I and Group II animals. The reaction was less severe, as indicated by the absence of vascularisation of the fibrotic tissue, suggesting that disodium cromoglycate may have acted to protect these animals.

Group IV—Treatment Tests

These animals were exposed to 3C8 (5 mg/ml in ethanol 50% v/v) and, 30 min later, to ovalbumin (5% w/v) by aerosol. There was a fall in respiration rate of 40% and in tidal volume of 60%, in response to the aerosol. Both parameters returned to 90% of normal within 10 min, and fluctuated around 90% of normal for the remainder of the monitoring period. The major late phase peak did not occur in either parameter, indicting that the 3C8 pre-treatment has protected the animals from developing an asthmatic response to the ovalbumin. (FIG. 1) Following exposure to metacholine the tidal volume fell by 40% but the respiration rate rose by 10%. This may indicate a response to the matacholine insufficient to overcome the expected response to the aerosol. (FIG. 2) The reduced response to metacholine, compared to Group II controls, indicates that exposure to 3C8 have protected the animals from induced hyper-reactivity in the airway.

Post mortem examination revealed that none of the animals had developed the sterile peritonitis observed in the other groups. This would indicate that 3C8 has acted to protect these animals from an inflammatory response.

Conclusion

The protocol used to induce allergic asthma and bronchial hyper-reactivity in male Wistar rats was successful, except in the monitoring of the early phase of the allergic reaction. The treatment control (disodium cromoglycate) was successful in so far as it blocked the measureable responses to allergen and prevented the developemnt of bronchial hyper-reactivity. The test compound (3C8) was equally successful, if not marginally better, at blocking the allergic response and preventing development of bronchial hyper-reactivity. In addition, 3C8 may be acting as an anti-inflammatory agent, as indicated by the complete absence of peritonitis in 3C8 treated animals.

Inflammation models

Rat Paw Oedema Model

A range of doses of 3C8 compared to the response to single doses of indomethacin and hydrocortisone as follows:

| Drug | Concentration (mg/kg) | Paw Size (% Normal) | Std. Error (n = 6) |
| --- | --- | --- | --- |
| Indomethacin | 100 | 141.6 | 9.9 |
| Hydrocortisone | 100 | 115.4 | 4.8 |
| 3C8 | 100 | 107.9 | 7.8 |
| 3C8 | 30 | 120.0 | 7.8 |
| 3C8 | 10 | 99.85 | 6.6 |
| 3C8 | 3 | 137.3 | 5.7 |
| Solvent Control | 0 | 136.4 | 9.1 |

Mouse Ear Oedema Model

Responses of the mouse ear to single doses of a range of compounds compared to the response to indomethacin and dexamethasone, each at a dose of 300 $\mu$g per ear administered topically 30 min prior to administration of 400 $\mu$g or arachidonic acid. Values are expressed as the percentage increase in ear thickness 1 hour after administration of arachidonic acid (all n=4 except 8C4 (n=5)) and solvent controls (n=8). The results suggest that anti-inflammatory activity is not linked to mast cell stabilising activity.

| Compound | Mean % | SEM |
| --- | --- | --- |
| Dexamethasone | 37.9 | 8.5 |
| Indomethacin | 39.6 | 5.8 |
| 1C1 | 45.9 | 6.4 |
| 1C25 | 32.1 | 11.9 |
| 2C7 | 49.8 | 10.8 |
| 3C1 | 46.4 | 6.3 |
| 3C9 | 43.1 | 8.7 |
| 3C11 | 26.0 | 6.3 |
| 3C8 | 32.4 | 7.8 |
| Solvent Control | 78.8 | 15.2 |

It will be appreciated that the compounds may have useful pharmacological properties other than those described above.

The invention is not limited to the embodiments hereinbefore described which may be varied in detail.

APPENDIX 1

LIST OF ABBREVIATIONS USED

| | |
| --- | --- |
| $AlCl_3$ | aluminium chloride |
| aq | aqueous |
| b.p. | boiling point |
| $BrCH_2C_6H_4CO_2CH_3$ | methyl 4-(bromomethyl)benzoate |
| $BrCH_2CO_2CH_3$ | bromomethyl acetate |
| BSS | buffered salt solution |
| $CaCl_2$ | calcium chloride |
| $C_2H_5I$ | iodoethane |
| $C_6H_3(CH_3)Br(CH_3)$ | bromo-m-xylene |
| $C_6H_5CH_2Br$ | benzyl bromide |
| $CDCl_3$ | chloroform-d |
| $CF_3SO_3Si(CH_3)_3$ | trimethylsilyl trifluoromethanesulfonate (TMS triflate) |
| $CH(OCH_3)_3$ | trimethylsilyl orthoformate |
| $CH_3C_6H_4SO_3H.H_2O$ | p-toluenesulfonic |
| $CH_3I$ | iodomethane |
| $ClCH_2CH_2COCl$ | β-chloropropionylchloride |
| $CO_2$ | carbon dioxide |
| $CS_2$ | carbon disulfide |
| $[(C_6H_5)_3P]_3RhCl$ | tris(triphenylphosphine)rhodium(1) chloride (wilkinsons catalyst) |
| $[(CH_3)_3CO]_3Al$ | aluminium tri-tert-butoxide |
| DCM | dichloromethane |
| $dH_2O$ | distilled water |
| DMSO | dimethyl sulphoxide |
| DSCG | disodium cromoglycate |
| $Et_2O$ | ether |
| $Et_3N$ | triethylamine |
| EtOAc | ethyl acetate |
| EtOH | ethanol |
| $H_2C = CHCH_2Br$ | allyl bromide |
| $H_2NNH_2.H_2O$ | hydrazine hydrate.monohydrate |
| $H_2O$ | water |
| $H_2SO_4$ | sulphuric acid |
| HCl | hydrochloric acid |
| HEPES | N-2-hydroxyethylpiperazine-N-2-ethanesulphonic acid |
| $HOCH_2CH_2OH$ | ethylene glycol |
| IR | infra red |
| KCl | potassium chloride |
| LDA | lithium diisopropylamide |
| M | Molar |
| $MgCl_2$ | magnesium chloride |
| min | minutes |
| $\mu l$ | microlitres |
| mM | milli-molar |
| m.p. | melting point |
| $N_2$ | nitrogen |
| $NaBH_4$ | sodium borohydride |
| NaCl | sodium chloride |
| $NaCN(BH_3)$ | sodium cyanoborohydride |
| $NaHCO_3$ | sodium hydrogen carbonate |
| $NaHCO_3$ | sodium bicarbonate |
| $NaH_2PO$ | sodium hydrogen phosphate |
| NaOH | sodium hydroxide |
| $Na_2SO_4$ | sodium sulphate |
| $NH_4Cl$ | ammonium chloride |
| NMR | nuclear magnetic resonance |
| $O_2$ | oxygen |
| oPT | o-phthaldialdehyde |
| Pd | palladium |
| RT | room temperature |
| $^tBUOH$ | tert butanol |
| $^tBuOK$ | potassium tert butoxide |
| S.E.M. | standard error of mean |
| THF | tetrahydrofuran |
| TLC | thin layer chromatography |
| $\mu l$ | microliters |
| Triflic Acid | trifluoromethanesulfonic acid |
| TMS Triflate | trimethyl silyl trifluoromethanesulfonate |
| v/v | volume per volume |
| w/v | weight per volume |

APPENDIX 1-continued

LIST OF ABBREVIATIONS USED

| | |
|---|---|
| $ZnI_2$ | zinc iodide |
| $\lambda_{em}$ | emission wavelength |
| $\lambda_{2ex}$ | excitation wavelength |

APPENDIX 2

| | |
|---|---|
| 1C1 | 2-(1'-indanylidene)-indan-1-one |
| 1C2 | 2-(1-ind-1-enyl)-2-methylindan-1-one |
| 1C3 | 2-(1-ind-1-enyl)-2-methylindan-1-one |
| 1C4 | 2-(1=indanyl) -2-methylindane |
| 1C5 | 2-(1-ind-1-enyl)-2-methylindan-1-ol |
| 1C6 | 2-(1-indanyl)-2-methylindan-1-ol |
| 1C7 | 1-(2-(2-methylindanyl))ind-1-ene |
| 1C8 | 2-(1-ind-1-enyl)-2-methyl-1-acetoxyindane |
| 1C9 | 2-(3,3-dimethyl-1-ind-1-enyl)-2-methylindan-1-one |
| 1C10 | 2-(1-ind-1-enyl)-2-ethylindan-1-one |
| 1C11 | 2-(1-indanyl)-2-ethylindan-1-one |
| 1C12 | 2-(1-ind-1-enyl)-2-prop-2-enylindan-1-one |
| 1C13 | 2-(1-ind-1-enyl)-2-propylindan-1-one |
| 1C14 | 2-(1-indanyl)-2-propylindan-1-one |
| 1C15 | 2-(1-ind-1-enyl)-2-prop-2-enylindan-1-ol |
| 1C16 | 2-(1-ind-1-enyl)-2-prop-2-enyl-1-acetoxyindane |
| 1C17 | 2-(1-ind-lenyl)-2-propylindan-1-ol |
| 1C18 | 2-(1-ind-1-enyl)-2-propylindan-1-ol |
| 1C19 | 2-(ind-1-enyl)-2-propanyl-1-acetoxyindane |
| 1C20 | 2-(1-ind-1-enyl)-2-pent-2-enylindan-1-one |
| 1C21 | 2-(1-ind-1-enyl)-2-pentylindan-1-one |
| 1C22 | 2-(1-ind-1-enyl )-2-pent-2-enylindan-1-ol |
| 1C23 | 2-(1-ind-1-enyl)-2-pent-2-enylindan-1-ol |
| 1C24 | 2-(1-ind-1-enyl)-2-benzylindan-1-one |
| 1C25 and 1C26 | 2-(1-ind-1-enyl)-2-benzylindan-1-ol |
| 1C27 | 2-(1-ind-1-enyl)-2-benzl-1-acetoxyindane |
| 1C28 | 2-(1-indanyl)-2-benzylindane |
| 1C29 | 2-(1-indanyl)-2-benzylindan-1-one |
| 1C30 | 2-(1-indanyl)-2-benzylindan-1-ol |
| 1C31 | 2-(1-ind-1-enyl)-2-p-methoxycarbonyl-phenylmethyl-indan-1-one |
| 1C32 | 2-(1-ind-1-enyl)-2-p-carboxyphenyl-methylindan-1-one |
| 1C33 | 2-(1-ind-1-enyl)-2-methoxycarbonyl-methylindan-1-one |
| 1C34 | 2-(1-indenyl)-2-carboxymethylindan-1-one |
| 1C35 | 2-(1-ind-1-enyl)-2-sodium oxycarbonyl-methylindan-1-one |
| 1C36 | 2-(1-indanyl)-indane |
| 1C37 | 2-(1-indanyl)-indan-1-one |
| 1C38 | 2-(1-ind-1-enyl)-2-acetoxymethylindan-1-one |
| 1C39 | 1-(2-(2-benzyl-1-(3,5-dimethylpehnyl) aminocarbonylloxy)indanyl)-1-ind-1-ene |
| 1C40 | 1-(2-(2-benzyl-1-(3,5-dimethylphenyl) aminocarbonylloxy)indanyl)-1-ind-1-ene |
| 1C41 | 2-(1-(6-bromo-5,7-dimethylindanyl-idene))-1-(bromo-5,7-dimethylindan-1-one) |
| 1C42 | 2-(1-(1-(2-hydroxyethoxy)indanyl))-indan-1-one |
| 1C43 | 2-(1-ind-1-enyl)-indan-1-one ethylene ketal |
| 1C44 | 2-(1-ind-1-enyl)-indan-1-one-oxime |
| 2C1 | 1-(2-indanylidene)-indan-2-one |
| 2C2 | 1-(2-indenyl)-1-methylindan-2-one |
| 2C3 | 1-(2-indenyl)-1-ethylindan-2-one |
| 2C4 | 1-(2-indenyl)-indan-2-one |
| 2C5 | 1-(2-indanyl)-indan-2-ol |
| 2C6 | 1-(2-indenyl)-1-prop-enylindan-2-one |
| 2C7 | 1-(2-indenyl)-1-benzylindan-2-one |
| 2C8 | 1-(2-indenyl)-1-benzylindan-2-ol |
| 2C9 | 1-(benxyl-2-indanyl)-inden-2-ol |
| 2C10 | 1-(benzyl-2-inden-2-enyl)-inden-2-acetoxy |
| 2C11 | 2(2-benzyl-ind-1-enyl)-indene |
| 2C12 | 2-(2-(1-indan-1-onyl))-indan-1-one |
| 2C13 | 3-(2-(1-hydroxyindanyl)-indan-1-ol |
| 2C14 | 3-(2-(1-acetoxyindanyl))-1-acetoxyindane |

APPENDIX 2-continued

| | |
|---|---|
| 2C15 | 1-(2-indenyl)-1-benzyl-2-methan-sulfonylate-indane |
| 2C16 | 1-(2-indenyl)-2-benzyl-indan-2-one oxime |
| 3C1 | 2-(2-(2-methoxyindanyl))-indan-1-one |
| 3C2 | 2-(2'-indanylidene)-indan-1-one |
| 3C3 | 2-(2-indenyl)-2-prop-2-enylindan-1-one |
| 3C4 | 2-(2-indenyl)-2-propylindan-1-one |
| 3C5 | 2-(2-indenyl)-2-benzylindan-1-one |
| 3C6 | 2-(2-indenyl)-2-benzylindan-1-ol |
| 3C7 | 2-(2-indenyl)-2-benzylindan-1-ol |
| 3C8 | 2-(2-indenyl)-2-benzylindan-1-ol |
| 3C9 | 2-(2-indenyl)-2-benzylindan-1-ol |
| 3C10 | 2-(2-indenyl)-2-benzyl-1-acetoxyindane |
| 3C11 | 2-(2-indenyl)-2-p-methoxycarbonyl-phenylmethylindan-1-one |
| 3C12 | 2-(2-(2-methoxyindanyl))-4-methoxyindan-1-one |
| 3C13 | 2-(2-indenyl)-2-p-methoxycarbonyl-phenylmethyl-4-methoxyindan-1-one |
| 3C14 | 2-(2-(2-methoxyindanyl))-5-methoxyindan-1-one |
| 3C15 | 2-(2-indanylidene)-4-dodecyloxyindan-1-one |
| 3C16 | 2-(2-indenyl)-2-methoxycarbonlmethyl-4-dodecyloxyindan-1-one |
| 3C17 | 2-(2-(2-methoxyindanyl))-6-bromo-5,7-dimethylindan-1-one |
| 3C18 | 2-(2-indenyl_-2-benzyl-6-bromo-5,7-dimethylindan-1-one |
| 3C19 | 2-(2-indenyl)-2-benzyl-6-bromo-5,7 dimethylindan-1-ol |
| 3C20 | 2-(2-indenyl)-2-benzyl-6-bromo-5,7-dimethylindan-1-ol |
| 3C21 | 2-(2-(2-methoxyindanyl))-5-bromo-4,6-dimethylindan-1-one |
| 3C22 | 2-(2-indenyl)-2-benzyl-5-bromo-4,6-dimethylindan-1-one |
| 3C23 | 2-(2-indenyl)-2-benzyl-5-bromo-4,6-dimethylindan-1-ol |
| 3C24 | 2-(2-indenyl)-2-benzyl-5-bromo-4,6 dimethylindan-1-ol |
| 3C25 | 2-(2-(2-methoxyindanyl))-6-benzyloxy-5,7-dimethylindan-1-one |
| 3C26 | 2-(2-indenyl)-2-benzyl-6-benzyloxy-5,7-dimethylindan-1-one |
| 3C27 | 2-(2-(2-methoxyindanyl))-6-hydroxy-5,7-dimethylindan-1-one |
| 3C28 | 2-(2-(2-methoxyindanyl))-6-acetoxy-5,7 dimethylindan-1-one |
| 3C30 | 2-(-2-(2-methoxyindanyl)-5,7-dimethylindan-1-one |
| 3C31 | 2-(2-indenyl)-2-benzyl-5,7-dimethylindan-1-one |
| 3C32 | 2-(2-indenyl)-2-benzyl-5,7-dimethylindan-1-ol |
| 3C33 | 2-(2-indenyl)-2-benzyl-5,7-dimethylindan-1-ol |
| 3C36 | 2-(2-(2-methoxyindanyl))-indan-1-one oxime |
| 3C37 | 2-(2-indenyl)-inden-1-one oxime |
| 3C38 | 2-(2-(2-methoxyindanyl))-indan-1-one oxime benzyl ether |
| 3C39 | 2-(2-indanyl)-indan-1-one oximne benzyl ether |
| 3C40 | 2-(2-indenyl)-2-benzylindan-1-one oxime benzyl ether |
| 3C41 | 2-(1-indanyl)-2-benzylindan-1-one |
| 3C42 | 2-(1-indanyl)-2-benzylindan-1-one |
| 3C43 | 2-(2-methoxyindanyl)-4-prop-2-enyloxyindan-1-one |
| 4C1 | 1-(1-(2-hydroxyethoxy-1-indanyl))-indan-2-one |
| 4C2 | 3-(1-(indan-2-onyl))-indan-1-one |
| 4C3 | 3-(1-(indan-2-olyl))-indan-1-ol |

What is claimed is:

1. A pharmaceutical composition comprising a pharmaceutically acceptable carrier and a compound of any of the formulae:

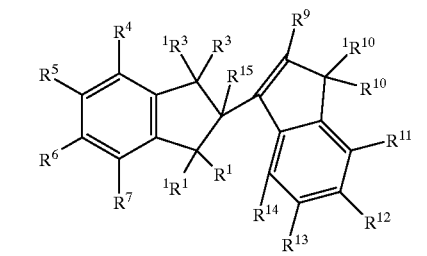

1

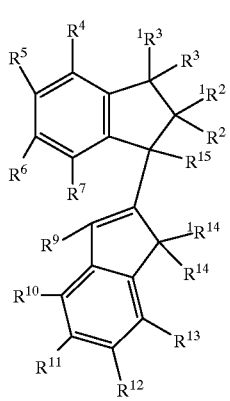

2

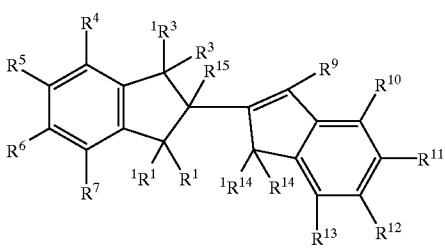

3 wherein in Formulae 1 and 3 $R^1$, $^1R^1$, $R^3$, $^1R^3$, $R^4$ to $R^7$, $R^9$, $R^{10}$, $^1R^{10}$, $R^{11}$ to $R^{13}$, $R^{14}$, $^1R^{14}$ and $R^{15}$ in Formula 2 $R^2$, $^1R^2$, $R^3$, $^1R^3$, $R^4$ to $R^7$, $R^9$ to $R^{13}$, $R^{14}$, $^1R^{14}$ and $R^{15}$ are selected from one or more of the same or different of:
H, halo, hydroxy, alkoxy, aryloxy, acetoxy, carboxy, alkyl carbonyl, hydro carbonyl, amino, amido, alkylamino, hydroxylamino, $C_1$–$C_{10}$ alkyl or $C_3$–$C_8$ cycloalkyl groups, substituted alkyl or cycloalkyl in Formula 1 any one or more of $R^1$, $^1R^1$; $R^3$, $^1R^3$; $R^{10}$, $^1R^{10}$ may together represent oxo;

in Formula 2 any one or more of $R^2$, $^1R^2$; $R^3$, $^1R^3$; $R^{14}$, $^1R^{14}$ may together represent oxo;

in Formula 3 any one or more of $R^1$, $^1R^1$; $R^3$, $^1R^3$; $R^{14}$, $^1R^{14}$ may together represent oxo.

2. A compound of any of the Formulae 1 to 3

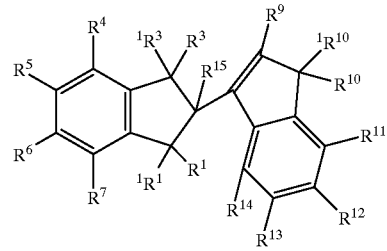

1

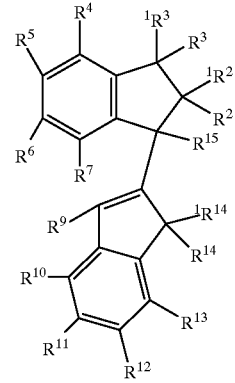

2

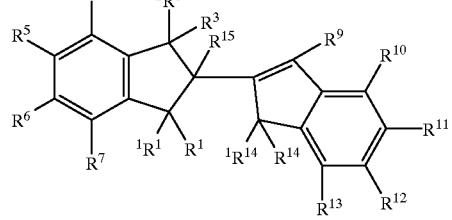

3 wherein in Formulae 1 and 3 $R^1$, $^1R^1$, $R^3$, $_1R^3$, $R^4$ to $R^7$, $R^9$, $R^{10}$, $^1R^{10}$, $R^{11}$ to $R^{13}$, $R^{14}$, $^1R^{14}$ and $R^{15}$ in Formula 2 $R^2$, $^1R^2$, $R^3$, $^1R^3$, $R^4$ to $R^7$, $R^9$ to $R^{13}$, $R^{14}$, $^1R^{14}$ and $R^{15}$ are selected from one or more of the same or different of:
H, halo, hydroxy, alkoxy, aryloxy, acetoxy, carboxy, alkyl carbonyl, hydro carbonyl, amino, amido, alkylamino, hydroxylamino, $C_1$–$C_{10}$ alkyl or $C_3$–$C_8$ cycloalkyl groups, substituted alkyl or cycloalkyl in Formula 1 any one or more of $R^1$, $^1R^1$; $R^3$, $^1R^3$; $R^{10}$, $^1R^{10}$ may together represent oxo;

in Formula 2 any one or more of $R^2$, $^1R^2$; $R^3$, $^1R^3$; $R^{14}$, $^1R^{14}$ may together represent oxo;

in Formula 3 any one or more of $R^1$, $^1R^1$; $R^3$, $^1R^3$; $R^{14}$, $^1R^{14}$ may together represent oxo;

other than the following:

2-(1-indenyl)-indanone;

1-(2-indenyl)-indane;

1-(2-indenyl)-1-methyl-indan-2-one; and 2,2'-biindenyl.

3. A compound as claimed in claim 2 wherein in Formula 1 $R^1$, $^1R^1$; $R^3$, $^1R^3$; and $R^{10}$, $^1R^{10}$ do not each represent oxo.

4. A compound as claimed in claim 2 wherein in Formula 2 $R^2$, $^1R^2$; $R^3$, $^1R^3$; and $R^{14}$, $^1R^{14}$ do not each represent oxo.

5. A compound as claimed in claim 2 wherein in Formula 3 $R^1$, $^1R^1$; $R^3$, $^1R^3$; and $R^{14}$, $^1R^{14}$ do not each represent oxo.

6. A compound as claimed in claim 2 wherein the alkyl or cycloalkyl is substituted with one or more of the same or different of halo, oxo, hydroxy, alkoxy, aryloxy, acetoxy, carboxy, carbonyl, amino, amido, alkylamino, hydroxylamino.

7. A compound as claimed in claim 2 wherein in Formula 1 $R^3$, and $^1R^3$ to $R^7$ are hydrogen.

8. A compound as claimed in claim 2 wherein in Formula 1 $R^{10}$, and $^1R^{10}$ to $R^{14}$ are hydrogen.

9. A compound as claimed in claim 2 wherein in Formula 1 $R^1$ and $^1R^1$ independently represent H or OH.

10. A compound as claimed in claim 2 wherein in Formula 1 $R^{15}$ represents a benzyl group.

11. A compound as claimed in claim 2 wherein in Formula 2 each of $R^3$ and $^1R^3$ to $R^7$ is hydrogen.

12. A compound as claimed in claim 2 wherein in Formula 2 each of $R^{10}$ to $R^{13}$ is hydrogen.

13. A compound as claimed in claim 2 wherein in Formula 2 each of $R^2$ and $^1R^2$ independently represents H or OH.

14. A compound as claimed in claim 2 wherein in Formula 2 $R^{15}$ represents a benzyl group.

15. A compound as claimed in claim 2 wherein in Formula 3 each of $R^4$ to $R^7$ represents hydrogen.

16. A compound as claimed in claim 2 wherein in Formula 3 each of $R^{10}$ to $R^{13}$ represents hydrogen.

17. A compound as claimed in claim 2 wherein in Formula 3 each of $R^1$ and $^1R^1$ independently represents H or OH.

18. A compound as claimed in claim 2 wherein in Formula 3 $R^{15}$ represents a benzyl group.

19. A compound selected from the group consisting of:

1C4 2-(1-indanyl)-2-methylindane
1C5 2-(1-ind-1-enyl)-2-methylindan-1-ol
1C7 1-(2-(2-methylindanyl))ind-1-ene
1C8 1-(1-ind-1-enyl)-2-methyl-1-acetoxyindane
1C9 2-(3,3-dimethyl-1-ind-1-enyl))-2-methylindan-1-one
1C10 2-(1-ind-1-enyl)-2-ethylindan-1-one
1C12 2-(1-ind-1-enyl)-2-prop-2-enylindan-1-one
1C13 2-(1-ind-1-enyl)-2-propylindan-1-one
1C15 2-(1-ind-1-enyl)-2-prop-2-enylindan-1-ol
1C16 2-(1-ind-1-enyl)-2-prop-2-enyl-1-acetoxyindane
1C17 2-(1-ine-1-enyl)-2-propylindan-1-ol
1C18 2-(1-ind-1-enyl)-2-propylindan-1-ol
1C19 2-(ind-1-enyl)-2-propanyl-1-acetoxyindane
1C20 2-(1-ind-1-enyl)-2-pent-2-enylindan-1-one
1C21 2-(1-ind-1-enyl)-2-pentylindan-1-one
1C22 2-(1-ind-1-enyl)-2-pent-2-enylindan-1-ol
1C23 2-(1-ind-1-enyl)-2-pent-2-enylindan-1-ol
1C24 2-(1-ind-1-enyl)-2-benzylindan-1-one
1C25 and 1C26 2-(1-ind-1-enyl)-2-benzylindan-1-ol
1C27 2-(1-ind-1-enyl)-2-benzyl-1-acetoxyindane
1C31 2-(1-ind-1-enyl)-2-p-methoxycarbonylphenylmethylindan-1-one
1C32 2-(1-ind-1-enyl)-2-p-carboxyphenylmethylindan-1-one
1C33 2-(1-ind-1-enyl)-2-methoxycarbonylmethylindan-1-one
1C34 2-(1-indenyl)-2-carboxymethylindan-1-one
1C35 2-(1-ind-1-enyl)-2-sodium oxycarbonylmethylindan-1-one
1C38 2-(1-ine-1-enyl)-2-acetoxymethylindan-1-one
2C3 1-(2-indenyl)-1-ethylindan-2-one
2C4 1-(2-indenyl)-indan-2-one
2C6 1-(2-indenyl)-1-prop-2-enylindan-2-one
2C7 1-(2-indenyl)-1-benzylindan-2-one
2C8 1-(2-indenyl)-1-benzylindan-2-ol
2C10 1-(benzyl-2-inden-2-enyl)-inden-2-acetoxy
3C3 2-(2-indenyl)-2-prop-2-enylindan-1-one
3C4 2-(2-indenyl)-2-propylindan-1-one
3C5 2-(2-indenyl)-2-benzylindan-1-one
3C6 2-(2-indenyl)-2-benzylindan-1-ol
3C7 2-(2-indenyl)-2-benzylindan-1-ol
3C8 2-(2-indenyl)-2-benzylindan-1-ol
3C9 2-(2-indenyl)-2-benzylindan-1-ol
3C10 2-(2-indenyl)-2-benzyl-1-acetoxyindane
3C11 2-(2-indenyl)-2-p-methoxycarbonylphenylmethylindan-1-one
3C13 2-(2-indenyl)-2-p-methoxycarbonyl-phenylmethyl-4-methoxyindan-1-one
3C 18 2-(2-indenyl)-1-benzyl-6-bromo-5,7-dimethylindan-1-one
3C19 2-(2-indenyl)-2-benzyl-6-bromo-5,7-dimethylindan-1-ol
3C20 2-(2-indenyl)-2-benzyl-6-bromo-5,7-dimethylindan-1-ol
3C22 2-(2-indenyl)-2-benzyl-5-bromo-4,6-dimethylindan-1-one
3C23 2-(2-indenyl)-2-benzyl-5-bromo-4,6-dimethylindan-1-ol
3C24 2-(2-indenyl)-2-benzyl-5-bromo-4,6-dimethylindan-1-ol
3C31 2-(2-indenyl)-2-benzyl-5,7-dimethylindan-1-one
3C32 2-(2-indenyl)-2-benzyl-5,7-dimethylindan-1-ol and
3C33 2-(2-indenyl)-2-benzyl-5,7-dimethylindan-1-ol.

20. A compound of Formula 1 of claim 2.

21. A compound of Formula 2 of claim 2.

22. A compound of Formula 3 of claim 2.

23. A pharmaceutical composition comprising a compound of claim 2 and a pharmaceutically acceptable carrier.

24. A method of treatment to achieve smooth muscle relaxing activity and/or mast cell stabilizing activity and/or anti-inflammatory activity which comprises administering an effective amount of a compound of claim 2 to a subject in need of such therapy.

* * * * *

UNITED STATES PATENT AND TRADEMARK OFFICE
CERTIFICATE OF CORRECTION

PATENT NO.    : 6,300,376 B1
DATED         : October 9, 2001
INVENTOR(S)   : Walsh et al.

It is certified that error appears in the above-identified patent and that said Letters Patent is hereby corrected as shown below:

<u>Title page,</u>
Item [63], "Jun. 12, 1996" should be -- Dec. 6, 1996 --.

Signed and Sealed this

Eighteenth Day of June, 2002

*Attest:*

*Attesting Officer*

JAMES E. ROGAN
*Director of the United States Patent and Trademark Office*